(12) United States Patent
Rabito et al.

(10) Patent No.: US 11,633,279 B2
(45) Date of Patent: Apr. 25, 2023

(54) PROSTHESIS, DELIVERY DEVICE AND METHODS OF USE

(71) Applicant: Edwards Lifesciences CardiAQ LLC, Irvine, CA (US)

(72) Inventors: Glen T. Rabito, Lake Forest, CA (US); Jeremy Brent Ratz, Winchester, MA (US); Arshad Quadri, West Hartford, CT (US); Lindsay Lam, Tustin, CA (US); David Robert Landon, Huntington Beach, CA (US); Garrett Dallas Johnson, Costa Mesa, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 200 days.

(21) Appl. No.: 17/207,327

(22) Filed: Mar. 19, 2021

(65) Prior Publication Data

US 2021/0205083 A1    Jul. 8, 2021

Related U.S. Application Data

(60) Continuation of application No. 16/015,065, filed on Jun. 21, 2018, now Pat. No. 10,952,849, which is a
(Continued)

(51) Int. Cl.
*A61F 2/24* (2006.01)

(52) U.S. Cl.
CPC .......... *A61F 2/2436* (2013.01); *A61F 2/2439* (2013.01); *A61F 2/2418* (2013.01);
(Continued)

(58) Field of Classification Search
CPC .... A61F 2/2436; A61F 2/2439; A61F 2/2418; A61F 2220/0008; A61F 2220/0025;
(Continued)

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

(Continued)

*Primary Examiner* — Phong Son H Dang
(74) *Attorney, Agent, or Firm* — Knobbe Martens Olson & Bear LLP

(57) ABSTRACT

Methods for delivering a replacement heart valve include advancing a delivery system through a femoral vein and into the atrium of a heart, wherein the delivery system includes an outer sheath assembly, a mid shaft assembly and an inner assembly. The outer sheath assembly and the mid shaft assembly are adapted to retain the replacement heart valve in a radially compacted state over the inner assembly. The outer sheath assembly is retracted to allow a plurality of distal anchors to self-expand while a portion of the replacement heart valve remains retained in a compacted state by the mid shaft assembly. The distal anchors are positioned to engage one or more native leaflets and the retained portion of the replacement heart valve is then released and allowed to fully expand for implanting the replacement heart valve within the native valve.

20 Claims, 37 Drawing Sheets

Related U.S. Application Data division of application No. 14/628,034, filed on Feb. 20, 2015, now Pat. No. 10,004,599.

(60) Provisional application No. 62/004,637, filed on May 29, 2014, provisional application No. 61/950,748, filed on Mar. 10, 2014, provisional application No. 61/943,270, filed on Feb. 21, 2014.

(52) U.S. Cl.
CPC ............... *A61F 2220/0008* (2013.01); *A61F 2220/0025* (2013.01); *A61F 2220/0033* (2013.01); *A61F 2230/0067* (2013.01); *A61F 2250/001* (2013.01)

(58) Field of Classification Search
CPC ...... A61F 2220/0033; A61F 2230/0067; A61F 2250/001
See application file for complete search history.

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,380,457 B1 | 4/2002 | Yurek et al. |
| 6,440,164 B1 | 8/2002 | DiMatteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,565,597 B1 | 5/2003 | Fearnot et al. |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,699,274 B2 | 3/2004 | Stinson |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,632,296 B2 | 12/2009 | Malewicz |
| 7,753,949 B2 | 7/2010 | Lamphere et al. |
| 7,763,063 B2 * | 7/2010 | Arbefeuille ............... A61F 2/07 623/1.11 |
| 7,803,185 B2 | 9/2010 | Gabbay |
| 7,806,919 B2 | 10/2010 | Bloom et al. |
| 7,815,673 B2 | 10/2010 | Bloom et al. |
| 7,914,569 B2 | 3/2011 | Nguyen et al. |
| 7,947,075 B2 | 5/2011 | Goetz et al. |
| 7,972,378 B2 | 7/2011 | Tabor et al. |
| 7,981,151 B2 | 7/2011 | Rowe |
| 7,993,392 B2 | 8/2011 | Righini et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,252,051 B2 | 8/2012 | Chau et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,981 B2 | 3/2013 | Forster et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |

(56) References Cited

U.S. PATENT DOCUMENTS

| | | |
|---|---|---|
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,623,075 B2 | 1/2014 | Murray, III et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,079 B2 | 9/2014 | Thielen et al. |
| 8,845,718 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,998,980 B2 | 4/2015 | Shipley et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,751 B2 | 7/2015 | Naor |
| 9,084,676 B2 | 7/2015 | Chau et al. |
| 9,125,738 B2 | 9/2015 | Figulla et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,333,073 B2 * | 5/2016 | Quadri ............... A61F 2/2439 |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0023300 A1 | 1/2003 | Bailey et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0093063 A1 * | 5/2004 | Wright ............... A61F 2/95 623/1.12 |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210307 A1 | 10/2004 | Khairkhahan |
| 2004/0215325 A1 | 10/2004 | Penn et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137690 A1 * | 6/2005 | Salahieh ............... A61F 2/2427 623/1.36 |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0288766 A1 * | 12/2005 | Plain ............... A61F 2/97 623/1.12 |
| 2006/0020327 A1 | 1/2006 | Lashinski et al. |
| 2006/0025844 A1 * | 2/2006 | Majercak ............... A61F 2/9661 623/1.11 |
| 2006/0052867 A1 | 3/2006 | Revuelta et al. |
| 2006/0095115 A1 | 5/2006 | Bladillah et al. |
| 2006/0173537 A1 | 8/2006 | Yang et al. |
| 2006/0184226 A1 * | 8/2006 | Austin ............... A61F 2/95 623/1.11 |
| 2006/0195183 A1 | 8/2006 | Navia et al. |
| 2006/0212110 A1 | 9/2006 | Osborne et al. |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071361 A1 * | 3/2008 | Tuval ............... A61F 2/2418 623/2.1 |
| 2008/0082164 A1 | 4/2008 | Friedman |
| 2008/0082165 A1 | 4/2008 | Wilson et al. |

(56) References Cited

U.S. PATENT DOCUMENTS

| | | |
|---|---|---|
| 2008/0097581 A1 | 4/2008 | Shanley |
| 2008/0140178 A1* | 6/2008 | Rasmussen ............... A61F 2/89 623/1.11 |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0188928 A1* | 8/2008 | Salahieh ........... A61M 25/0054 623/2.11 |
| 2008/0208328 A1 | 8/2008 | Antocci et al. |
| 2008/0228254 A1 | 9/2008 | Ryan |
| 2008/0262590 A1* | 10/2008 | Murray ..................... A61F 2/95 623/1.11 |
| 2009/0005863 A1 | 1/2009 | Goetz et al. |
| 2009/0048656 A1* | 2/2009 | Wen ....................... A61F 2/2439 623/1.12 |
| 2009/0054976 A1* | 2/2009 | Tuval .................... A61F 2/2427 623/2.11 |
| 2009/0069889 A1* | 3/2009 | Suri ...................... A61F 2/2433 623/2.11 |
| 2009/0138079 A1* | 5/2009 | Tuval .................... A61F 2/2418 623/2.11 |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0192585 A1* | 7/2009 | Bloom ...................... A61F 2/07 623/1.26 |
| 2009/0192586 A1* | 7/2009 | Tabor ................... A61F 2/2412 623/1.36 |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0049313 A1 | 2/2010 | Alon et al. |
| 2010/0094411 A1* | 4/2010 | Tuval .................... A61F 2/2418 623/2.11 |
| 2010/0100167 A1* | 4/2010 | Bortlein ................... A61F 2/95 623/1.11 |
| 2010/0114305 A1 | 5/2010 | Kang et al. |
| 2010/0121434 A1* | 5/2010 | Paul ..................... A61F 2/2418 623/2.11 |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0286768 A1* | 11/2010 | Alkhatib ................ A61F 2/2439 623/2.11 |
| 2010/0305685 A1 | 12/2010 | Millwee et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0264198 A1* | 10/2011 | Murray, III ........... A61F 2/2418 623/2.11 |
| 2011/0307049 A1* | 12/2011 | Kao ....................... A61F 2/966 623/1.11 |
| 2011/0319989 A1* | 12/2011 | Lane ..................... A61F 2/2436 623/2.37 |
| 2012/0022639 A1 | 1/2012 | Hacohen et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0245676 A1* | 9/2012 | Dierking ................. A61F 2/95 623/1.16 |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2015/0005863 A1 | 1/2015 | Para |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |

(56) References Cited

U.S. PATENT DOCUMENTS

| | | |
|---|---|---|
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0056169 A1* | 3/2017 | Johnson ............... A61F 2/2436 |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | | |
|---|---|---|---|
| CN | 102196784 A | | 9/2011 |
| CN | 102836020 A | | 12/2012 |
| DE | 102006052564 B3 | | 12/2007 |
| EP | 1171059 A1 | | 1/2002 |
| EP | 1369098 A1 | | 12/2003 |
| EP | 1472996 A1 | | 11/2004 |
| EP | 1259194 B1 | | 2/2005 |
| EP | 1734903 A1 | | 12/2006 |
| EP | 1255510 B1 | | 4/2007 |
| EP | 1827558 A2 | | 9/2007 |
| EP | 1239901 B1 | | 10/2007 |
| EP | 1935377 B1 | | 3/2010 |
| EP | 2237746 A2 | | 10/2010 |
| EP | 2238947 A2 | | 10/2010 |
| EP | 2285317 A1 | | 2/2011 |
| EP | 2308425 A1 | | 4/2011 |
| EP | 2398543 A1 | | 12/2011 |
| EP | 1281375 B1 | | 2/2012 |
| EP | 2496182 A1 | | 9/2012 |
| EP | 2529701 A1 | | 12/2012 |
| EP | 2566416 A1 | | 3/2013 |
| EP | 2319458 B1 | | 4/2013 |
| EP | 2124826 B1 | | 7/2014 |
| EP | 2750630 A1 | | 7/2014 |
| EP | 2777617 A1 | | 9/2014 |
| EP | 2815723 A1 | | 12/2014 |
| EP | 2815725 A1 | | 12/2014 |
| EP | 2898858 A1 | | 7/2015 |
| EP | 2967858 A2 | | 1/2016 |
| EP | 2168536 B1 | | 4/2016 |
| EP | 2262451 B1 | | 5/2017 |
| EP | 3184083 A1 | | 6/2017 |
| EP | 2446915 B1 | | 1/2018 |
| EP | 3057541 B1 | | 1/2018 |
| EP | 3037064 B1 | | 3/2018 |
| EP | 3046511 B1 | | 3/2018 |
| EP | 3142603 B1 | | 3/2018 |
| EP | 3294220 A1 | | 3/2018 |
| GB | 1264471 A | | 2/1972 |
| GB | 1315844 A | | 5/1973 |
| GB | 2398245 A | | 8/2004 |
| JP | 2002540889 A | | 12/2002 |
| WO | 9749355 A1 | | 12/1997 |
| WO | 0061034 A1 | | 10/2000 |
| WO | 03092554 A1 | | 11/2003 |
| WO | 2004030569 A2 | | 4/2004 |
| WO | 2005011534 A1 | | 2/2005 |
| WO | 2006070372 A2 | | 7/2006 |
| WO | 2006085225 A1 | | 8/2006 |
| WO | 2006089236 A1 | | 8/2006 |
| WO | 2007025028 A1 | | 3/2007 |
| WO | 2007058857 A2 | | 5/2007 |
| WO | 2007098232 A2 | | 8/2007 |
| WO | 2007123658 A1 | | 11/2007 |
| WO | 2008013915 A2 | | 1/2008 |
| WO | 2008070797 A2 | | 6/2008 |
| WO | 2008103722 A2 | | 8/2008 |
| WO | 2008125153 A1 | | 10/2008 |
| WO | 2008150529 A1 | | 12/2008 |
| WO | 2009026563 A2 | | 2/2009 |
| WO | 2009045331 A1 | | 4/2009 |
| WO | 2009053497 A1 | | 4/2009 |
| WO | 2009091509 A1 | | 7/2009 |
| WO | 2009094500 A1 | | 7/2009 |
| WO | 2009134701 A2 | | 11/2009 |
| WO | 2010005524 A2 | | 1/2010 |
| WO | 2010008549 A1 | | 1/2010 |
| WO | 2010022138 A2 | | 2/2010 |
| WO | 2010040009 A1 | | 4/2010 |
| WO | 2010057262 A1 | | 5/2010 |
| WO | 2010121076 A2 | | 10/2010 |
| WO | 2011025945 A1 | | 3/2011 |
| WO | 2011057087 A1 | | 5/2011 |
| WO | 2011111047 A2 | | 9/2011 |
| WO | 2011137531 A1 | | 11/2011 |
| WO | 2012177942 A2 | | 12/2012 |
| WO | 2013028387 A2 | | 2/2013 |
| WO | 2013075215 A1 | | 5/2013 |
| WO | 2013120181 A1 | | 8/2013 |
| WO | 2013175468 A2 | | 11/2013 |
| WO | 2013192305 A2 | | 12/2013 |
| WO | 2014018432 A2 | | 1/2014 |
| WO | 2014099655 A1 | | 6/2014 |
| WO | 2014110019 A1 | | 7/2014 |
| WO | 2014110171 A2 | | 7/2014 |
| WO | 2014121042 A1 | | 8/2014 |
| WO | 2014139545 A1 | | 9/2014 |
| WO | 2014145338 A1 | | 9/2014 |
| WO | 2014149865 A1 | | 9/2014 |
| WO | 2014163706 A1 | | 10/2014 |
| WO | 2014164364 A1 | | 10/2014 |
| WO | 2014194178 A1 | | 12/2014 |
| WO | 2014204807 A1 | | 12/2014 |
| WO | 2014205064 A1 | | 12/2014 |
| WO | 2014210124 A1 | | 12/2014 |
| WO | 2015077274 A1 | | 5/2015 |
| WO | 2015148241 A1 | | 10/2015 |
| WO | 2016016899 A1 | | 2/2016 |

OTHER PUBLICATIONS

Bavaria, Joseph E. M.D. et al.: "Transcatheter Mitral Valve Implantation: The Future Gold Standard for MR?," Applicant requests the Examiner to consider this reference to be prior art as of Dec. 2010.
Int'l. Search Report for PCT/US2015/016927, dated Jul. 20, 2015.
Search Report issued in CN Application No. 2015800188884, dated May 10, 2017.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Bavaria, Joseph E. M.D.: "CardiAQ Valve Technologies: Transcatheter Mitral Valve Implantation," Sep. 21, 2009.

(56) References Cited

OTHER PUBLICATIONS

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 46, No. 2, Jul. 19, 2005:360-5.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial—Mitral-Valve Prosthesis' for Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Seidel, Wolfgang, et al., "A Mitral Valve Prosthesis and a Study of Thrombosis on Heart Valves in Dogs," JSR13 vol. II, No. 3—May 1962, submitted for publication Oct. 9, 1961.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.
Ratz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes this may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.
Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

(56) References Cited

OTHER PUBLICATIONS

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.

* cited by examiner

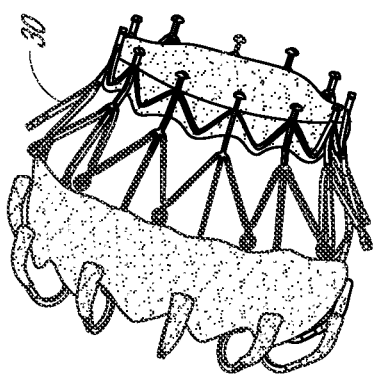
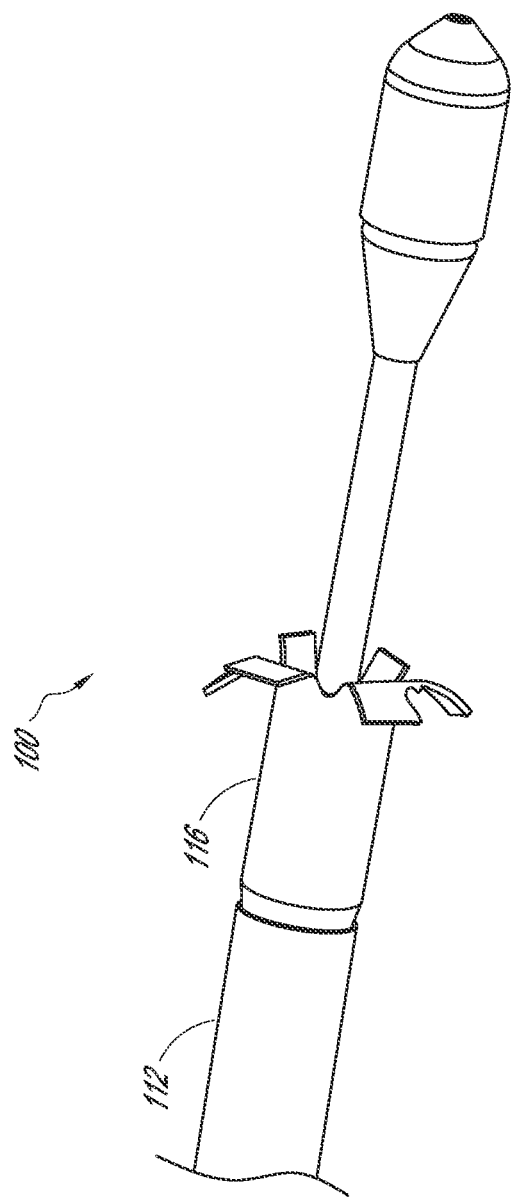
FIG. 22

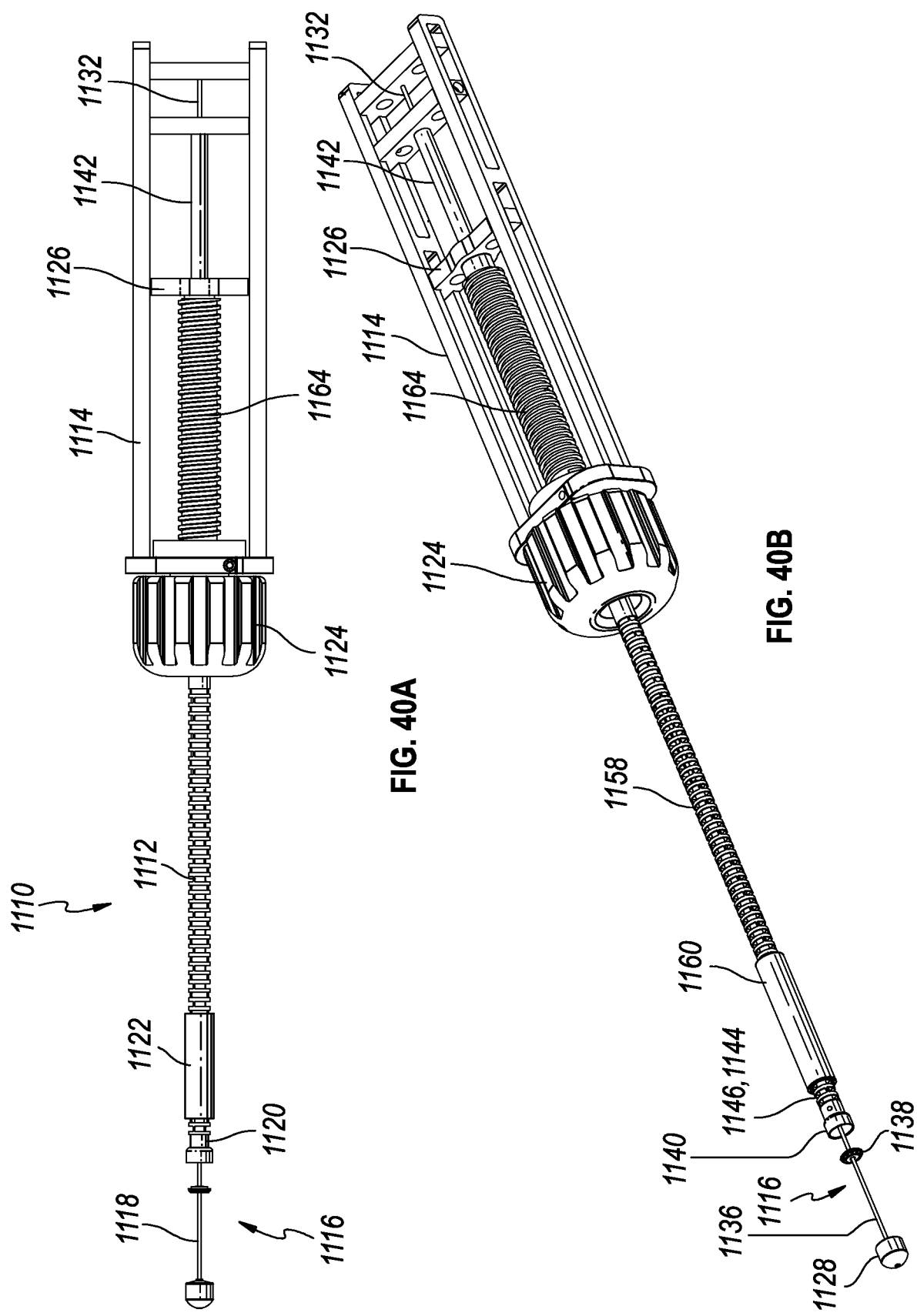

PROSTHESIS, DELIVERY DEVICE AND METHODS OF USE

CROSS-REFERENCE TO RELATED APPLICATIONS

This application is a continuation of U.S. patent application Ser. No. 16/015,065, filed Jun. 21, 2018, now U.S. Pat. No. 10,952,849, which is a divisional of U.S. patent application Ser. No. 14/628,034, filed Feb. 20, 2015, now U.S. Pat. No. 10,004,599, which claims priority to U.S. Provisional App. No. 61/943,270 filed Feb. 21, 2014, titled PROSTHESIS DELIVERY DEVICE AND METHODS OF USE, U.S. Provisional App. No. 61/950,748 filed Mar. 10, 2014, titled PROSTHESIS, DELIVERY DEVICE AND METHODS OF USE, and U.S. Provisional App. No. 62/004,637 filed May 29, 2014, titled PROSTHESIS, DELIVERY DEVICE AND METHODS OF USE, each of which is hereby incorporated herein by reference in its entirety and is to be considered a part of this specification.

BACKGROUND

Field

Certain embodiments disclosed herein relate generally to prostheses for implantation within a lumen or body cavity and delivery devices for a prosthesis. In particular, the prostheses and delivery devices relate in some embodiments to replacement heart valves, such as replacement mitral heart valves.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

According to some embodiments, a delivery system can be used for controlled deployment of a prosthesis or replacement valve. In some embodiments, the delivery system can comprise a first member, a second member, and a tether. The first member can be configured to at least partially restrain a first end of the prosthesis or replacement valve. The second member can be configured to at least partially restrain a second end of the prosthesis or replacement valve. The tether can be configured to at least partially encircle the prosthesis or replacement valve and radially restrain at least a portion of the prosthesis or replacement valve after the second member has been removed from the second end of the prosthesis or replacement valve. The tether can be configured to radially restrain at least a portion of the prosthesis or replacement valve while the first member still at least partially restrains the first end of the prosthesis or replacement valve.

According to some embodiments, the first member can comprise a first shaft and the second member can comprise a second shaft, the second shaft being positioned over the first shaft and slidable relative to the first shaft. The first member can comprise a nose cone configured to receive and cover the first end of the prosthesis or replacement valve. The nose cone can be connected to a distal end of the first shaft. The nose cone can comprise a proximally-facing opening to receive at least a first end of the prosthesis or replacement valve. The nose cone can comprise a taper towards the distal end of the nose cone. An outer diameter of the nose cone can be similar to an outer diameter of the second shaft. An outer diameter of the nose cone is similar to an inner diameter of the second shaft. The first member can comprise an inner retention ring configured to engage the first end of the prosthesis or replacement valve. The inner retention ring can be connected to a distal portion of an inner retention shaft. The inner retention shaft can be positioned between the first shaft and the second shaft and be slidable relative to the first shaft. The inner retention ring can comprise a taper towards a proximal end of the inner retention ring. The inner retention ring can comprise a cavity at or near a distal end of the inner retention ring. The inner retention ring can comprise a compressible member received at least partially within the cavity, the compressible member having a compressed diameter and an expanded diameter.

According to some embodiments, the delivery system can comprise a tether retention assembly configured to restrain the tether such that the tether can be tensioned to restrain at least a portion of the prosthesis or replacement valve. The tether retention assembly can comprise an inner component and an outer component. The outer component can be configured to cooperate with the inner component to restrain the tether. The inner component can comprise a C-lock. The outer component can comprise a sheath. The outer component can be moveable relative to the inner component to release the tether. The tether retention assembly can further comprise a locking shaft. The outer component can be positioned at or near a distal end of the locking shaft. The locking shaft can comprise a radial protrusion which can be configured to maintain radial alignment between the locking shaft and the second shaft. The locking shaft can comprise a guide member for the tether.

According to some embodiments, the second member can comprise an outer elongate hollow member configured to cover at least the second end of the prosthesis or replacement valve. The outer elongate member can be connected to a distal end of the second shaft. The outer elongate hollow member can have a substantially constant diameter throughout the entirety of its length. The diameter of the outer elongate hollow member can be substantially similar to a diameter of the second shaft The outer elongate hollow member can be moveable relative to the first member to uncover the second end of the prosthesis or replacement valve while the first end of the prosthesis or replacement valve remains engaged to the first member. The delivery system can comprise an introducer sheath positioned over the second shaft. The delivery system can comprise a plug, the plug being moveable to engage the first member when the first member is retrieved from a patient. The delivery system can comprise a plug shaft positioned between the first shaft and the second shaft and can be slidable relative to the first shaft. The first shaft can be hollow to receive a guidewire.

According to some embodiments, the delivery system can comprise a prosthesis or replacement valve, wherein a first end of the prosthesis or replacement valve engages the first member and a second end of the prosthesis or replacement valve engages the second member.

According to some embodiments, a delivery system can be used for controlled deployment of a prosthesis or replacement valve. The delivery system can comprise a nose cone shaft, a nose cone, an inner retention shaft, an inner retention ring, a tether retention member, a locking shaft, an outer elongate hollow member shaft, and an outer elongate hollow member. The nose cone can be connected to the distal end of the nose cone shaft. The nose cone can comprise a proximally-facing opening to receive at least a first end of the prosthesis or replacement valve. The inner retention shaft can be slidable over the nose cone shaft. The inner retention ring can be connected to the distal end of the inner retention shaft. The inner retention ring can be configured to engage the first end of the prosthesis or replacement valve. The tether retention member can be on the inner retention shaft. The locking shaft can be slidable over the inner retention shaft. The locking shaft can be configured to cooperate with the tether retention member to releasably engage a tether attached to the prosthesis or replacement valve. The outer elongate hollow member shaft can be slidable over the locking shaft. The outer elongate hollow member can be connected to the distal end of the outer elongate hollow member shaft. The outer elongate hollow member can have a proximal end and a distal end, the outer elongate hollow member being configured to cover at least the second end of the prosthesis or replacement valve when the first end of the prosthesis or replacement valve is engaged with the inner retention ring and is covered by the nose cone. The outer elongate hollow member can be moveable relative to the nose cone to uncover the second end of the prosthesis or replacement valve while the first end of the prosthesis or replacement valve remains engaged to the inner retention ring and is covered by the nose cone.

According to some embodiments, the nose cone can comprise a taper towards the distal end of the nose cone. An outer diameter of the nose cone can be similar to an outer diameter of at least one of the outer elongate hollow member shaft and the outer elongate hollow member. An outer diameter of the nose cone can be similar to an inner diameter of at least one of the outer elongate hollow member shaft and the outer elongate hollow member. The inner retention ring can comprise a taper towards a proximal end of the inner retention ring. The inner retention ring can comprise a cavity at or near a distal end of the inner retention ring. The inner retention ring can comprise a compressible member received at least partially within the cavity, the compressible member having a compressed diameter and an expanded diameter. The compressed diameter can be approximately equal to an inner diameter of the nose cone and the expanded diameter can be greater than the inner diameter of the nose cone. The locking shaft can comprise a radial protrusion configured to maintain radial alignment between the locking shaft and the outer elongate hollow member shaft. The locking shaft can comprise a guide member for the tether. The outer elongate hollow member can have a substantially constant diameter throughout the entirety of its length. The diameter of the outer elongate hollow member can be substantially similar to a diameter of the outer elongate hollow member shaft.

According to some embodiments, the delivery system can comprise an introducer sheath having a proximal end and a distal end slidable over the outer elongate hollow member shaft. The tether retention member can comprise a C-lock. The delivery system can comprise a lock at the distal end of the locking shaft to cover the C-lock to releasably retain a tether therein. The delivery system can comprise a plug shaft having a proximal end and a distal end. The plug shaft can be slidable over the locking shaft and the outer elongate hollow member shaft can be slidable over the plug shaft. The delivery system can comprise a plug at the distal end of the plug shaft to engage the nose cone when the nose cone is retrieved from a patient. The nose cone shaft can be hollow to receive a guidewire.

According to some embodiments, the delivery system can comprise a prosthesis or replacement valve. A first end of the prosthesis or replacement valve can engage the inner retention ring and can be covered by the nose cone. A second end of the prosthesis or replacement valve can be covered by the outer elongate hollow member shaft. A tether can be connected to the tether retention member, the tether retention member being covered by a lock at the distal end of the locking shaft, the tether wrapping at least partially around the prosthesis or replacement valve and then extending proximally through at least the outer elongate hollow member shaft.

According to some embodiments, a method of delivery of a prosthesis or replacement valve can comprise: delivering an intralumenal frame assembly to the in situ target location while the frame assembly is in a radially compacted state within an outer member, the frame assembly comprising a frame having a first end, a second end and a longitudinal axis extending between the first and second ends, the frame further comprising a tether encircling at least a portion of the frame, the tether configured to restrain the radial dimension of the frame; at least partially removing the outer member from the frame assembly, wherein the tether restrains the radial dimension of the frame after the outer member is at least partially removed; and releasing the tether from the frame to allow at least a portion of the frame assembly to radially expand.

According to some embodiments, releasing the tether from the frame can allow the second end of the frame to radially expand while the first end of the frame remains radially restrained. The method can comprise radially expanding the first end of the frame after releasing the tether to allow the second end of the frame to radially expand. The first end of the frame, prior to radial expansion, can be restrained by a nose cone covering at least the first end of the frame. The outer member can be at least partially removed from the frame assembly by moving the outer member relatively away from the nose cone. The outer member can be at least partially removed in a proximal direction from the frame assembly by moving the outer member relatively away from the nose cone.

According to some embodiments, the intralumenal frame assembly can comprise a plurality of anchors at its second end, wherein the plurality of anchors extend proximally away from the second end of the frame assembly as the outer member is moved proximally. The plurality of anchors can flip to extend distally away from the second end of the frame assembly after the outer member uncovers the plurality of anchors. The tether can radially restrain the frame assembly during flipping of the anchors. The intralumenal frame assembly can comprise a replacement heart valve. The intralumenal frame assembly can be delivered transapically to a mitral valve location.

According to some embodiments, a delivery system can be used for controlled deployment of a prosthesis or replacement valve. The delivery system can comprise a delivery catheter, a prosthesis and a cover. The cover can be positioned over a plurality of first anchors of the prosthesis while the first anchors move from pointing in a first longitudinal direction to a second longitudinal direction, thereby preventing or limiting contact between the first anchors and tissue.

In some embodiments, the prosthesis or replacement valve can comprise a radially compacted replacement valve having a longitudinal axis positioned within the delivery catheter and comprising a plurality of first anchors wherein the first anchors each have an end pointing in a first longitudinal direction in the radially compacted state and the end is configured to change direction to point in a second longitudinal direction, the ends pointing in the second longitudinal direction after the replacement valve is deployed from the delivery catheter.

In some embodiments, a delivery system can be used for controlled deployment of a replacement valve. The delivery system can comprise a sheath and an expandable cover. The sheath can be configured to surround a radially compacted replacement valve, wherein retraction of the sheath from off of the radially compacted replacement valve allows the radially compacted replacement valve to at least partially expand. The expandable cover can be advanceable over the sheath prior to retraction to allow for expansion of the replacement valve within the expandable cover as the sheath is retracted to prevent or limit contact between the expanding replacement valve and tissue.

In certain embodiments, a replacement valve can comprise a plurality of anchors that are configured to change direction during expansion. Each of the anchors can have an end, the end pointing in a first direction prior to expansion and in a second direction after at least partial expansion. Each anchor can rotate at least 45 degrees during the partial expansion.

The delivery device can be used in a number of different methods, for example, a method of delivery of a replacement valve. A method can comprise: advancing a delivery system holding a radially compacted replacement valve to a native valve, the delivery system comprising: a sheath surrounding the radially compacted replacement valve; and an expandable cover; withdrawing the sheath to allow the replacement valve to at least partially expand within the expandable cover to prevent or limit contact between the expanding replacement valve and tissue.

In certain embodiments, advancing can further comprise advancing the delivery system to the native valve transapically. An additional step can be advancing the expandable cover over the sheath.

According to certain embodiments, a method of delivery of a replacement valve can comprise: advancing a delivery system holding a radially compacted replacement valve to a native valve, the delivery system having a longitudinal axis; at least partially expanding the replacement valve radially outward from the longitudinal axis and within an expandable cover to prevent or limit contact between the expanding replacement valve and tissue.

At least partially expanding the replacement valve can comprise allowing a plurality of anchors to self-expand within the expandable cover. Allowing the plurality of anchors to self-expand can comprise flipping an end of each of the anchors of the plurality of anchors to change a longitudinal orientation of the end from a first longitudinal direction to a second opposite longitudinal direction.

A delivery system can be used for controlled deployment of a prosthesis. In some embodiments, the delivery system can include an elongate inner member, an inner retention mechanism on the elongate inner member, and a shaft assembly. The inner retention mechanism can be configured to engage the prosthesis. The shaft assembly can be slidable over the elongate inner member and the inner retention mechanism. The shaft assembly can comprise an outer retention member, a first member and a second member. The outer retention member, together with the inner retention mechanism can be configured to secure the prosthesis on the delivery system. The first and second members can both be connected to the outer retention member and can facilitate delivery of the prosthesis with stretch and compression resistance while retaining the prosthesis during delivery through tortuous pathways.

In accordance with some embodiments a delivery system can comprise an elongate inner member and a shaft assembly configured to be slidable over the elongate inner member. The shaft assembly can be configured to at least partially radially constrain an expandable prosthesis when the expandable prosthesis is provided over the elongate inner member, and the shaft assembly can comprise a compression member and a tension member concentrically arranged.

In some embodiments, the compression member can surround the tension member. The delivery system can comprise an outer sheath configured to be slidable over the shaft assembly. The outer sheath can be configured to cover a distal end of the expandable prosthesis when the expandable prosthesis is provided over the elongate inner member. The outer sheath can comprise a slotted hypo tube. The slotted hypo tube can be configured to surround the compression member and the tension member when the outer sheath covers the distal end of the expandable prosthesis. At least a segment of the outer sheath can be formed of ePTFE.

In some embodiments, a flexible delivery system can comprise an elongate inner member, an inner retention mechanism on the elongate inner member, a mid shaft assembly, and an outer sheath. The delivery system can comprise a handle. The inner retention mechanism can be configured to engage a radially compacted proximal end of a replacement mitral valve. The mid shaft assembly can be configured to be slidable over the elongate inner member and the inner retention mechanism. The mid shaft assembly can comprise an outer retention member configured to cover at least the radially compacted proximal end of the replacement mitral valve when the proximal end of the replacement mitral valve is engaged with the inner retention mechanism, a first member having a distal end connected to the outer retention member, and a second member having a distal end connected to the outer retention member and extending along the length of the first member. The outer sheath can be configured to be slidable over the mid shaft assembly and configured to cover the distal end of the replacement mitral valve. The first member and second member can be positioned between the handle and the outer retention member.

In some embodiments, a delivery system can be configured to retain at least a radially compacted proximal end of a replacement mitral valve between an inner retention mechanism and an outer retention member during advancement of the delivery system within the body and the first and second members facilitate advancement with stretch and compression resistance through long and tortuous pathways.

In some embodiments, the first member can comprise a compression member. The first member can comprise a coiled spring. The second member can comprise a tension member. The second member can comprise a braided wire. The elongate inner member can comprise a tube having a lumen sized and configured to slidably accommodate a guidewire. The delivery system can comprise a nose cone connected to the distal end of the elongate inner member. The inner retention mechanism can comprise a ring comprising a plurality of teeth configured to engage tabs on the proximal end of the prosthesis. The outer retention member can be a ring.

In some embodiments, the delivery system can comprise a replacement mitral valve having a proximal end and a distal end. The proximal end of the replacement mitral valve can be engaged with the inner retention mechanism on the elongate inner member and can be covered by the outer retention member. The distal end of the replacement mitral valve can be covered by the outer sheath. The outer sheath can comprise a slotted hypo tube. The mid shaft assembly can comprise a plastic tube, wherein both the compression member and the tension member can be connected to the plastic tube. The plastic tube can be positioned between the handle and the compression and tension members.

BRIEF DESCRIPTION OF THE DRAWINGS

These and other features, aspects and advantages are described below with reference to the drawings, which are intended to illustrate but not to limit the invention.

FIGS. 14-23 illustrate steps of a deployment method using the delivery system of FIG. 9.

FIGS. 40A-B illustrate another embodiment of a delivery system.

DETAILED DESCRIPTION

The present specification and drawings provide aspects and features of the disclosure in the context of several embodiments of replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery device, etc. should not be taken as limiting, and features of any one embodiment discussed herein can be combined with features of other embodiments as desired and when appropriate. While certain of the embodiments described herein are described in connection with a transapical delivery approach, and certain of the embodiments described herein are described in connection with a transfemoral delivery approach, it should be understood that these embodiments can be used for other delivery approaches. Moreover, it should be understood that certain of the features described in connection with some embodiments can be incorporated with other embodiments, including those which are described in connection with different delivery approaches.

Figure 1:
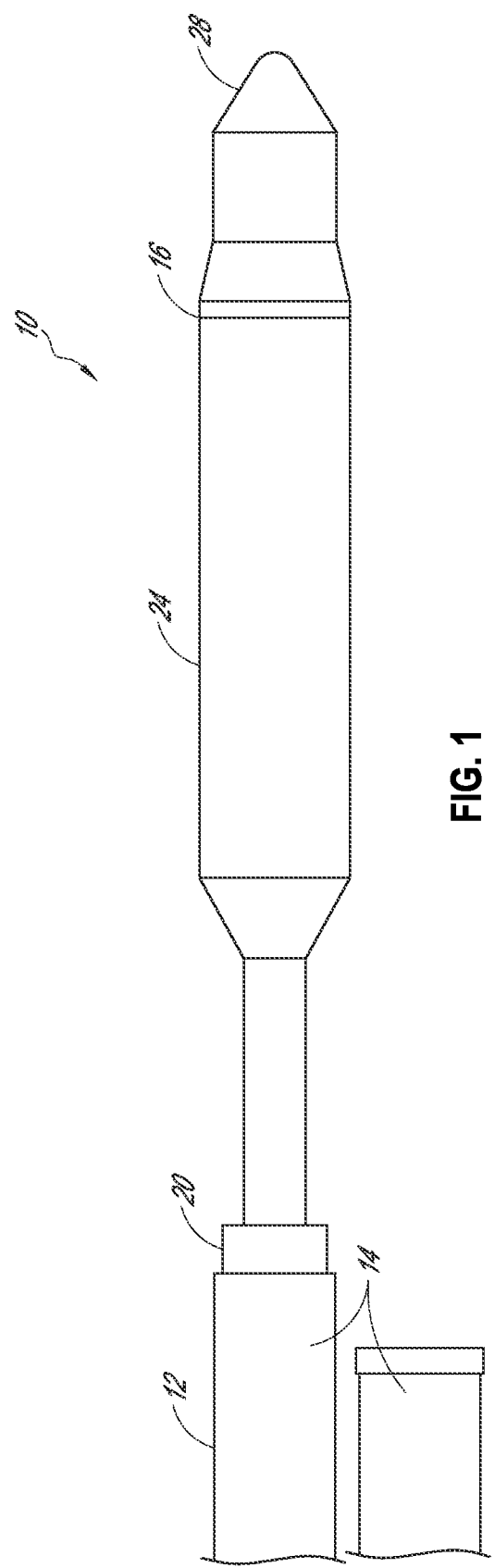
FIG. 1 shows an embodiment of a delivery system.

With reference to FIG. 1, an embodiment of a delivery device or system 10 is shown. The delivery system can be used deploy a prosthesis, such as a replacement heart valve, within the body. Replacement heart valves can be delivered to a patient's heart mitral valve annulus in various ways, such as by open surgery, minimally-invasive surgery, and percutaneous or transcatheter delivery through the patient's vasculature. The delivery device 10 can be relatively short to more easily be used in an open heart procedure or other more direct procedures than the percutaneous procedure starting at the leg. At the same time, the delivery device 10 can still be relatively flexible to allow, for example, advancement through the pulmonary veins or the wall of the left atrium and then bending of the delivery device for proper placement at the mitral valve. In this way the illustrated embodiment comprises an elongate, delivery system configured to be advanced in a transapical delivery approach.

The delivery system 10 can include an elongate shaft assembly 12 comprising a proximal end and a distal end, wherein a handle (not shown) is coupled to the proximal end of the assembly 12. The elongate shaft assembly 12 can be used to hold the prosthesis for advancement of the same through the vasculature to a treatment location. The elongate shaft assembly 12 can include an implant retention area 16 that can be used for this purpose. In some embodiments, the elongate shaft assembly 12 can hold an expandable prosthesis in a compressed state at implant retention area 16 for advancement of the prosthesis within the body. The elongate shaft assembly 12 may then be used to allow controlled expansion of the prosthesis at the treatment location. The implant retention area 16 is shown at the distal end of the delivery device, but may also be at other locations.

The elongate shaft assembly 12 can include one or more subassemblies as will be described in more detail below. The elongate shaft assembly 12 can be configured to deliver a prosthesis positioned within the implant retention area 16 to a treatment location. One or more of the subassemblies can then be moved to allow the prosthesis to be released at the treatment location. For example, one or more of the subassemblies may be movable with respect to one or more of the other subassemblies. The handle can include various control mechanisms that be used to control the movement of the various subassemblies. In this way, the prosthesis can be controllably loaded onto the delivery device 10 and then later deployed within the body.

With continued reference to FIG. 1, it can be seen that the subassemblies of the elongate shaft assembly 12 can include one or more outer sheaths 14, a cover 20, a capsule 24, and a nose cone 28. An implant in a pre-deployed state can be held by the delivery device within the capsule and the nose cone. The capsule and nose cone can be made of polyurethane for atraumatic entry and to minimize injury to tissue. The nose cone or other parts can also be radiopaque to provide for visibility under fluoroscopy.

The implant or prosthesis can take any number of different forms. A particular example of frame for a prosthesis is shown herein, though it will be understood that other designs can also be used. Additional example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, the entirety of these patents and publications are hereby incorporated by reference and made a part of this specification.

Each of the subassemblies can be made of or attached to tubes that slide within one another. In this way, each of the outer sheaths 14, cover 20, capsule 24, and/or nose cone 28 may move with respect to one or more of the other components or subassemblies. The innermost assembly may include a lumen sized and configured to slidably accommodate a guidewire so that the delivery device 10 can be advanced over the guidewire.

The various tubes can be a hypodermic tube or hypo tube. The tube can be made from one of any number of different materials including nitinol, stainless steel, and medical grade plastics. The tube can be a single piece tube or multiple pieces connected together. Using a tube made of multiple pieces can allow the tube to provide different characteristics along different sections of the tube, such as rigidity and flexibility. For example, in some embodiments it can be desirable, and/or needful, for the delivery device 10 to have greater flexibility at the distal end of the device, where flexibility is not as necessary for the proximal end.

Figure 2:
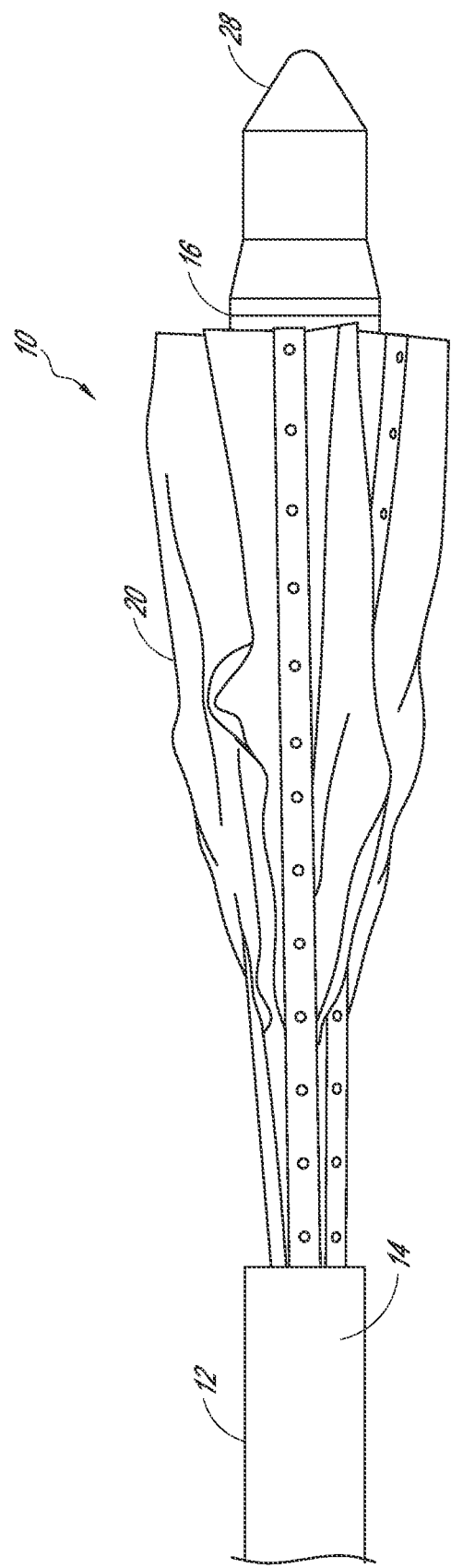
FIGS. 2-4 illustrates steps of a deployment method using the delivery system of FIG. 1.

Moving now to FIG. 2, it can be seen that the cover 20 can be advanced over the capsule 24. The cover 20 can be used to allow the implant to expand while reducing and/or preventing contact between the implant and body tissue during all or part of the expansion process. The cover 20 can be made of a plurality of longitudinal struts sufficiently rigid to advance over the capsule after the delivery device has been positioned within the body at or near a treatment location. For example, the delivery device can be advanced into the left ventricle of the heart for a mitral valve replacement and the cover can then be advanced over the capsule prior to expanding all or part of the implant. The cover can also include a film, sheet, fabric, or other material that can be positioned between the struts. This sheet may or may not be flexible. The sheet can initially be folded within an outer sheath and can expand to a larger size after advancing over the capsule. It will also be understood that in other embodiments, the cover can be positioned over the capsule in an initial state, or prior to advancing the delivery device to the treatment area.

Figure 3:
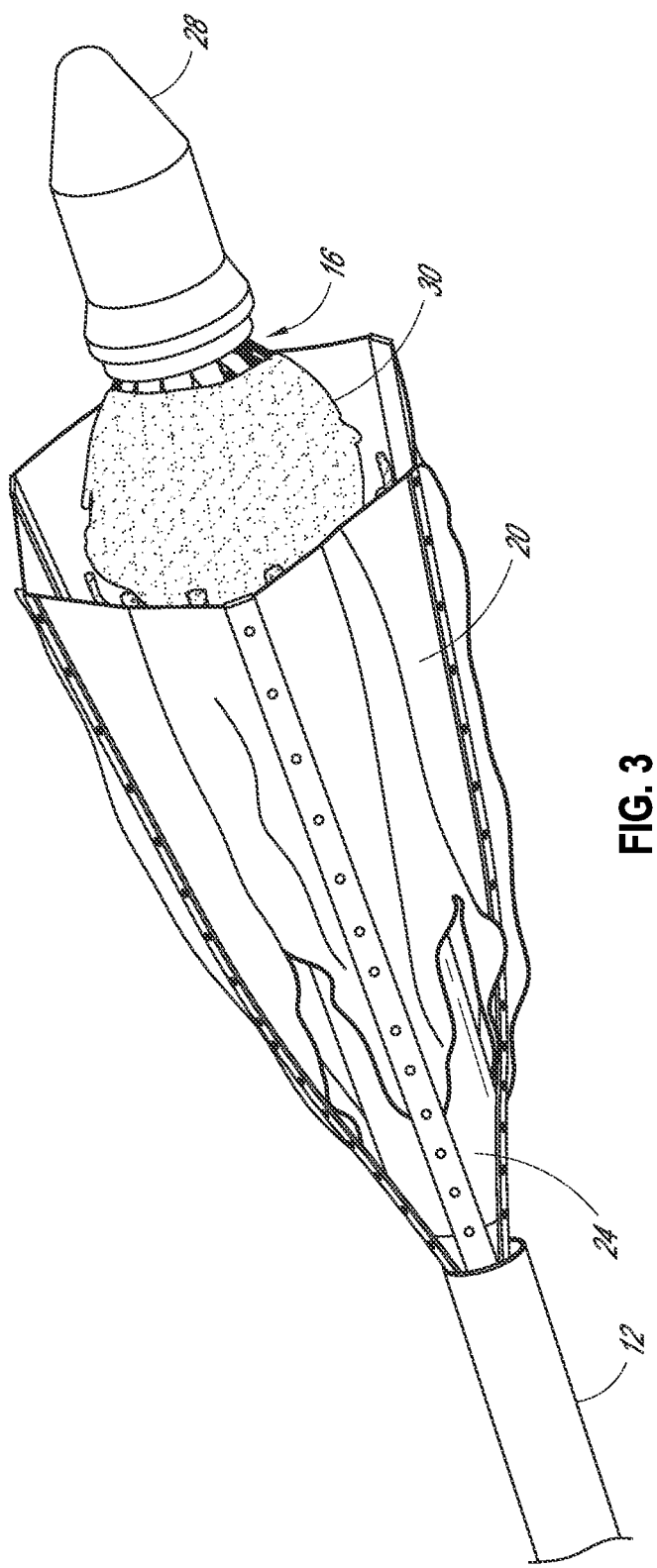
Figure 4:
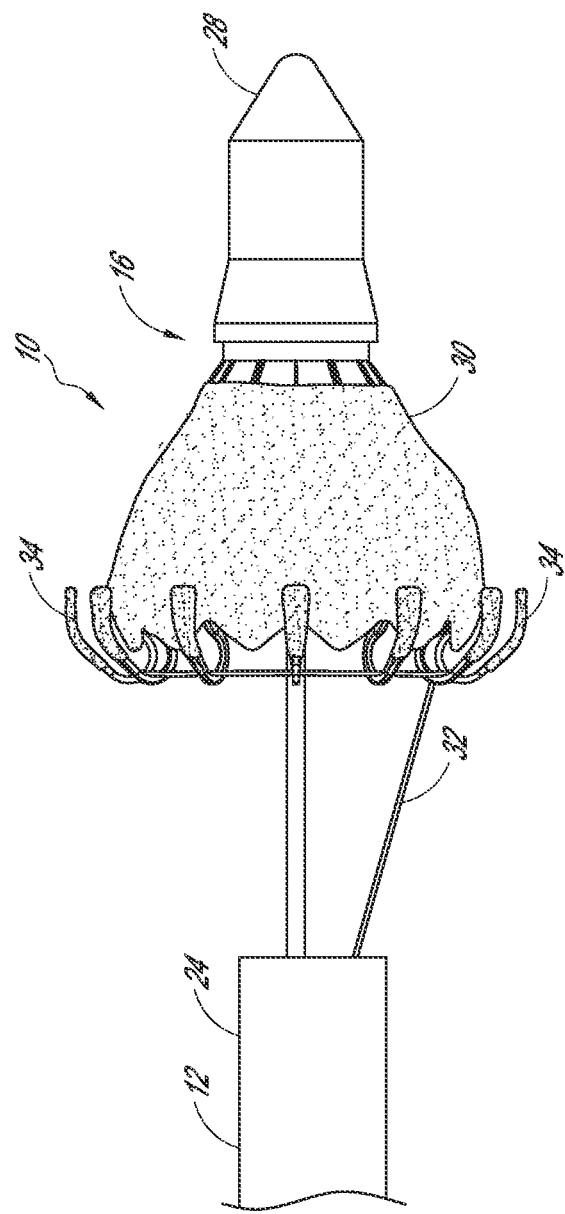
Figure 5:
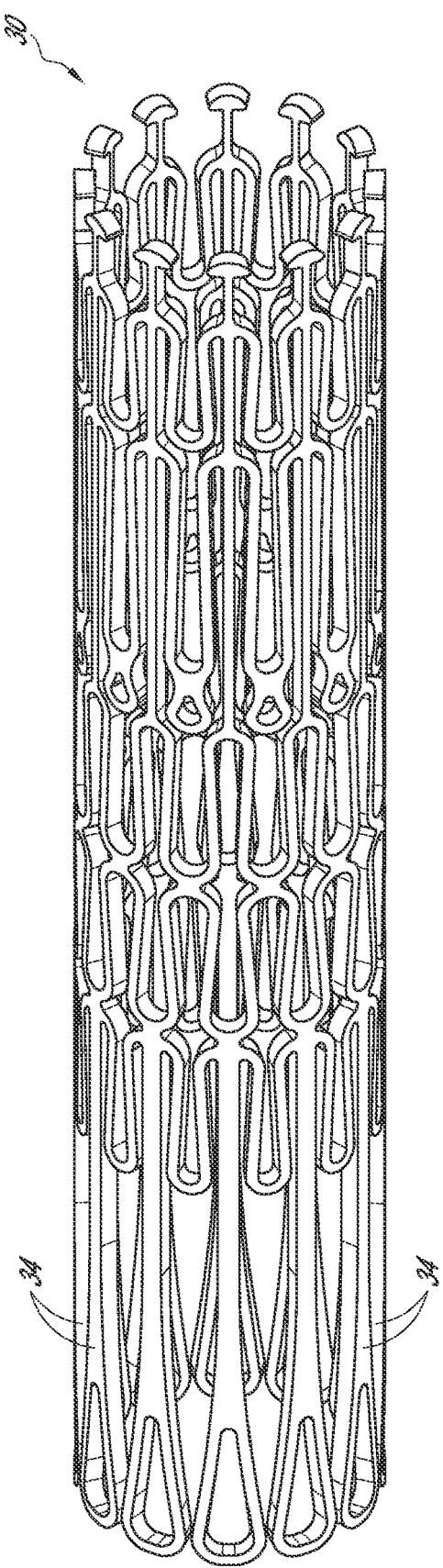
FIGS. 5 and 6 show a perspective and side view of an embodiment of a prosthesis in a pre-expanded state.
Figure 6:
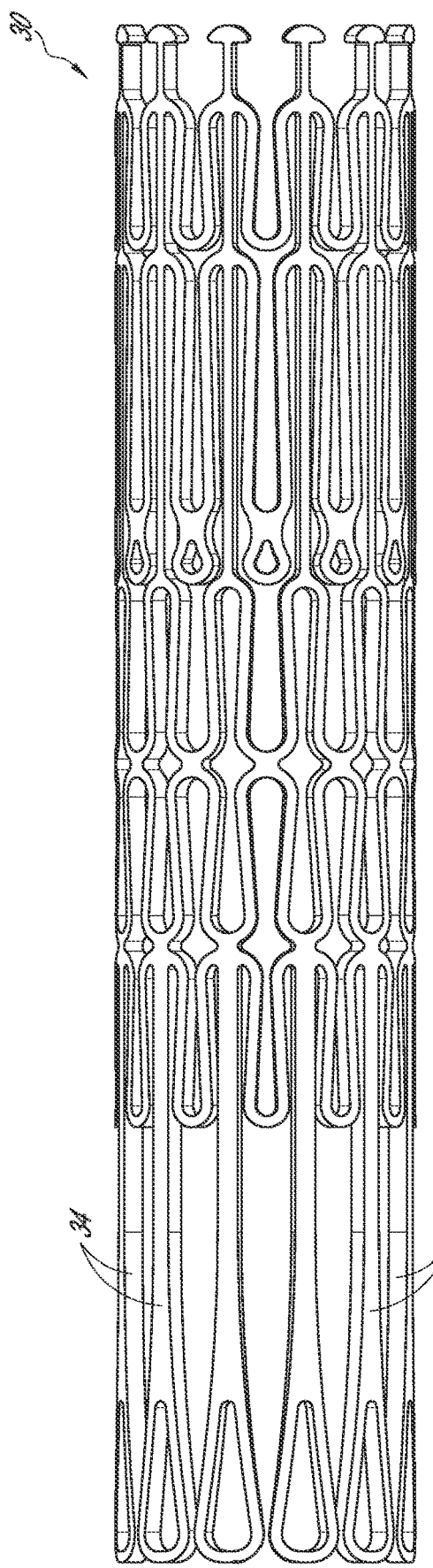

Once the cover is in position, or while the cover is being advanced into position, the capsule 24 can be withdrawn or otherwise removed from covering the implant 30. Removing the capsule can allow the implant to expand, partially or in full. In some embodiments, a separate device can control all or part of the expansion of the implant. FIG. 3 shows the cover 20 over the implant 30 and the capsule 24 withdrawn. Withdrawing the capsule can also assist the cover in expanding so as not to impede or restrict expansion of the implant. With the implant partially or fully expanded, the cover can then be withdrawn. FIG. 4 shows the delivery device after the cover has been withdrawn, with the implant partially expanded. FIG. 4 also shows a tether, wire or suture 32 that can be used to at least partially control expansion of the implant. Also, an end portion of the implant remains compacted in the nose cone 28. This can allow the implant to be positioned at a heart location prior to full expansion.

FIG. 4 also illustrates that the implant 30 has a plurality of anchors 34. In some embodiments, the anchors 34 can point in a first direction prior to expansion and then rotate to point in a second, longitudinally opposite direction after expansion. The anchors can completely flip directions. The cover 20 can beneficially ensure that the anchors do not engage or get caught in tissue during rotation. For example, without a cover during deployment in the left ventricle of the heart, the anchors can easily get caught in the chordae tendineae as they rotate or change directions. FIG. 4 further illustrates that the tether, wire or suture 32 may extend from within the capsule 24 and wrap around the implant 30, for example at the base of the anchors 34. The tether, wire or suture 32 may thus partial control expansion of the implant by radially restraining expansion of the implant as the anchors 34 are released from the capsule 24.

FIGS. 5-8 illustrate an example implant 30 that can be used with the delivery device 10. It can be seen that the anchors 34 can point in a first direction prior to deployment when in the pre-deployment state of FIGS. 5-6. When deployed, the anchors can rotate to the position shown in FIGS. 7-8. It will be understood that the implant can be made of a self-expanding material so as to self-expand into the desired shape. The implant of FIGS. 5-6 can be cut from a tube to the shape shown and the expanded to the shape of FIGS. 7-8. The implant can then be compressed back to the shape shown in FIGS. 5-6 or to a similar shape. Further details of the implant are described in the patents and applications incorporated by reference above.

Figure 7:
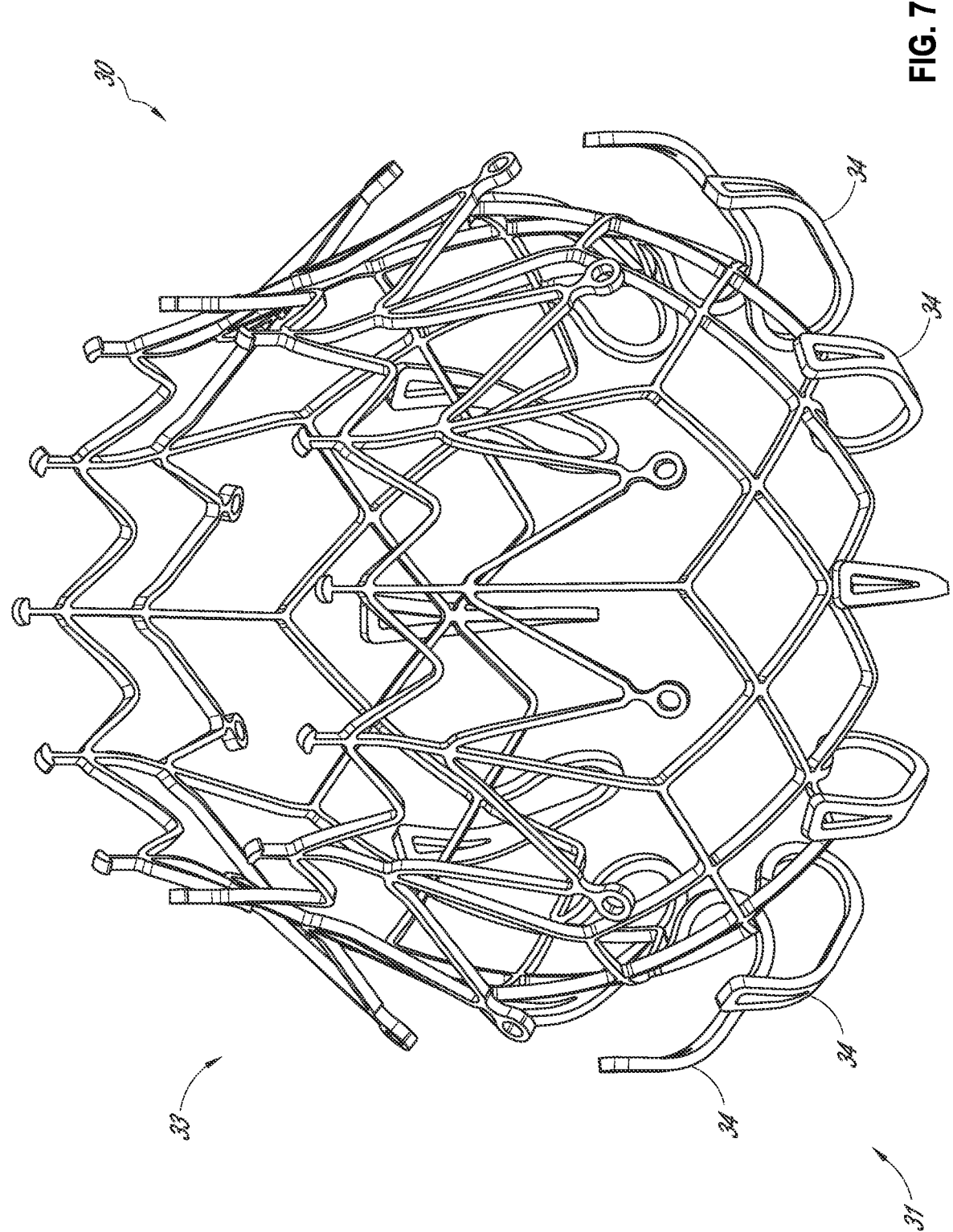
FIGS. 7 and 8 show a perspective and side view of the prosthesis in an expanded state.
Figure 8:
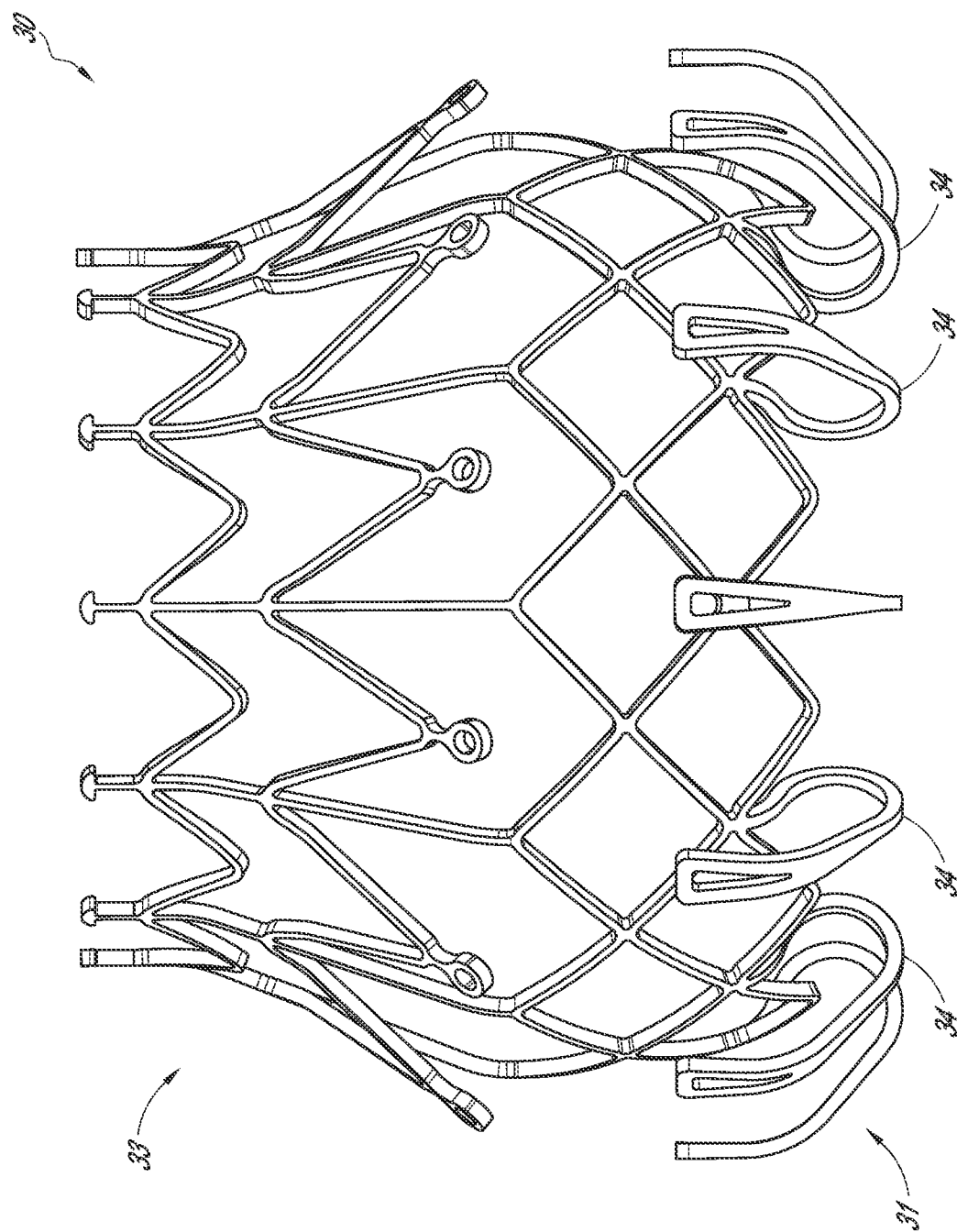

The embodiment of FIGS. 9-13 illustrates a delivery device or system 100. Delivery system 100 can have components, features, and/or functionality similar to those described with respect to delivery device or system 10. The delivery system 100 can be used to deploy a prosthesis, such as a replacement heart valve as described elsewhere in this specification, within the body. The delivery system 100 can receive and/or cover portions of the prosthesis such as a first end and second end of the prosthesis. For example, the delivery system 100 may be used to deliver a prosthesis 30 such as illustrated in FIGS. 7 and 8, where the prosthesis includes a first end 33 and a second end 31, and wherein the second end 31 is configured to be deployed before the first end 33. Replacement heart valves can be delivered to a patient's heart mitral valve annulus or other heart valve location in various ways, such as by open surgery, minimally-invasive surgery, and percutaneous or transcatheter delivery through the patient's vasculature. The delivery system 100 can be relatively short to more easily be used in an open heart procedure or other more direct procedures than the percutaneous procedure starting at the leg. At the same time, the delivery system 100 can still be relatively flexible to allow, for example, advancement through the pulmonary veins or the wall of the left atrium and then bending of the delivery device for proper placement at the mitral valve. In some embodiments, the delivery system 100 is particularly suitable for delivering a replacement heart valve to a mitral valve location through a transapical approach (e.g., through the apex of the heart).

Figure 9:
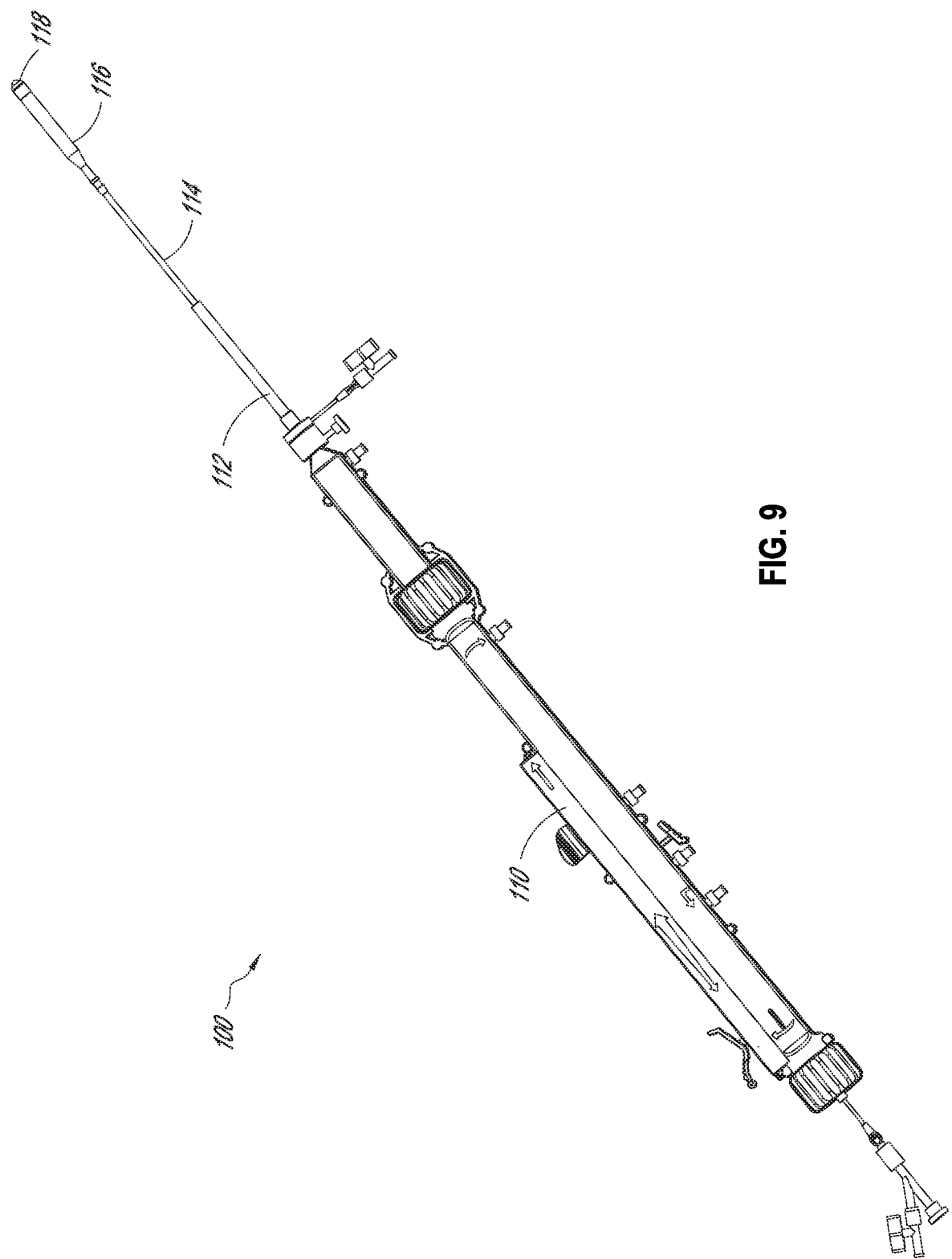
FIG. 9 shows another embodiment of a delivery system.
Figure 10:
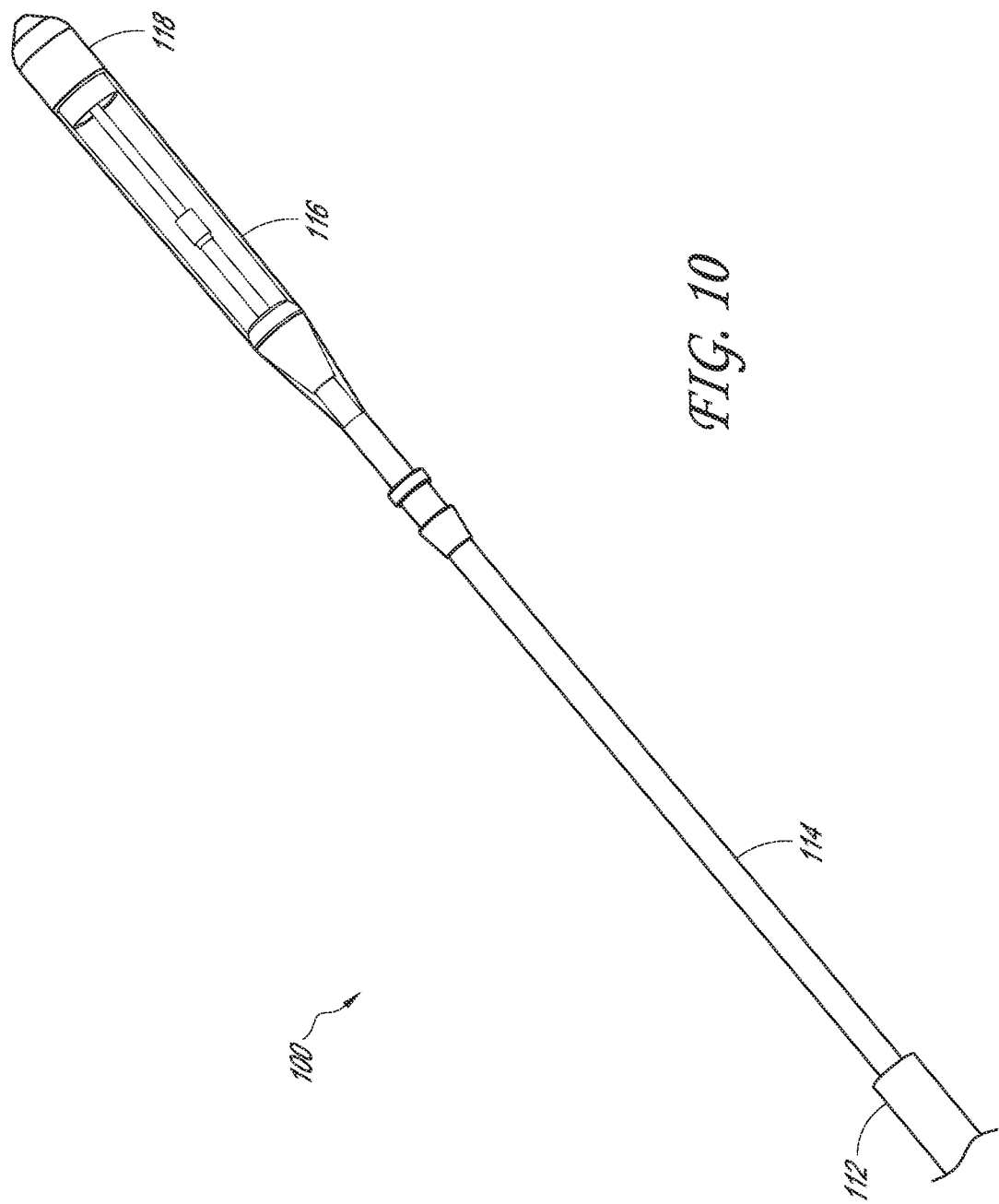
FIG. 10 shows a close-up in view of components of the delivery system of FIG. 9.

With reference first to the embodiment of FIGS. 9 and 10, the delivery system 100 can include a handle 110 and a plurality of sheaths and/or shafts such as the illustrated introducer sheath 112 and outer elongate hollow member shaft 114. As will be described in further detail below, the plurality of shafts can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 100. In some embodiments, the handle 110 can include a plurality of switches, levers, or other actuatable mechanisms which can be used to control the movement of the one or more shafts of the delivery system 100 and/or to control the operation of other components of the delivery system 100.

With continued reference to the embodiment of FIGS. 9 and 10, the delivery system 100 can include an introducer sheath 112 and an outer elongate hollow member shaft 114, each having a proximal and distal end. As used to describe the components of the delivery system, "proximal" refers to a location of the component that is closer to the handle 110, and "distal" refers to a location of the component that is further from the handle 110. In some embodiments, the proximal end of the introducer sheath 112 can be coupled to the handle 110. The introducer sheath 112 can be sized and shaped such that introducer sheath 112 is slidable over the outer elongate hollow member shaft 114. For example, in some embodiments, the introducer sheath 112 can be fixed relative to the handle 110 and the outer elongate hollow member shaft 114 can be moved within the introducer sheath 112. In some embodiments, the introducer sheath 112 can be movable relative to the handle 110. As should be understood from the above disclosure, in some embodiments, the introducer sheath 112 can be omitted and the outer elongate hollow member shaft 114 can form the outer shaft of the delivery system 100. For example, the embodiment of FIGS. 25 and 26 illustrates a delivery system 200 without an introducer sheath 112 and the outer elongate hollow member shaft 214 forming an outer shaft.

With continued reference to the embodiment of FIGS. 9 and 10, the outer elongate hollow member shaft 114 can optionally have a distal end coupled to a proximal end of an outer elongate hollow member 116. The outer elongate hollow member 116 can be a sheath or capsule similar to capsule 24 described in connection with delivery system 10. In some embodiments, the outer elongate hollow member shaft 114 and/or the outer elongate hollow member 116 can cover at least a portion of the prosthesis while the prosthesis is being delivered to the deployment site. For example, the outer elongate hollow member shaft 114 and/or the outer elongate hollow member 116 can cover at least the second end 31 of the prosthesis while the first end 33 of the prosthesis is received within nose cone 118. In some embodiments, the outer elongate hollow member 116 can also cover the first end of the prosthesis. The outer elongate hollow member 116 can be sized and shaped such that the elongate hollow member 116 can retain the prosthesis in a compressed state as it is delivered to the deployment site. Accordingly, the outer elongate hollow member shaft 114 can function as a capsule shaft. Optionally, the anchors 34 on the prosthesis may extend proximally toward the handle 110 when the prosthesis is covered by the outer elongate hollow member. The outer elongate hollow member 116 can be moveable relative to the nose cone 118 to uncover the second end of the prosthesis while the first end of the prosthesis remains engaged to an inner retention member (described with respect to FIG. 13 below) within the nose cone 118 and remains covered by the nose cone 118.

As shown in the illustrated embodiment, the outer elongate hollow member 116 includes a taper at a proximal end such that the proximal end of the outer elongate hollow member 116 has an outer diameter which is less than an outer diameter of the distal end of the outer elongate hollow member 116. In some embodiments, the outer diameter of the proximal end of the outer elongate hollow member 116 can be similar to, or equal to, the outer diameter of a distal end of the outer elongate hollow member shaft 114. In some embodiments, the outer elongate hollow member 116 can be collapsible such that, upon retraction towards the introducer sheath 112, the outer elongate hollow member 116 can collapse into the introducer sheath 112. The outer elongate hollow member 116 can be formed from a variety of materials, including ePTFE, as well as other biocompatible materials.

Figure 25:
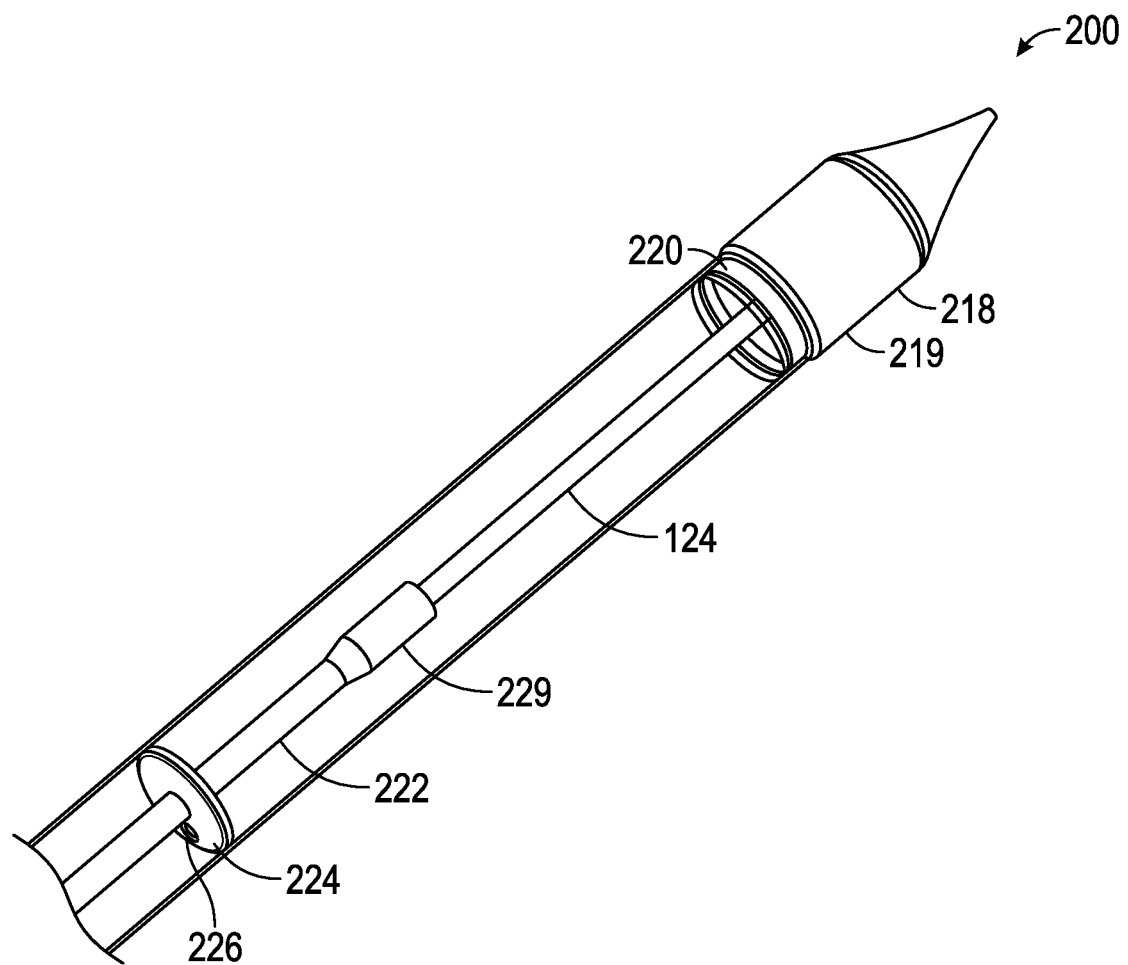
FIG. 25 shows another embodiment of a delivery system.
Figure 26:
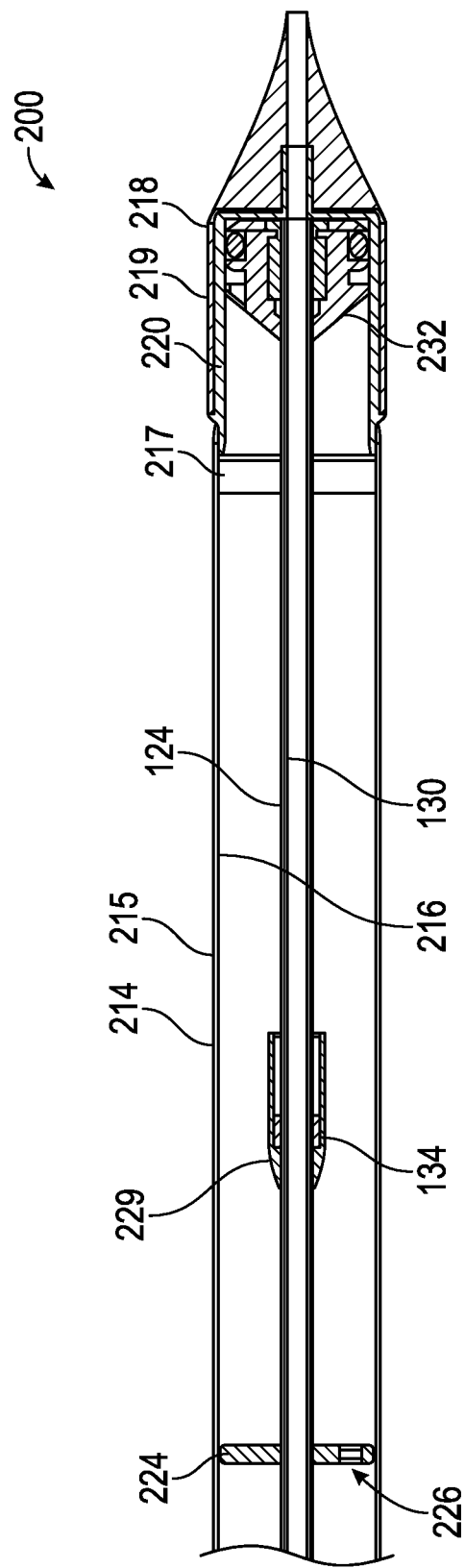
FIG. 26 shows a cross-sectional view of the delivery system of FIG. 25.

With reference to the embodiment of FIGS. 25 and 26, in some embodiments, the outer elongate hollow member shaft 214 can extend over the prosthesis and can be sized and shaped such that it can retain the prosthesis in a compressed state as it is delivered to the deployment site. As shown in the illustrated embodiment, the outer elongate hollow member shaft 214 can have a constant or substantially constant outer diameter throughout the entirety, or a substantial portion of the entirety, of its length.

As shown more clearly in FIG. 26, the outer elongate hollow member shaft 214 can have a taper at its distal end. The outer elongate hollow member shaft can include a marker 217 positioned proximate the distal end. In some embodiments, the outer elongate hollow member shaft 214 can include a first portion 215 and a second portion 216. This can advantageously allow for the use of two types of material for the outer elongate hollow member shaft 214. For example, as shown in the illustrated embodiment, at least a portion of the first portion 215 can be positioned radially outward from of the second portion 216 relative to a longitudinal axis of the outer elongate hollow member shaft 214. The first portion 215 can be formed from a relatively rigid material, such as PEBAX, ULTEM, PEAK and any other biocompatible material as desired. This can advantageously provide some degree of rigidity for the outer elongate hollow member shaft 214. The second portion 216 can be formed from a more compliant material, such as PTFE, ePTFE and any other biocompatible material as desired. This can advantageously provide a more compliant inner surface for the outer elongate hollow member shaft 214, which can be beneficial when contacting other components of the delivery system 200 and the prosthesis. In some embodiments, the second portion 216 can be a liner which is applied to the first portion 215.

While the illustrated outer elongate hollow member shaft 214 is shown with multiple portions formed from multiple materials, it is also contemplated that the outer elongate hollow member shaft 214 can be a formed from a single material. Moreover, in some embodiments, the outer elongate hollow member shaft 214 can include an elongate hollow member similar to outer elongate hollow member 116 which can cover at least a portion of the prosthesis. In some embodiments, the outer elongate hollow member can have a constant or substantially constant outer diameter throughout the entirety, or a substantial portion of the entirety, of its length. The outer diameter of the outer elongate hollow member can be similar to, or equal to, the outer diameter of the outer elongate hollow member shaft 214. In some embodiments, the outer elongate hollow member can be formed from a material different from the outer elongate hollow member shaft 214.

Figure 11:
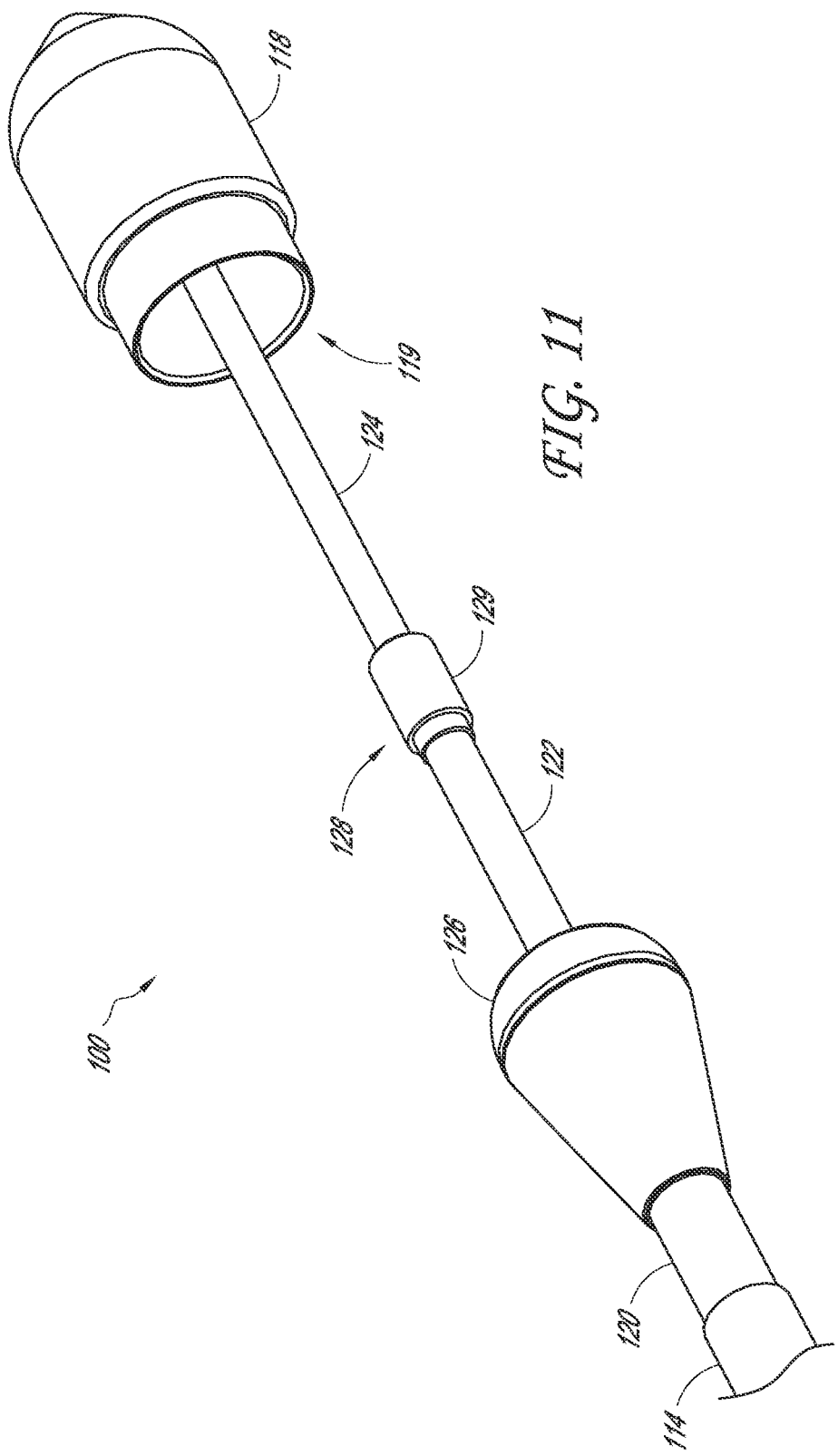
FIGS. 11 and 12 show components of the delivery system of FIG. 9 with certain components having been omitted.
Figure 12:
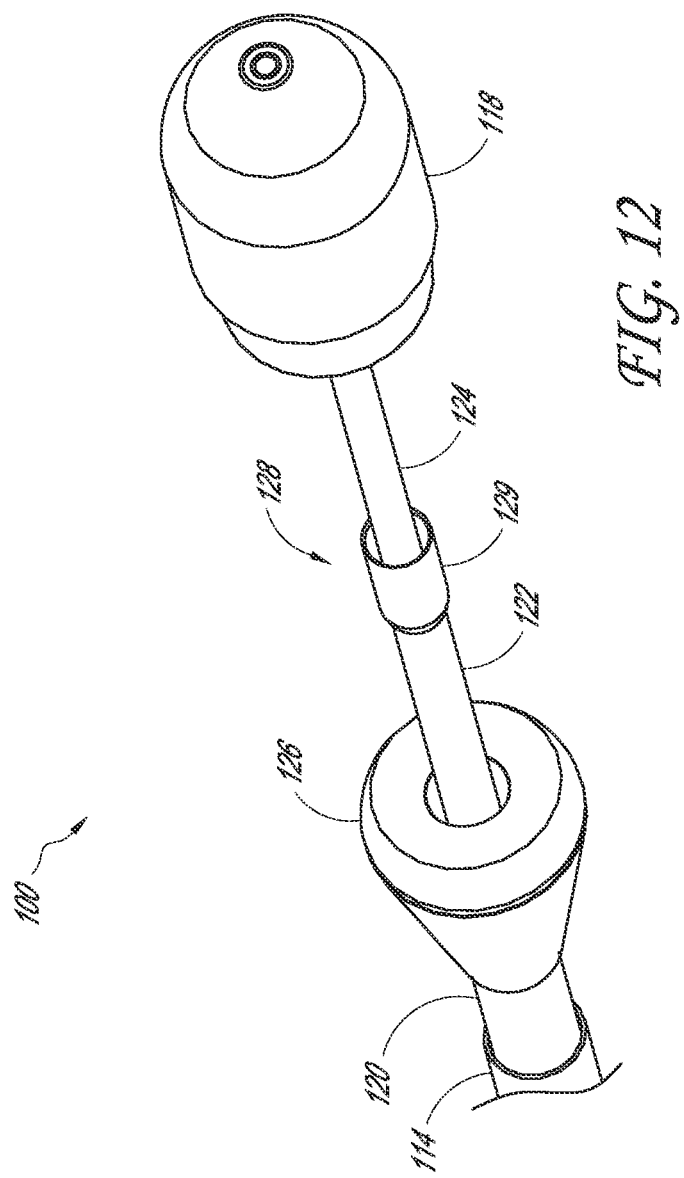

With reference now to the embodiment of FIGS. 11 and 12, which illustrates delivery system 100 without the outer elongate hollow member 116 being shown, the delivery system 100 can include a plug shaft 120, a locking shaft 122, and an inner retention shaft 124, each having a proximal and distal end. The distal end of plug shaft 120 can be coupled to the proximal end of a plug 126. In some embodiments, plug shaft 120 can be sized and shaped such that plug shaft 120 is slidable over the locking shaft 122. For example, in some embodiments, the locking shaft 122 can be moved within the plug shaft 120. In some embodiments, the plug shaft 120 can be moved over the locking shaft 122. Moreover, plug shaft 120 can be sized and shaped such that the outer elongate hollow member shaft 114 is slidable over the plug shaft 120. In some embodiments, the plug 126 can be used to engage the nose cone when the nose cone is retrieved from the patient. For example, the plug 126 can be used to contact the proximal end of the nose cone 118 as the nose cone 118 is retracted proximally toward the plug 126 or as the plug 126 is advanced distally toward the nose cone 118. As should be understood from the above disclosure, in some embodiments, the plug shaft 120 and/or the plug 126 can be omitted from the delivery system 100. For example, the embodiment of FIGS. 25 and 26 illustrates a delivery system 200 without a plug shaft 120 or plug 126.

With reference back to the embodiment of FIGS. 11 and 12, the nose cone 118 can have a tapered distal end. The nose cone 118 can be formed from a relatively rigid, high durometer material such as a metal. The nose cone 118 can have a length, measured from the distalmost end to a proximalmost end, of between approximately 5 mm to 50 mm, between approximately 10 mm to approximately 40 mm, between approximately 15 mm to approximately 25 mm, approximately 20 mm, any other lengths within these ranges, and any other lengths as desired.

In some embodiments such as that of FIGS. 25 and 26, the nose cone 218 can have a more elongated shape. As shown in the illustrated embodiment, the tapered portion can be concave thereby forming a more defined distal tip of the nose cone 218. As shown more clearly in FIG. 26, the nose cone 218 can include a first portion 219 and a second portion 220. This can advantageously allow for the use of two types of material for the nose cone 218. For example, as shown in the illustrated embodiment, at least a portion of the first portion 219 can be positioned radially outward from of the second portion 220 relative to a longitudinal axis of the nose cone 218. The first portion 219 can be formed from a lower durometer material such as urethane, PEBAX, polysilicone and any other biocompatible material as desired. The second portion 220 can be formed from higher durometer materials such as stainless steels, titanium, and any other biocompatible material as desired. This can advantageously provide additional structural support for the nose cone 218. In some embodiments, the second portion 220 can include threading for attachment to a shaft, such as nose cone shaft 130. In some embodiments, the first portion 219 can be overmolded onto the second portion 220 and/or attached using mechanical fasteners such as screws, bolts, rivets, and threaded couplings, chemical fasteners, such as adhesives, or other types of fastening techniques such as welding. In some embodiments, the nose cone 218 can be a single unit formed from a single material.

With reference particularly to the embodiment of FIG. 26, the outer diameter of the nose cone 218, such as the first portion 219 and/or second portion 220, can be similar to, or equal to, the outer diameter of an outer shaft and/or outer component, such as the outer elongate hollow member shaft 214. As shown in the illustrated embodiment, the first portion 219 has an outer diameter which is similar to that of the outer elongate hollow member shaft 214. This can form a generally smooth transition in diameter between the nose cone 218 and the outer shaft and/or the outer component if and when the nose cone 218 is brought into contact with the outer shaft and/or the outer component. In some embodiments, the nose cone 218 can have an outer diameter of approximately 31 Fr or 32 Fr and the outer shaft and/or outer component can have an outer diameter of approximately 31 Fr or 32 Fr.

In some embodiments, the outer diameter of the nose cone 218, such as the first portion 219 and/or second portion 220, can be similar to, or equal to, the inner diameter of an outer shaft and/or outer component such that the first portion 219 and/or the second portion 220 can be partially received within the outer shaft and/or outer component. In some embodiments, the nose cone 218 can have an outer diameter of approximately 30 Fr and the outer shaft and/or outer component can have an inner diameter of approximately 30 Fr. In some embodiments, the outer shaft can be an outermost shaft of the delivery system.

With reference back to the embodiment of FIGS. 11 and 12, the distal end of locking shaft 122 can be coupled to at least a portion of a tether retention assembly 128. As shown in the illustrated embodiment, the locking shaft 122 is coupled to a lock 129 of the tether retention assembly 128. Lock 129 can function as a sheath of the tether retention assembly 128. The lock 129 can be used to cover a corresponding component of the tether retention assembly 128 such as a tether retention member 134, not shown in FIGS. 11 and 12 but which will be described in further detail below with respect to FIG. 13. In some embodiments, locking shaft 122 can be sized and shaped such that locking shaft 122 is slidable over the inner retention shaft 124. For example, in some embodiments, the inner retention shaft 124 can be moved within the locking shaft 122. In some embodiments, the locking shaft 122 can be moved over the inner retention shaft 124. The locking shaft 122 can cooperate with the tether retention assembly 128 to release a tether 136 (shown in FIG. 13) attached to the prosthesis. For example, proximal movement of locking shaft 122 can result in proximal movement of the lock 129 relative to the tether retention member thereby releasing a tether engaged to the tether retention assembly 128. Moreover, locking shaft 122 can be sized and shaped such that the outer elongate hollow member shaft 114 is slidable over the locking shaft 122.

Figure 13:
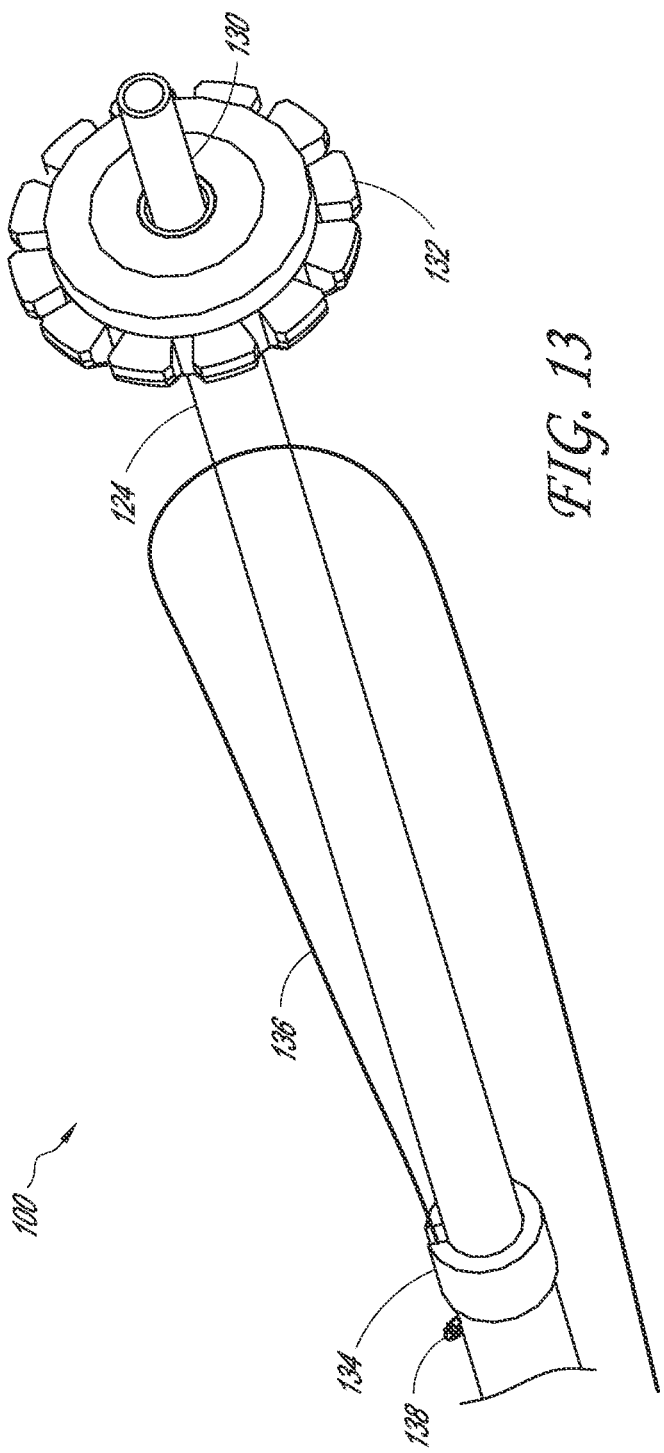
FIG. 13 shows further components of the delivery system of FIG. 9 with additional components having been omitted.

With continued reference to the embodiment of FIGS. 11 and 12, the distal end of the inner retention shaft 124 can be coupled to at least a portion of an inner retention member 132 that is positioned within nose cone 118 (not shown in FIGS. 11 and 12, but shown in FIG. 13). In some embodiments, inner retention shaft 124 can be sized and shaped such that inner retention shaft 124 is slidable within the locking shaft 122. For example, in some embodiments, the inner retention shaft 124 can be moved within the locking shaft 122. In some embodiments, the locking shaft 122 can be moved over the inner retention shaft 124. The inner retention shaft 124 can cooperate with the inner retention member 132 and the nose cone 118 to release a first end of the prosthesis from the nose cone 118. In some embodiments, the first end of the prosthesis can be received within a proximally-facing opening 119 (see FIG. 11) and covered by the nose cone 118. The first end of the prosthesis can also be engaged with the inner retention member 132. Accordingly, proximal movement of the inner retention shaft 124 can result in proximal movement of the inner retention member relative to the nose cone 118 which can release the first end of the prosthesis from the nose cone 118. Similarly, distal movement of the nose cone 118 relative to the inner retention shaft 124, and thus the inner retention member, can also release the first end of the prosthesis from the nose cone 118.

In some embodiments such as that of FIG. 26, the inner locking shaft 222 can include a radial protrusion 224, such as an annular disc, and a lock 229 similar to lock 129. The radial protrusion 224 can assist in maintaining the locking shaft 222 in a desired radial alignment relative to the shaft within which the locking shaft 222 is positioned. For example, as shown in the illustrated embodiment, the radial protrusion can assist in maintaining concentricity between the locking shaft 222 and another shaft such as the outer elongate hollow member shaft 214 in embodiments without a plug shaft 120 and/or plug 126. In some embodiments, the locking shaft 222 can include a guide member 226 for the tether, wire or suture 32. As shown in the illustrated embodiment, the guide member can be formed as a hole on the radial protrusion.

In some embodiments, the locking shaft 222 can be retracted via use of a spring loaded actuator. The spring loaded actuator can be similar to spring 1066 described in connection with FIG. 36C.

With reference now to the embodiment of FIG. 13, which illustrates delivery system 100 without the outer elongate hollow member 116, nose cone 118, locking shaft 122, and lock 129 being shown, the delivery system 100 can include a nose cone shaft 130 having a proximal and distal end. The distal end of the nose cone shaft 130 can be coupled to a portion of the nose cone 118. In some embodiments, nose cone shaft 130 can be sized and shaped such that inner retention shaft 124 is slidable over the nose cone shaft 130. For example, in some embodiments, the nose cone shaft 130 can be moved within the inner retention shaft 124. In some embodiments, the inner retention shaft 124 can be moved over the nose cone shaft 130. Moreover, in some embodiments, the nose cone shaft 130 can be hollow such that the nose cone shaft 130 can receive a guidewire.

With continued reference to the embodiment of FIG. 13, the delivery system 100 can include an inner retention member 132 such as an inner retention ring coupled to the distal end of the inner retention shaft 124. The inner retention member 132 can include a plurality of slots sized and shaped to receive portions of a first end of the prosthesis. In some embodiments, the slots can extend radially inward. The first end of the prosthesis can be placed in a compressed state such that the first end of the prosthesis is retained between the inner retention member 132 and the nose cone (not shown) when the inner retention member 132 is received within and covered by the nose cone. In some embodiments, when the inner retention member 132 is uncovered, the first end of the prosthesis can expand radially outward from the inner retention member 132 and thereby disengage from the inner retention member 132.

Figure 27:
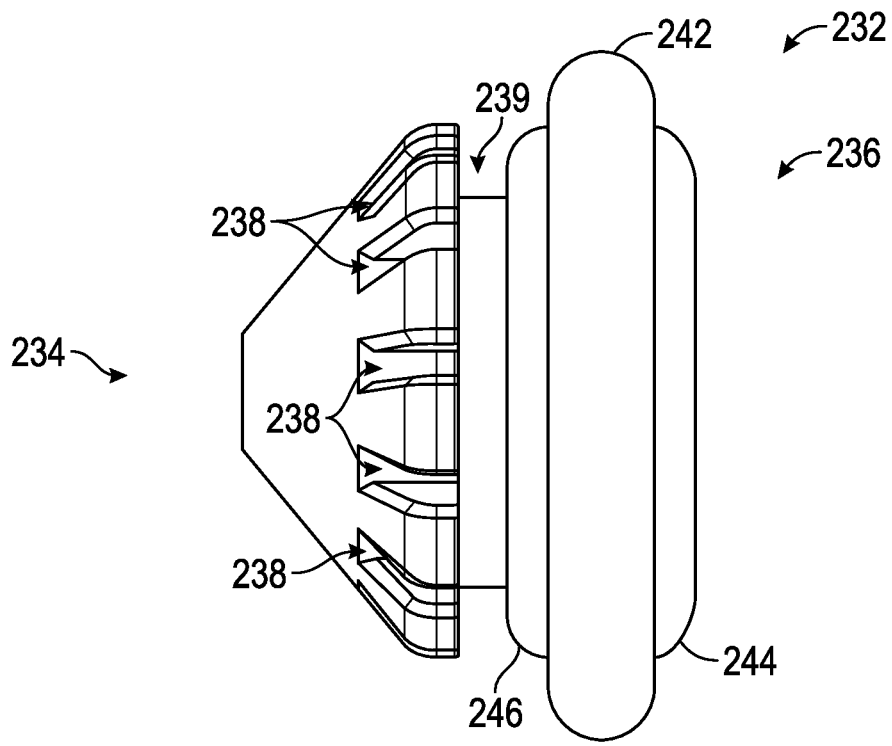
FIG. 27 shows another embodiment of an inner retention mechanism.
Figure 28:
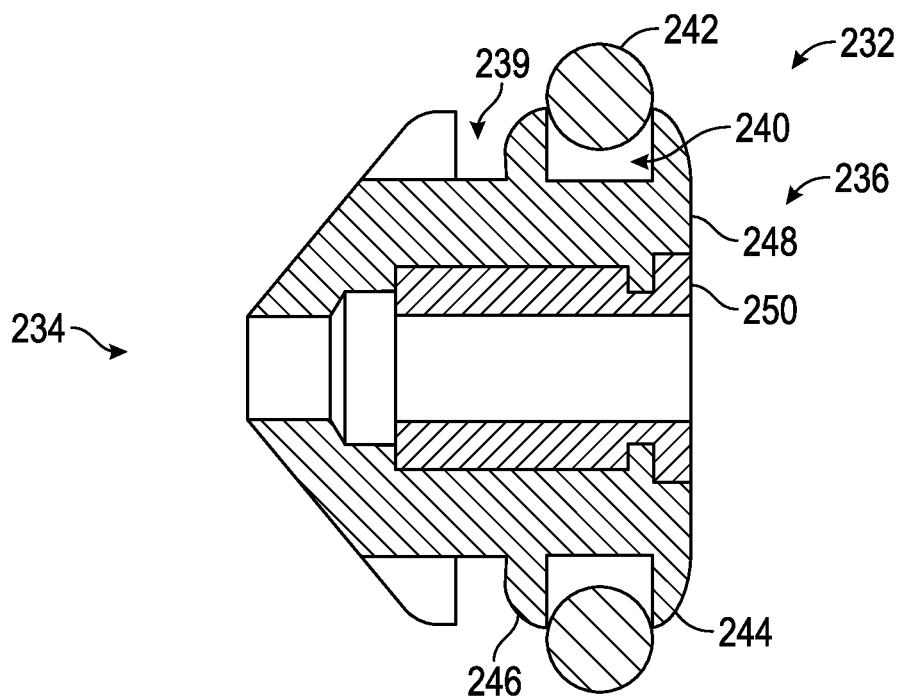
FIG. 28 shows a cross-sectional view of the inner retention mechanism of FIG. 27.

In some embodiments such as that of FIGS. 27 and 28, the inner retention member 232 can have a more elongated design. As shown in the illustrated embodiment, the inner retention member 232 can have a proximal end 234 and a distal end 236 with a plurality of slots 238 sized and shaped to receive portions of a first end of the prosthesis positioned proximate the proximal end 234. Slots 238 can extend along a longitudinal axis of the inner retention member 232. In some embodiments, the inner retention member 232 can include a cavity 239 positioned distal the slots 238. The cavity 239 can be sized and shaped to receive portions of the first end of the prosthesis. As shown in the illustrated embodiment, the cavity 239 can have an annular shape. In some embodiments, the inner retention member 232 can include a taper towards the proximal end 234. This can facilitate removal of the inner retention member 232 from the heart by reducing the diameter at the proximalmost end of the inner retention member 232 and reducing the likelihood of snagging on tissue. This can be particularly advantageous in embodiments where the plug shaft 120 and/or plug 126 are not included in the delivery system 100.

As shown in the illustrated embodiment, the inner retention member 232 can include a cavity 240 proximate the distal end 236. The cavity 240 can be formed between one or more radial protrusions, such as ridges 244, 246. A compressible member 242, such as an O-ring, can be received at least partially within the cavity 240. As shown in the illustrated embodiment, the cavity 240 can have an annular shape.

With continued reference to the embodiment of FIG. 28, in some embodiments the inner retention member 232 can include a first portion 248 and a second portion 250. This can advantageously allow for the use of two types of material for the inner retention member 232. For example, as shown in the illustrated embodiment, at least a portion of the first portion 248 can be positioned radially outward from of the second portion 250 relative to a longitudinal axis of the inner retention member 232. The first portion 248 can be formed from materials such as urethane, PEBAX, polysilicone and any other biocompatible material as desired. The second portion 250 can be formed from higher durometer materials such as stainless steels, titanium, and any other biocompatible material as desired. In some embodiments, the second portion 250 can include threading for attachment to a shaft, such as inner retention shaft 124. This can advantageously provide additional structural support for the inner retention member 232. In some embodiments, the first portion 248 can be overmolded onto the second portion 250 and/or attached using mechanical fasteners such as screws, bolts, rivets, and threaded couplings, chemical fasteners, such as adhesives, or other types of fastening techniques such as welding. In some embodiments, the inner retention member 232 can be a single unit formed from a single material.

Figure 29:
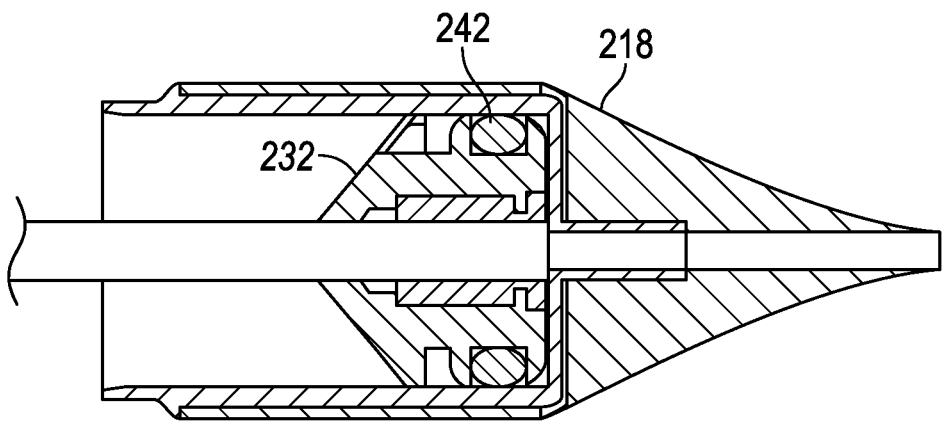
FIG. 29 shows a cross-sectional view of an embodiment of the inner retention mechanism and nose cone in a first configuration.
Figure 30:
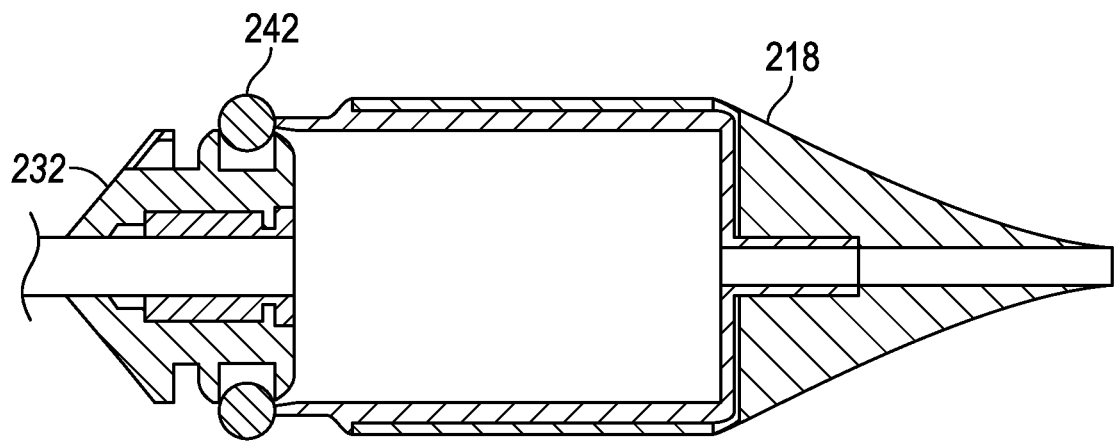
FIG. 30 shows a cross-sectional view of the inner retention mechanism and nose cone of FIG. 29 in a second configuration.

As shown in the embodiment of FIG. 29, in some embodiments the compressible member 242 can be sized and shaped such that it can be compressed to a smaller outer diameter. This can allow the compressible member 242 to fit within the nose cone, such as nose cones 118, 218, when the inner retention member 232 is positioned within the nose cone 218. In such an embodiment, positioning within the nose cone 218 can maintain the compressible member 242 in this compressed state. Once the compressible member 242 is no longer fully positioned within the nose cone 218, as shown in the embodiment of FIG. 30, the compressible member 242 can expand to a larger outer diameter. In some embodiments, the outer diameter in the relaxed or expanded state can be greater than the inner diameter of the nose cone 218. In some embodiments, the outer diameter in the relaxed or expanded state can be greater than the outer diameter of the nose cone 218. This can advantageously facilitate removal of the inner retention member 232 and nose cone 218 from the heart. For example, the compressible member can be positioned against a proximal edge of the nose cone 218 thereby serving as a smoother and less traumatic contact surface.

With reference back to the embodiment of FIG. 13, the delivery system 100 can include a tether retention member 134. The tether retention member 134 can be attached to the inner retention shaft 124. As shown in the illustrated embodiment, the tether retention member 134 can be a C-lock having an opening through which a tether 136 can pass. In order to retain the tether 136 within the tether retention member 134, the end 138 of the tether 136 can be sized and shaped such that the end 138 is prevented from passing through the opening of the tether retention member 134. For example, the end 138 of the tether 136 can be knotted such that at least one dimension of the end 138 prevents the end 138 from passing through the opening. In the illustrated embodiment, the tether 136 can be released from the tether retention member 134 by passing the tether 136 radially away from and over the tether retention member 134. The tether 136 can be tensioned and angled such that the tether 136 would pass over the tether retention member 134 when tether retention member 134 is uncovered from the lock 129 (not shown). It should be understood that other mechanisms can be used for tether retention assembly 128 in lieu of the lock and tether retention member 134 including, but not limited to, clamps which engage the tether 136. Although not shown, the tether 136 can engage at least a portion of the prosthesis, such as the second end of the prosthesis. For example, in some embodiments, the tether can wrap around at least some portion of the prosthesis and extend at least proximally through at least the outer elongate hollow member 116 and/or the outer elongate hollow member shaft 114. The end opposite end 138 can be attached to a component of the delivery system 100 such that the tether 136 can be retracted into the delivery system 100 upon release of the tether 136 from the tether retention assembly 128.

The embodiments of FIGS. 14-23 illustrate steps of a method of operating the delivery system 100 and releasing an intralumenal frame assembly, such as implant 30, to intralumenal tissue at an in situ target location. The steps of this method can be carried out while the intralumenal frame assembly is in a radially compacted state within an outer member, such as outer elongate hollow member 116. In some embodiments, the longitudinal axis of the frame assembly, which runs between the first and second ends of the intralumenal frame assembly, can be parallel to and/or concentric with the longitudinal axis of one or more shafts of the delivery system 100. The steps of this method can be used to transapically deliver a replacement heart valve to a mitral valve location.

Figure 14:
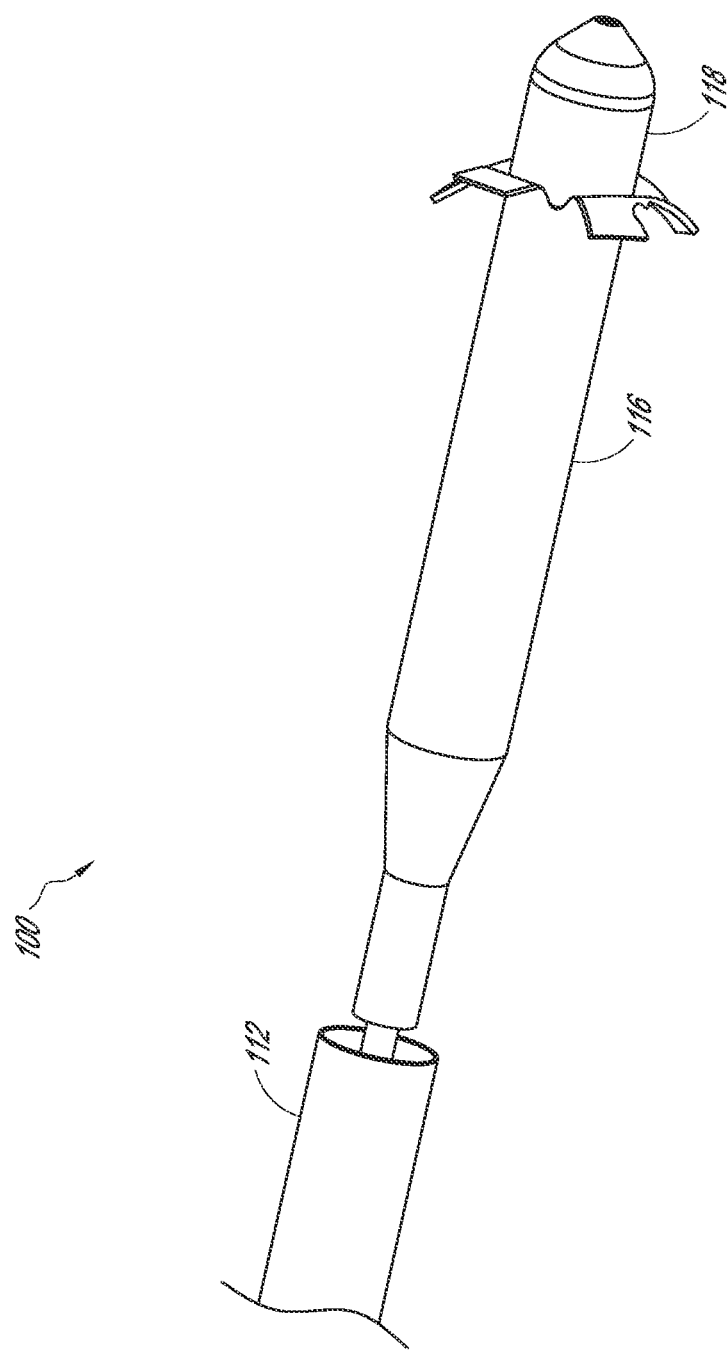

With reference first to the step of FIG. 14, the delivery system 100 is shown in a preliminary configuration with the outer elongate hollow member 116 covering the implant (not shown) and adjacent to the nose cone 118. In this configuration, the delivery system 100 has a relatively compact form factor which facilitates delivery of the implant to the in situ target location. As shown in the illustrated embodiment, the outer elongate hollow member 116 can remain wholly outside the introducer sheath 112 in this configuration.

Figure 15:
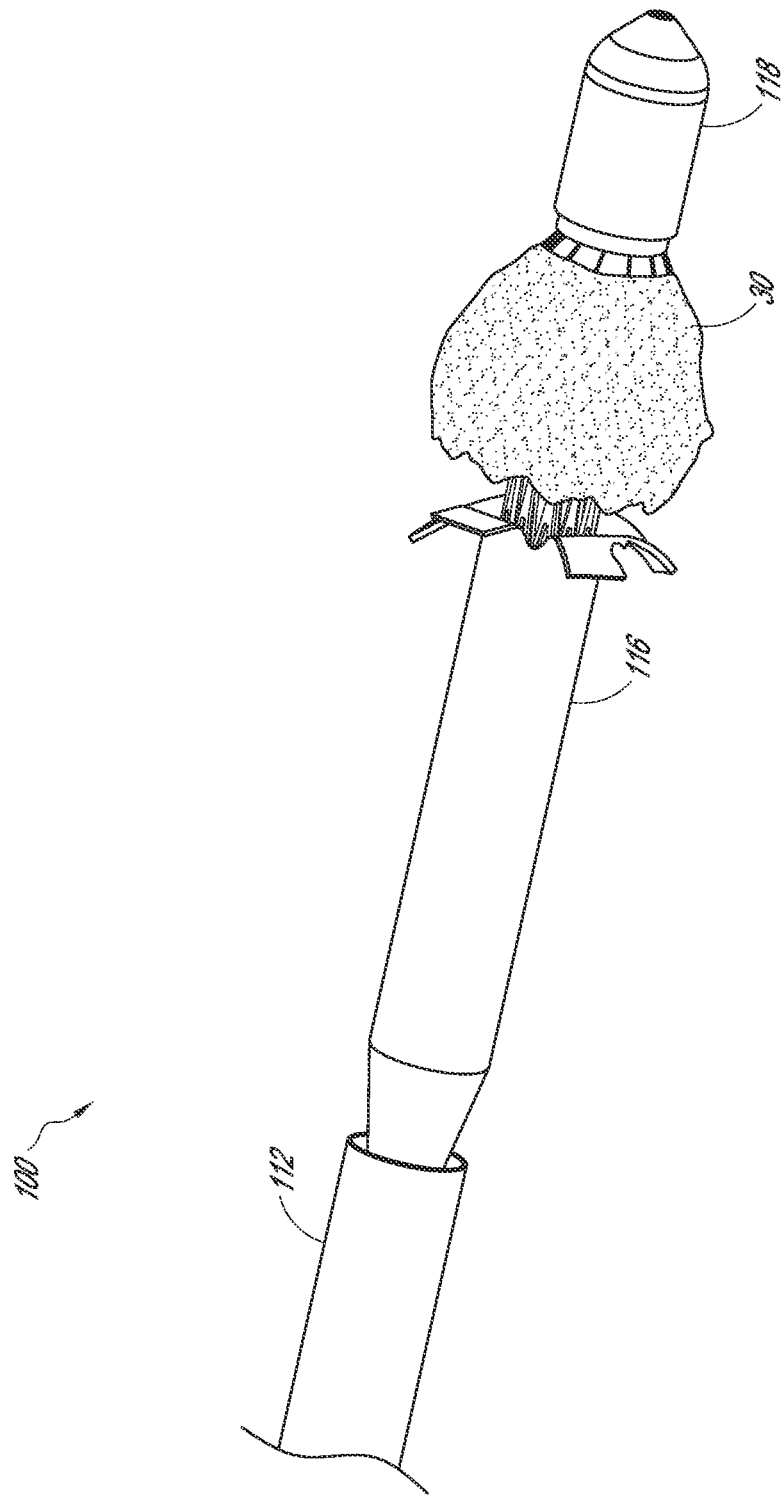

With reference next to the step of FIG. 15, once the delivery system 100 has positioned the implant at the in situ target location, the outer elongate hollow member 116 can be moved relatively away from the nose cone 118, either by proximally retracting the outer elongate hollow member 116 and/or distally advancing the nose cone 118, to uncover at least a portion of the implant 30. As shown in the illustrated embodiment, the outer elongate hollow member 116 can also be moved relatively toward the introducer sheath 112, either by proximally retracting the outer elongate hollow member 116 and/or distally advancing the introducer sheath 112, such that the outer elongate hollow member 116 is partially received within the introducer sheath 112.

Figure 16:
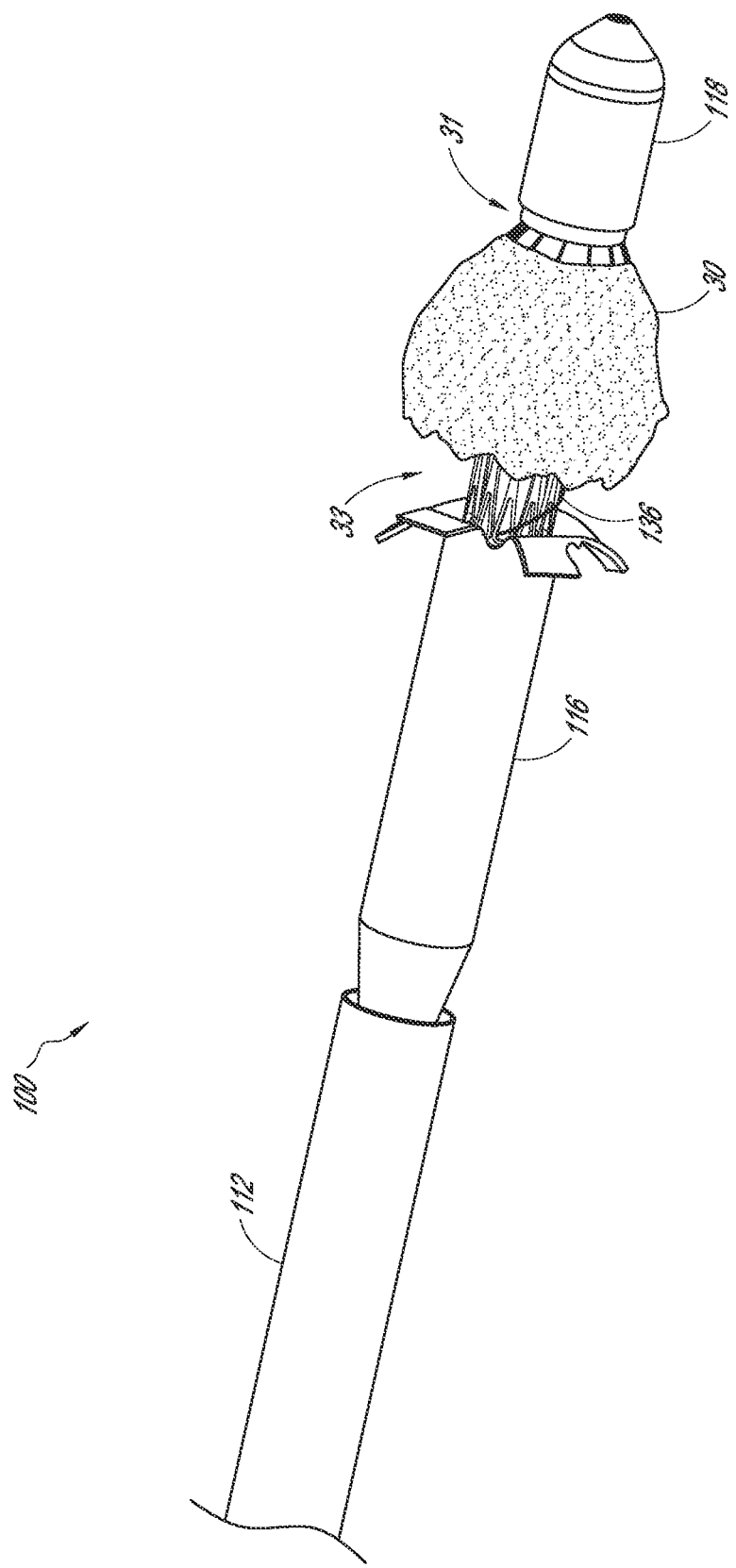

With reference next to the step of FIG. 16, the outer elongate hollow member 116 can be further moved relatively away from the nose cone 118 to further uncover the implant 30 and/or relatively toward the introducer sheath 112. As shown in the illustrated embodiment, the second end 31 of the implant 30 has been partially uncovered with both the outer elongate hollow member 116 and the tether 136 restraining the radial dimension of the frame of the implant 30. It should be noted that the first end 33 of the implant 30 can remain covered by the nose cone 118 during this step such that the first end 33 remains in a radially compacted state.

Figure 17:
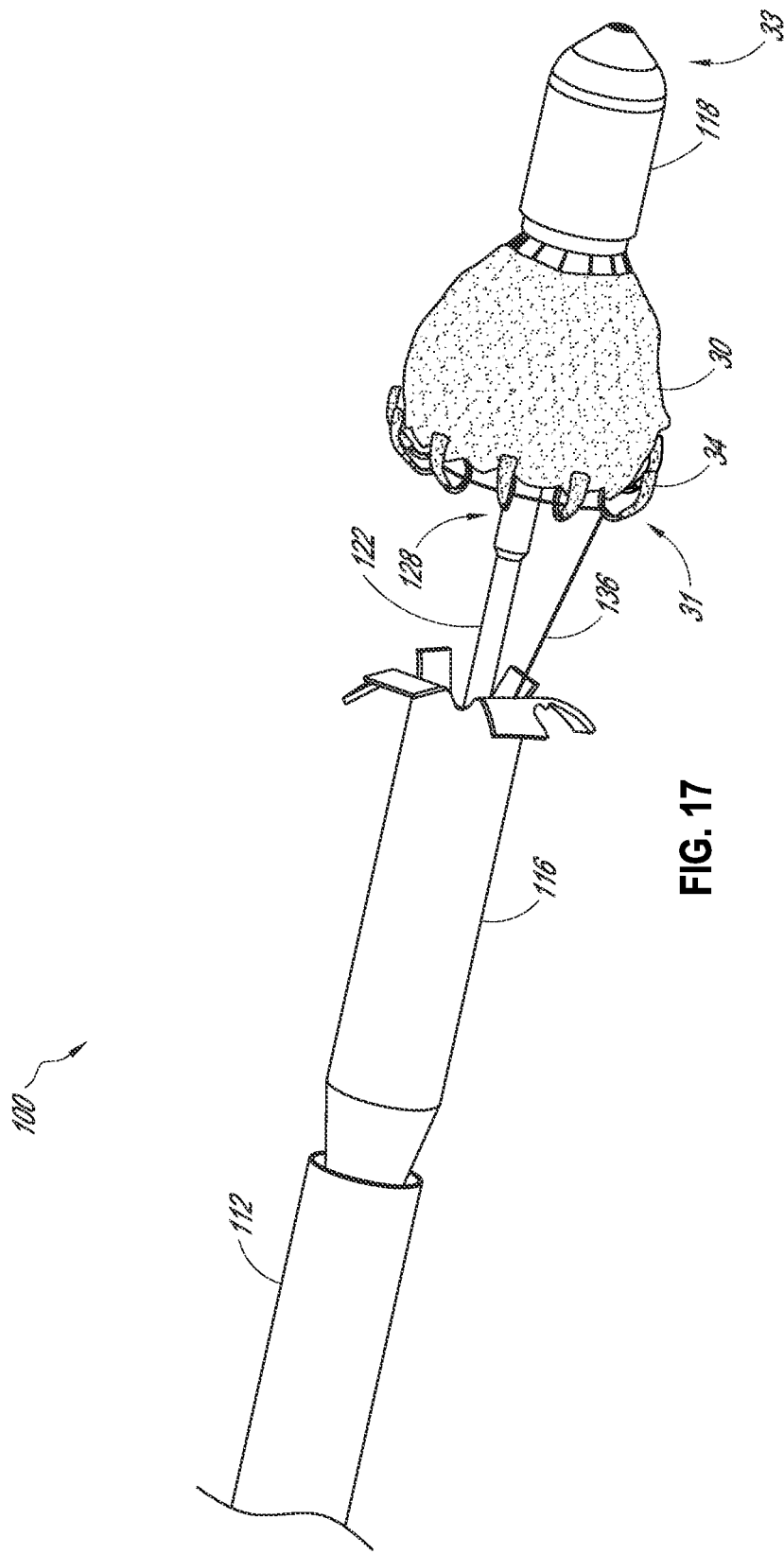

With reference next to the step of FIG. 17, the outer elongate hollow member 116 can be further moved relatively away from the nose cone 118 thereby further uncovering the implant 30 and/or relatively toward the introducer sheath 112. As shown in the illustrated embodiment, the second end 31 of the implant 30 has been fully uncovered. Moreover, as shown in the illustrated embodiment, the second end 31 of the implant 30 has at least partially expanded in the radial dimension with anchors 34 having been flipped to extend distally away from the second end 31 of the implant 30. The tether 136 can continue to at least partially restrain the radial dimension of the second end 31 and can advantageously reduce the speed at which the second end 31 radially expands. In some embodiments, the tether 136 can be designed such that the second end 31 remains in the fully compacted state when the second end 31 is fully uncovered. It should be noted that the end (not shown) of the tether 136 remains attached to the tether retention assembly 128. During this step, tension in the tether 136 can be reduced such that the second end 31 of the implant 30 can be further radially expanded.

Figure 18:
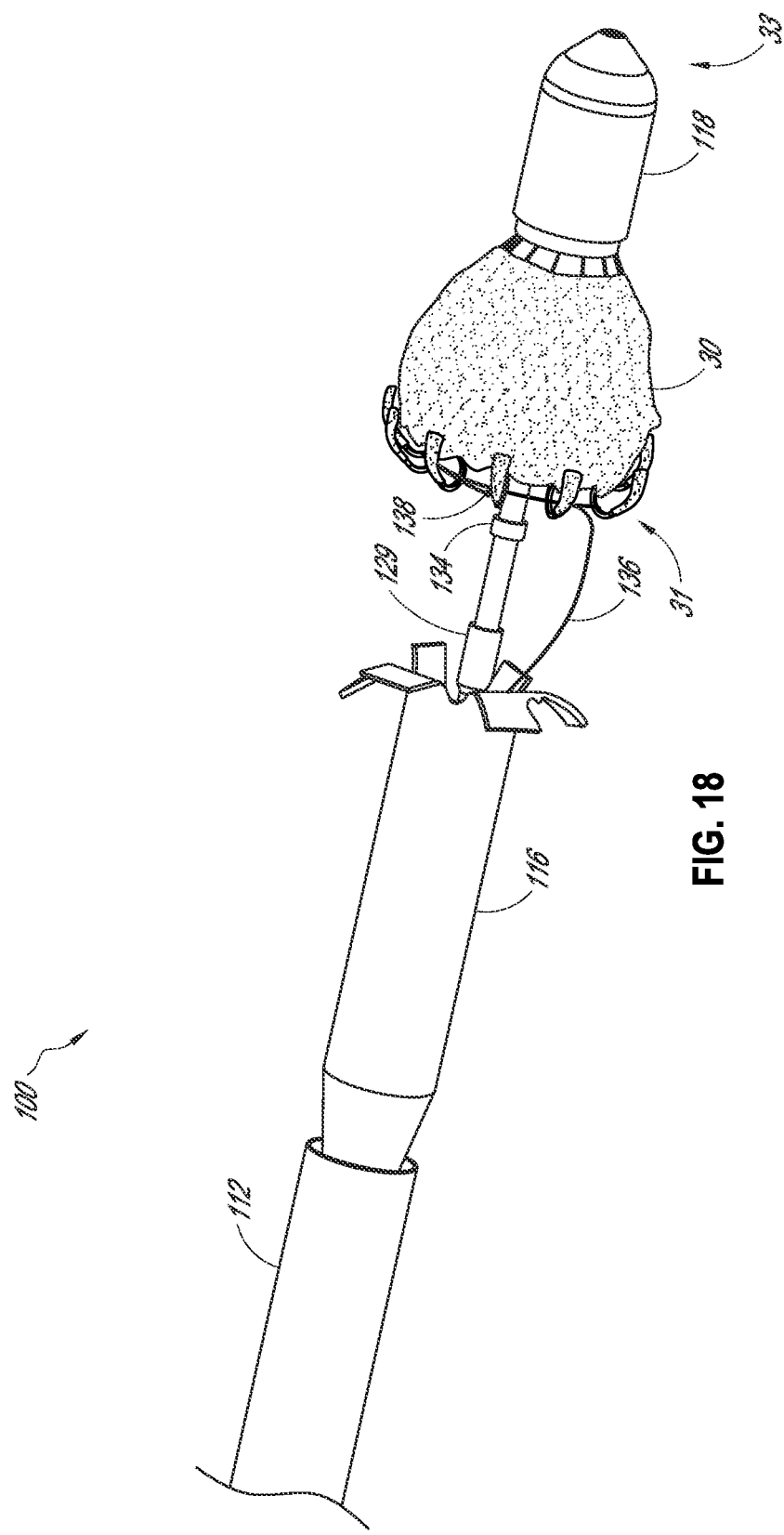
Figure 19:
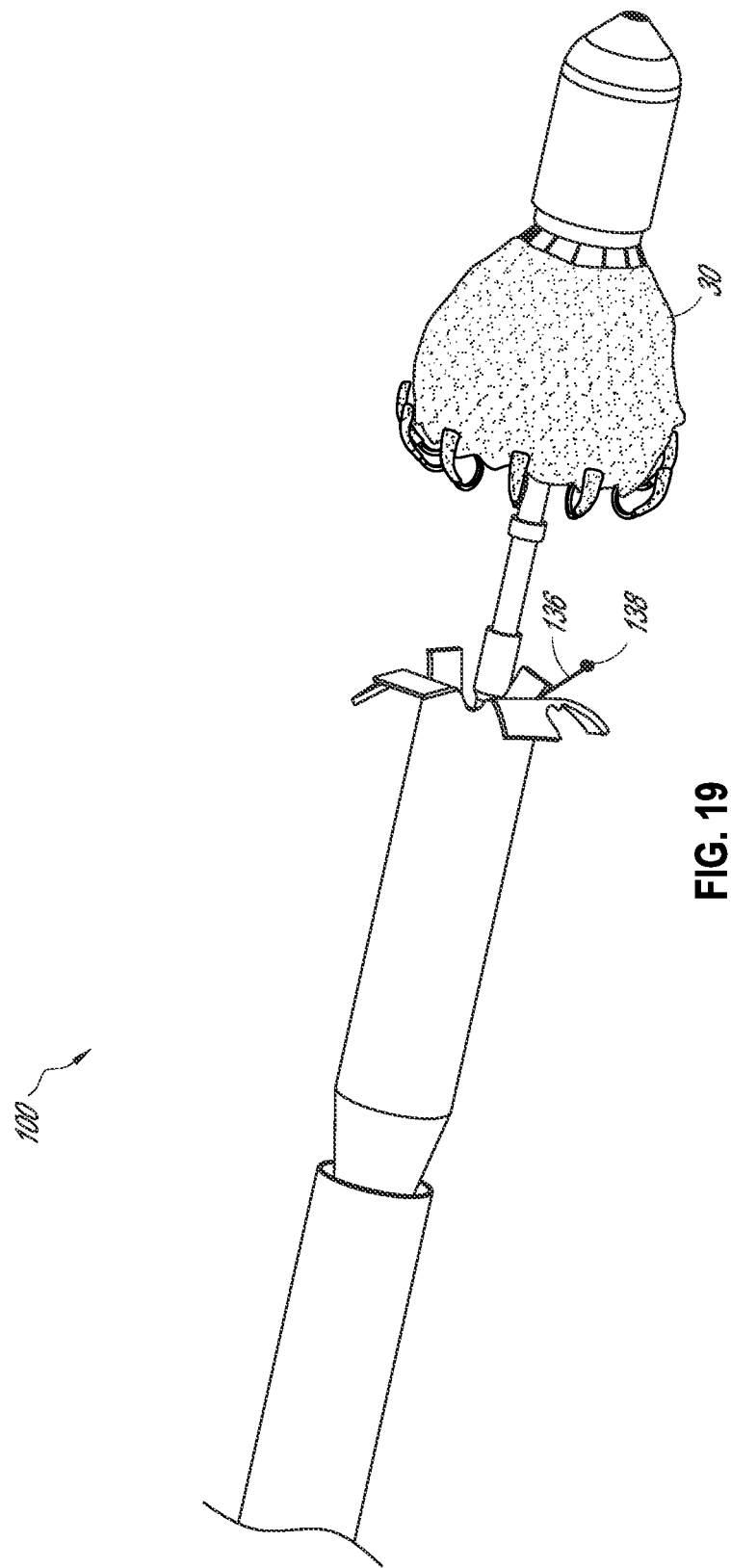

With reference next to the step of FIG. 18, the lock 129 has been moved relatively away from the tether retention member 134 to release the end 138 of the tether 136. In so doing, the second end 31 of the implant 30 is allowed to further radially expand. It should be noted that the first end 33 of the implant 30 can remain covered by the nose cone 118 during this step such that the first end 33 remains in a radially compacted state. With reference next to the step of FIG. 19, the tether 136 and end 138 can be retracted into the delivery system 100.

Figure 20:
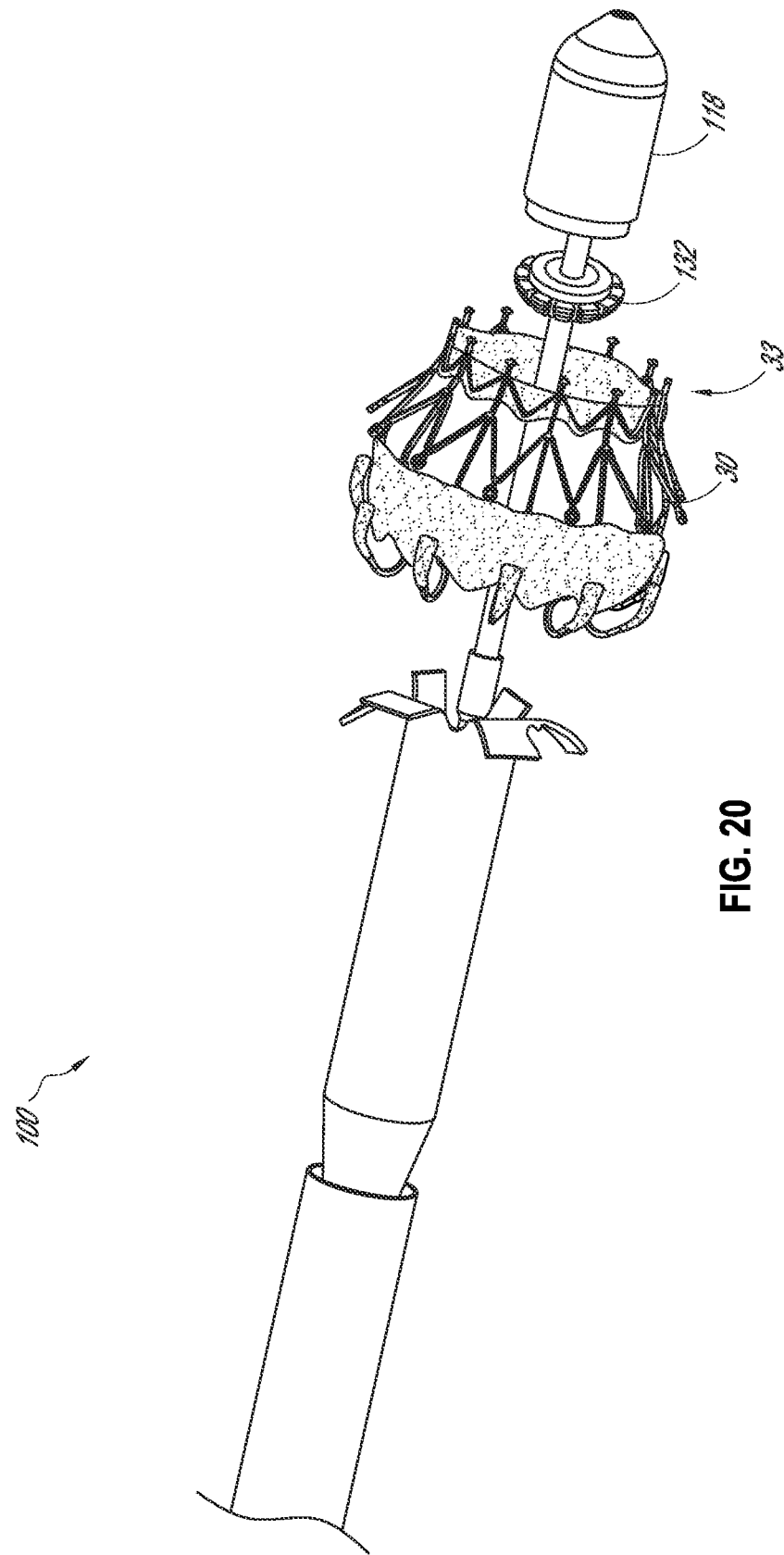
Figure 21:
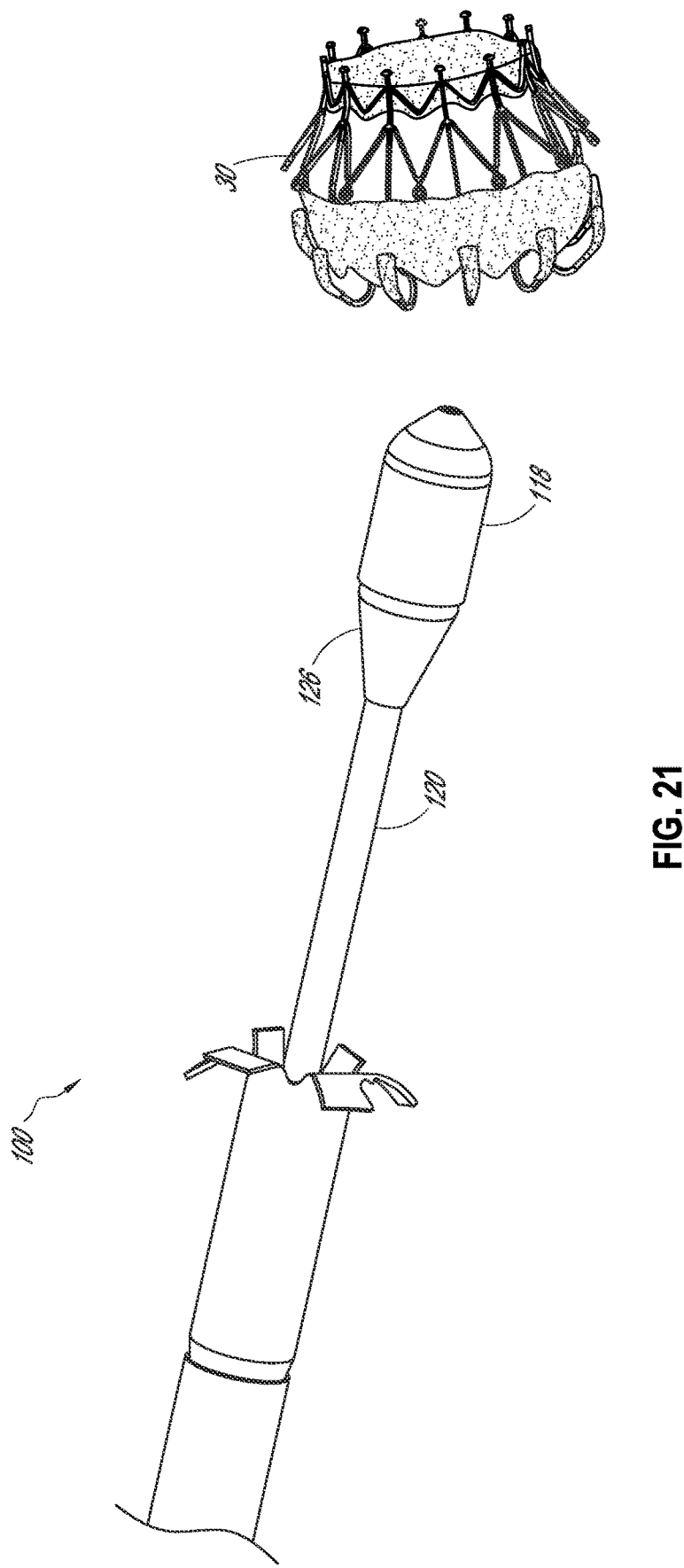
Figure 23:
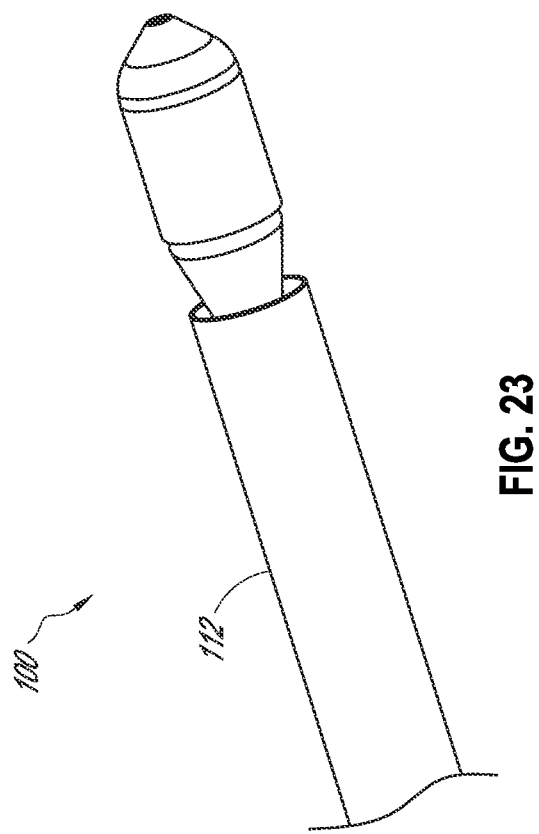
Figure 24:
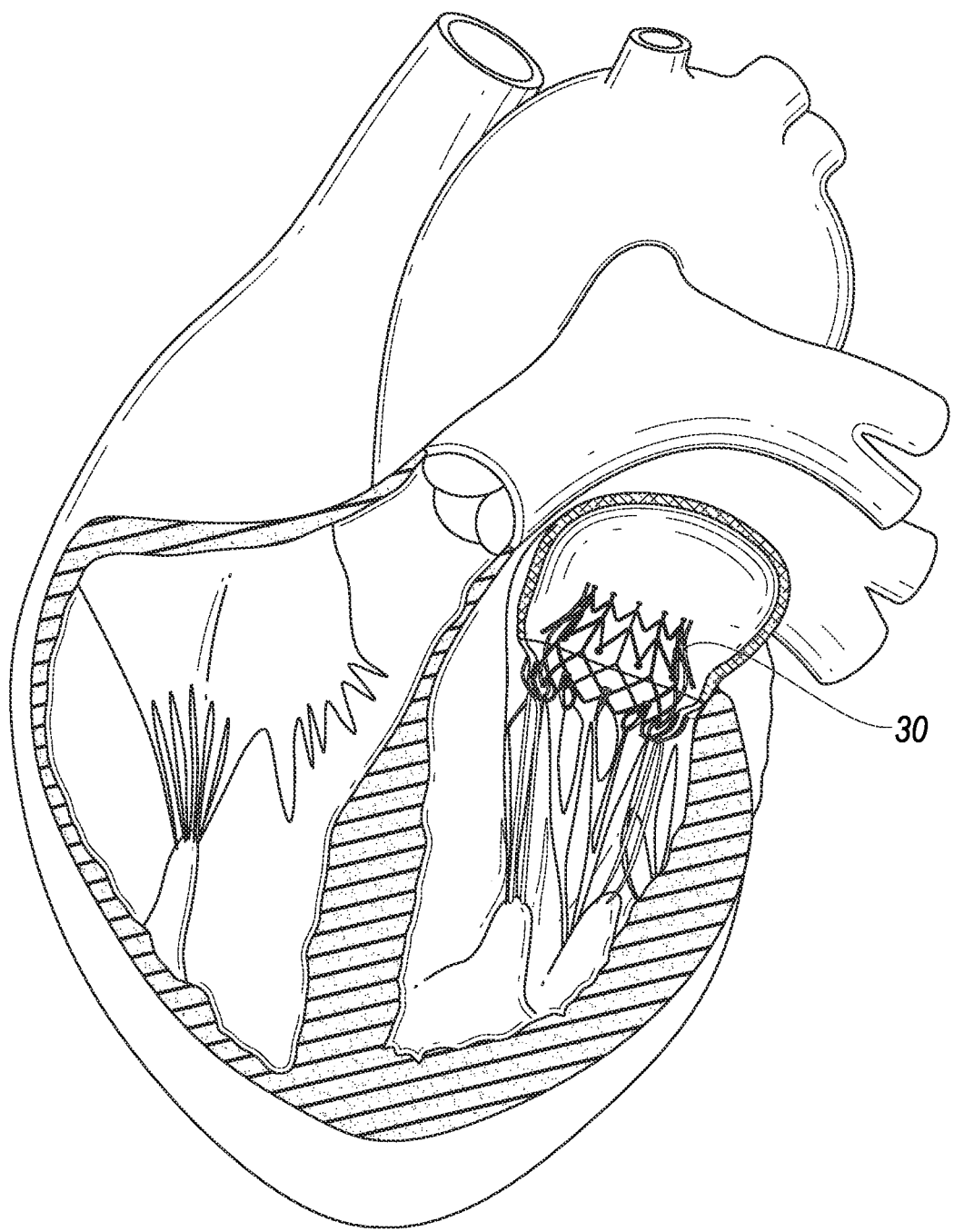
FIG. 24 illustrates a schematic representation of a prosthesis positioned within the heart.

With reference next to the step of FIG. 20, the inner retention member 132 and/or the first end 33 of the implant 30 can be moved relatively away from the nose cone 118 such that the first end 33 of the implant 30 can radially expand. This can be achieved by either distally moving the nose cone 118 relative to the inner retention member 132 and/or moving the inner retention member 132 proximally relative to the nose cone 118. With reference next to the step of FIG. 21, the plug 126, attached to the plug shaft 120, can be moved relatively toward the nose cone 118 to engage the nose cone 118. The plug 126 and/or plug shaft 120 can cover multiple of the inner components to facilitate extraction of the delivery system 100 from the body after delivery of the implant 30 to the in situ location. As shown in the step of FIG. 22, the outer elongate hollow member 116 can be further moved relatively toward the introducer sheath 112. As shown in the step of FIG. 23, various other components of the delivery system 100 can be moved relatively toward the introducer sheath 112 to reduce the form factor of the delivery system and further facilitate extraction of the delivery system 100 from the body. FIG. 24 illustrates the implant 30 positioned within a native valve, such as a native mitral valve.

Figure 31:
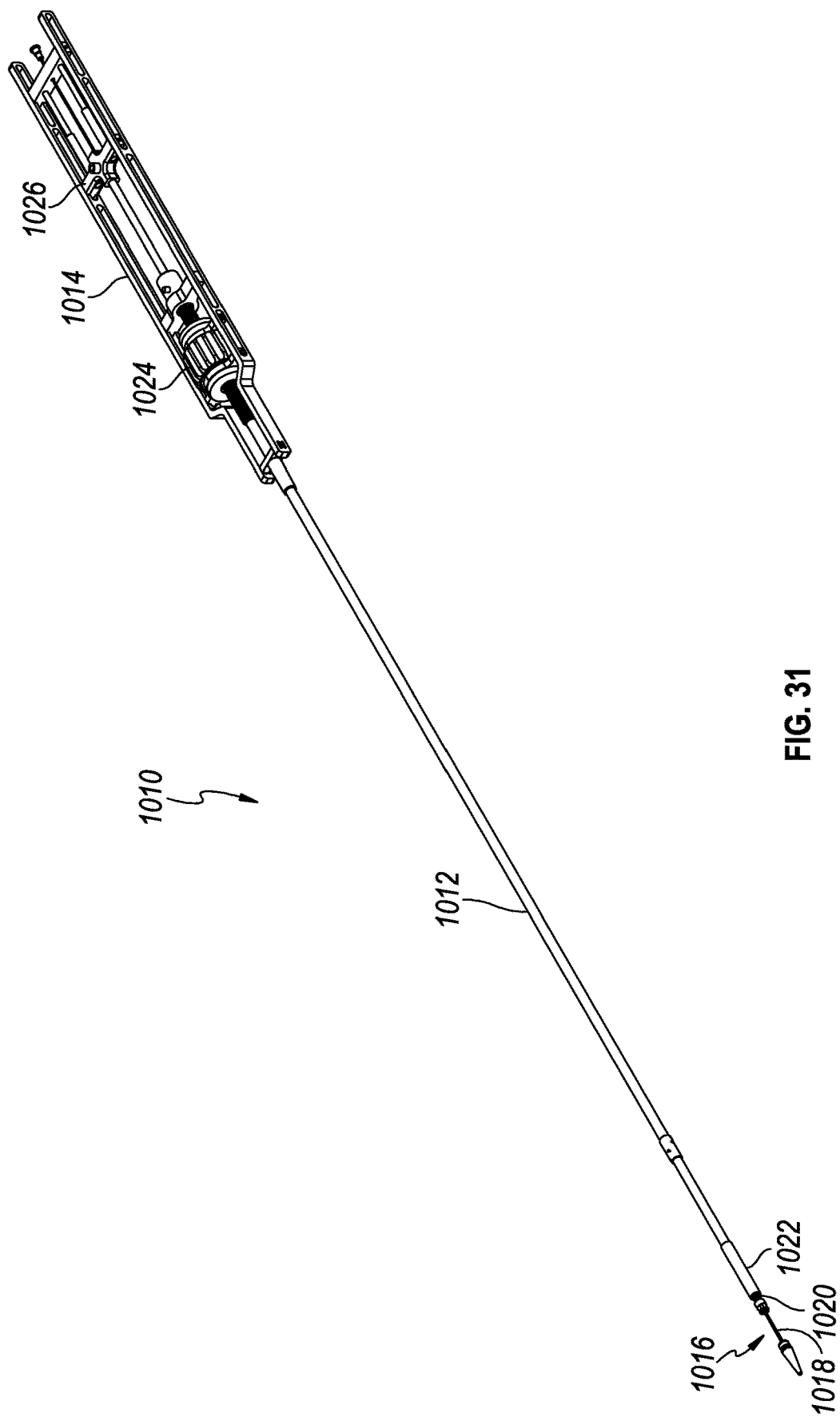
FIG. 31 shows an embodiment of a delivery system.

With reference to FIG. 31, an embodiment of a delivery device or system 1010 is shown. The delivery system can be used deploy a prosthesis, such as a replacement heart valve, within the body. The illustrated embodiment comprises an elongate, delivery system configured to be advanced through a patient's vasculature in a percutaneous delivery approach. The delivery system 1010 can be rigid and yet flexible to be able to pass through the vasculature while also navigating the curvosities of the same. While the delivery system 1010 is described in connection with a percutaneous delivery approach, and more specifically a transfemoral delivery approach, it should be understood that features of delivery system 1010 can be applied to any other delivery system described herein, including delivery systems 10, 100, 200 which are described in connection with a transapical delivery approach. Moreover, features of delivery systems 10, 100, 200 can be applied to delivery system 1010.

The delivery system 1010 can include an elongate shaft assembly 1012 comprising a proximal end and a distal end, wherein a handle 1014 is coupled to the proximal end of the assembly 1012. The elongate shaft assembly 1012 can be used to hold the prosthesis for advancement of the same through the vasculature to a treatment location. The elongate shaft assembly 1012 can include an implant retention area 1016 that can be used for this purpose. In some embodiments, the elongate shaft assembly 1012 can hold an expandable prosthesis in a compressed state at implant retention area 1016 for advancement of the prosthesis within the body. The elongate shaft assembly 1012 may then be used to allow controlled expansion of the prosthesis at the treatment location. The implant retention area 1016 is shown at the distal end of the delivery device, but may also be at other locations.

The elongate shaft assembly 1012 can include one or more subassemblies such as an inner assembly 1018, a mid shaft assembly 1020, and an outer sheath assembly 1022, as will be described in more detail below. The inner assembly 1018, mid shaft assembly 1020, and outer sheath assembly 1022 can be configured to deliver a prosthesis positioned within the implant retention area 1016 to a treatment location. One or more of the subassemblies can then be moved to allow the prosthesis to be released at the treatment location. For example, one or more of the subassemblies may be movable with respect to one or more of the other subassemblies. The handle 1014 can include various control mechanisms 1024, 1026 that be used to control the movement of the various subassemblies as will also be described in more detail below. In this way, the prosthesis can be controllably loaded onto the delivery device 1010 and then later deployed within the body.

Figure 32:
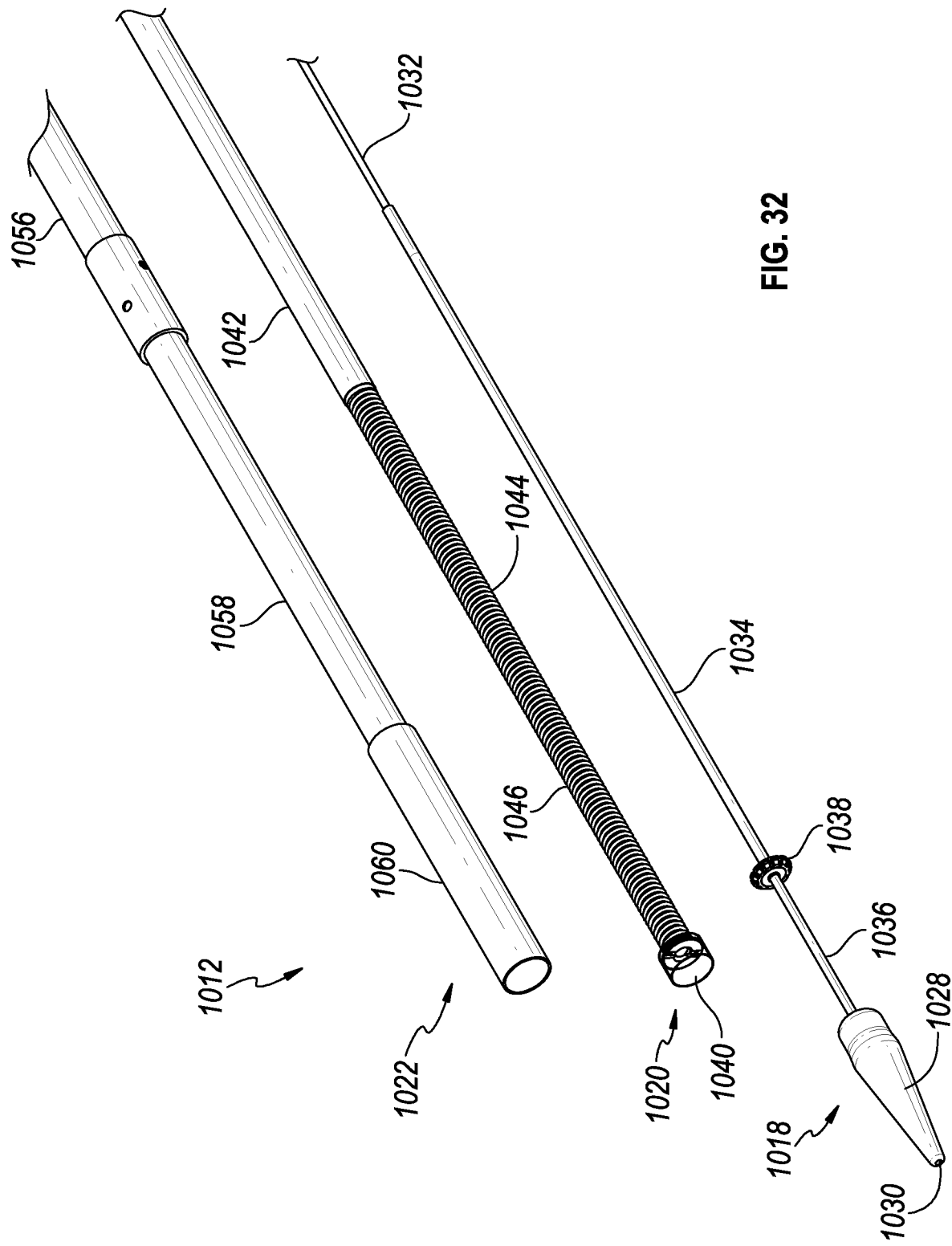
FIG. 32 is an exploded view of the distal end of the delivery system of FIG. 31.
Figure 33:
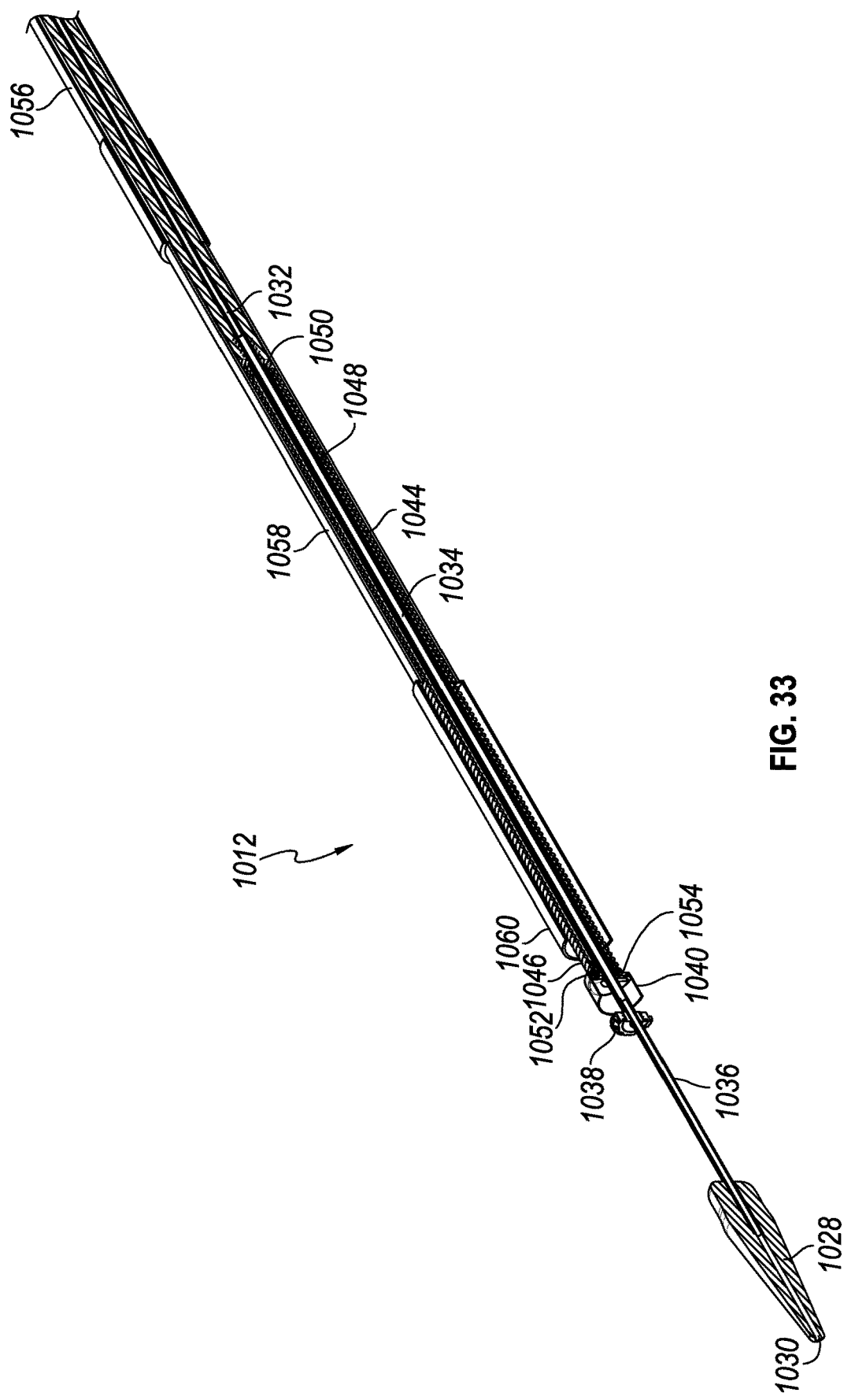
FIG. 33 is a cross-section view of the distal end of the delivery system of FIG. 31.

With continued reference to the subassemblies of the elongate shaft assembly 1012, FIGS. 32 and 33 respectively illustrate an exploded and cross-sectional view of the same. The inner assembly 1018 may be an elongate member, and in some embodiments, may have a nose cone 1028 on its distal end. The nose cone can be made of polyurethane for atraumatic entry and to minimize injury to venous vasculature. The nose cone can also be radiopaque to provide for visibility under fluoroscopy. Nose cone 1028 can share features of other nose cones described herein, such as nose cones 28, 118, 1128.

The inner assembly 1018 may include a lumen 1030 sized and configured to slidably accommodate a guidewire so that the delivery device 1010 can be advanced over the guidewire through the vasculature. The inner assembly 1018 may also be a steerable catheter which may or may not need or use a guidewire.

The inner assembly 1018 can comprise a tube, such as a hypodermic tube or hypo tube 1032. The tube can be made from one of any number of different materials including nitinol, stainless steel, and medical grade plastics. The tube can be a single piece tube or multiple pieces connected together. Using a tube made of multiple pieces can allow the tube to provide different characteristics along different sections of the tube, such as rigidity and flexibility. For example, in some embodiments it can be desirable, and/or needful, for the delivery device 1010 to have greater flexibility at the distal end of the device, where flexibility is not as necessary for the proximal end.

In some embodiments a first segment made of a hypo tube 1032 can extend along a majority of the length of the inner assembly. For example, the illustrated metal hypo tube 1032 extends from a luer fitting 1062 within the handle 1016 (FIGS. 36A-C) at the proximal end towards the distal end up until a second segment 1034 of the inner assembly 1018 before the implant retention area 1016. The hypo tube 1032 can provide column strength (pushability) to the inner assembly. The second segment 1034 of the inner assembly 1018 can be made of a more flexible material. For example, the second segment can comprise a wire 1034 such as a multi-stranded wire, wire rope, or wire coil. The wire 1034 can surround a more flexible tube, such as a plastic tube, or it may be formed as a tube without any additional inner materials or core. Thus, in some embodiments, the wire 1034 can be a hollow core wire rope. The wire 1034 can provide the inner assembly 1018 with strength, similar to the hypo tube, but it can also provide more flexibility to allow for navigating the curvosities of the vasculature, such as within the heart.

In some embodiments, the wire 1034 extends distally from the hypo tube 1032 to the nose cone 1028. In some embodiments, the inner assembly 1018 can include a third segment 1036. The third segment can be positioned at the implant retention area 1016 and between the second segment 1034 and the nose cone 1028. For example, the third segment can comprise a second wire 1036 such as a multi-stranded wire, wire rope, or wire coil. The second wire 1036 can surround a more flexible tube, such as a plastic tube, or it may be formed as a tube without any additional inner materials or core. The second wire 1036 may also be a hollow core wire rope.

In some embodiments, the second wire 1036 can have an outer diameter smaller than the first wire 1034. As the second wire is positioned at the implant retention area 1016, it can be desirable that the second wire 1036 have as small an outer diameter as possible, to reduce the size of the delivery device loaded with a prosthesis. The prosthesis may be able to provide some of the desired rigidity or strength characteristics of the delivery device at the implant retention area 1016 and this may allow the segment 1036 to have an even smaller outer diameter.

In some embodiments, the third segment 1036 can comprise a plastic tube. The plastic tube can extend from the nose cone 1028 to the first segment 1032. The second segment 1034 can surround the third segment 1036 and be positioned between the first segment 1032 and the implant retention area 1016. For example, the second segment 1034 can be a hollow core wire rope that surrounds the third segment 1036.

The inner assembly 1018 can also include a prosthesis retention mechanism such as an inner retention ring 1038 that can be used to engage with the prosthesis. The inner retention ring 1038 can share features with other retention members, such as inner retention members 132, 232. Examples of prostheses that may be engaged on the prosthesis retention mechanism when the delivery device 1010 is used to deliver a replacement heart valve are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, the entirety of these patents and publications are hereby incorporated by reference and made a part of this specification. For example, the inner retention ring 1038 can include a plurality of slots configured to engage with struts on the prosthesis. The inner retention ring 1038 can be mounted on the tube of the inner assembly 1018, such as at the junction of the distal end of the second segment 1034 and the proximal end of the third segment 1036. The inner retention ring 1038 can also be part of the implant retention area 1016, and may be at the proximal end of the implant retention area 1016.

Struts or other parts of a prosthesis can be engaged with the inner retention ring 1038 and an outer retention member can cover both the prosthesis and the inner retention ring 1038 to secure the prosthesis on the delivery device 1010. This outer retention member can be part of one of the other one or more subassemblies of the elongate shaft assembly 1012.

In the illustrated embodiment, the outer retention member is a support tube or outer retention ring 1040 which is part of the mid shaft assembly 1020. The mid shaft assembly 1020 can slide over the inner assembly 1018 and the outer retention ring 1040 can slide over the inner assembly 1018 and the inner retention ring 1038 to encircle the inner retention ring 1038. In this way the outer retention ring 1040 can be used to help secure a prosthesis to or release it from the delivery device 1010. The inner and outer retention rings and the delivery device generally may be similar to those disclosed in U.S. Pat. Nos. 8,414,644 and 8,652,203, the entire contents of both of which are hereby incorporated by reference herein and made a part of this specification. This is inclusive of the entire disclosure, including other apparatuses and methods described therein, and is not in any way limited to the disclosure of the inner and outer retentions and/or the delivery device.

Like the inner assembly 1018, the mid shaft assembly 1020 can be a single piece tube or multiple pieces connected together to provide different characteristics along different sections of the tube. As has been mentioned, in some embodiments it can be desirable, and/or needful, for the delivery device 1010 to have greater flexibility at the distal end of the device, where flexibility is not as necessary for the proximal end. The illustrated mid shaft assembly 1020 has a first segment 1042, a second segment 1044, and a third segment 1040 being the outer retention ring 1040. The first segment 1042 is preferably formed of plastic, but could also be a metal hypo tube or other material.

Figure 34:
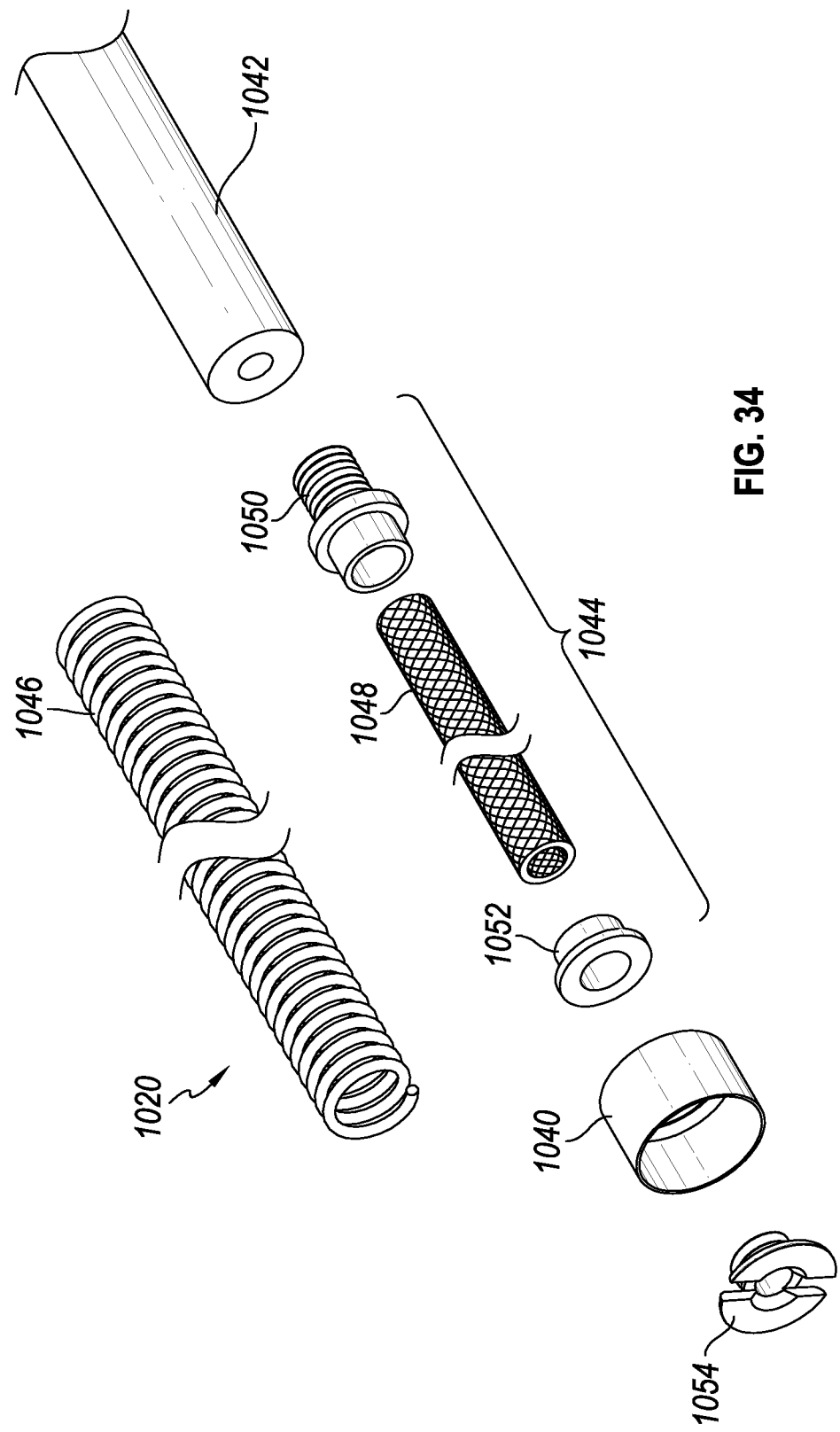
FIG. 34 shows an exploded view of a mid shaft assembly that may be used in the delivery system of FIG. 31.

The second segment 1044 is shown including a metal coil spring 1046 which is connected to the outer retention ring 1040 at one end and to the plastic tube 1042 at the other end. FIG. 34 shows an exploded view of the mid shaft assembly 1020 including the components of the second segment 1044. As shown, the second segment 1044 can include an inner member 1048 and an outer member 1046. The mid shaft assembly 1020 also can include various coupling members 1050, 1052, 1054 that can be used to connect the different first and third segments to the second segment, as well as to connect the inner 1048 and outer 1046 members.

One of the inner 1048 and outer 1046 members can be a compression member and the other can be a tension member. The compression member and the tension member can be concentrically arranged. They are also both highly flexible. As shown, the outer member is a coil spring 1046 and the inner member is a braided wire 1048. A length of a coil spring or a braided wire can be highly flexible and can be moved in many directions. For example, they can both be twisted around a full 180 degrees or more, depending on the length of the material. The compression member and the tension member can provide a balance of forces with flexibility without over stretching or too much shortening.

It will be understood that a compression member by itself, such as a coil spring and/or HDPE tube, can provide certain benefits, but also has certain draw backs. A compression member can apply a distally directed force on the inner retention member 1038 and can oppose proximally directed forces. But, compression members do not generally perform well under tension. For example, a spring can stretch when under tension. It will be understood, that when the mid shaft assembly 1020 is being slid away from the inner retention member 1038, for example, to release a prosthesis, it could experience resistance that could cause the spring to stretch such that the prosthesis is not released. Adding a tension member, such as a braided wire, can prevent this from occurring as the tension member can limit the amount of stretching of the compression member. The braided wire helps pull back the spring, but also has some give to expand and compress with the spring. The tension member can provide the required flexibility but resist stretching. Thus the compression and tension members can beneficially allow for increased flexibility while also providing more reliable implant release capabilities.

As has been mentioned, the mid shaft assembly 1020 can include various coupling members 1050, 1052, 1054. A first coupling member 1050 can be used to connect the first 1042 and second 1044 segments. The first coupling member 1050 can be made of metal or plastic and is shown with a plug end to form a friction fit with the first member 1042. The second member can be fastened to the first coupling member 1050 such as by adhesive or ultrasonic welding. In some embodiments the inner member can attach to an inside surface of the first coupling member 1050 and the outer member 1046 can attach to an outside surface of the first coupling member 1050. The second coupling member 1052 can attach to the inner and outer members in a similar manner. The third segment 1040 can be attached to the second segment 1044 by the interaction of the second 1052 and third 1054 coupling members. The third coupling member 1054 can be received in the second coupling member 1052 via snap fit connection with the third segment securely positioned between the second and third coupling members. It will be understood that this is just one example of how the various segments could be connected.

In some embodiments the sheath assembly 1012 has only two subassemblies which can be the inner 1018 and mid shaft 1020 assemblies as have been described. In some such embodiments, though the outer retention ring 1040 is shown as a relatively short ring, it could also be elongate and could extend from the inner retention ring 1038 to the nose cone 1028 when in a fully advanced position. In addition, the outer member 1046 such as a coil spring could be covered with a sheath such as sheath made of polytetrafluoroethylene (PTFE) or expanded polytetrafluoroethylene (ePTFE).

Returning now to FIGS. 32 and 33, the outer sheath assembly 1022 will be described. The outer sheath assembly 1022 is disposed so as to be slidable over the inner assembly 1018 and the mid shaft assembly 1020. Like the inner assembly 1018 and the mid shaft assembly 1020, the outer sheath assembly 1022 can be a single piece tube or multiple pieces connected together to provide different characteristics along different sections of the tube. As has been mentioned, in some embodiments it can be desirable, and/or needful, for the delivery device 1010 to have greater flexibility at the distal end of the device, where flexibility is not as necessary for the proximal end. The illustrated outer sheath assembly 1022 has a first segment 1056, a second segment 1058, and a third segment 1060.

The first segment 1056 is a tube and is preferably formed plastic, but could also be a metal hypo tube or other material. In some embodiments, the tube 1056 is formed of a polyether block amide (PEBA) or other type of a thermoplastic elastomer (TPE). In particular the tube 1056 can be a wire braided reinforced PEBA which can enhance pushability and trackability.

The second segment 1058 can be a metal hypo tube which in some embodiments may be cut or have slots. The hypo tube can provide structural rigidity, while the cuts can provide for flexibility in the hypo tube. The second segment can be a laser cut nitinol tube designed to allow adequate flexibility but with sufficient column strength to provide finite control for stepwise retraction of the outer sheath during deployment. For example, the remaining material can form a series of interconnected "H"s that are offset by 90 degrees. As another example, the hypo tube can be cut into a series of rings with small connecting members extending between the rings. For example two equally spaced connecting members can be used to connect two rings and the subsequent connecting members can be offset 90 degrees. Other numbers of connecting members such as one, two, three, four, etc. can also be used.

The tube 1058 can be covered or encapsulated with a layer of ePTFE, PTFE, or other material so that the outer surface of the outer sheath assembly is generally smooth.

The third segment 1060 can be a tube formed of a plastic or metal material. In a preferred embodiment, the third segment is formed of ePTFE or PTFE. In some embodiments this sheathing material can be relatively thick to prevent tearing and to help maintain a self-expanding implant in a compacted configuration. In some embodiments the material of the third segment 1060 is the same material as the coating on the cut hypo tube 1058.

Figure 35:
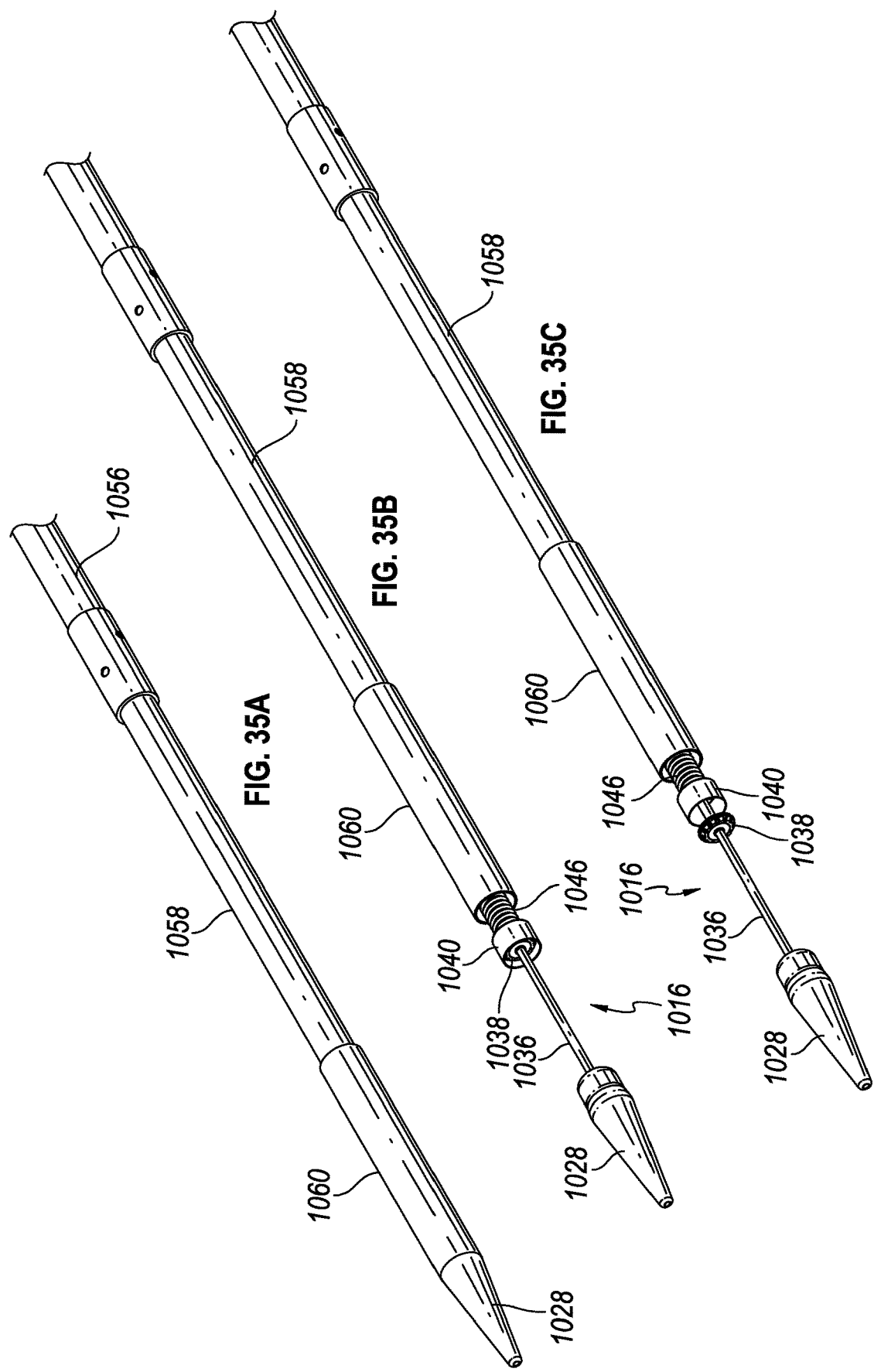
FIGS. 35A-C illustrates a distal end of the delivery system of FIG. 31 in a series of positions.

Looking now to FIGS. 35A-C, the relative movements of the one or more subassemblies of the elongate shaft assembly 1012 will be described. FIG. 35A shows the outer sheath assembly 1022 in its distal most position. The third segment 1060 of the outer sheath is shown in contact with the proximal end of the nose cone 1028. In this position, a prosthesis can be held within the elongate shaft assembly 1012 for advancement of the same through the vasculature to a treatment location.

Once at the desired location, the outer sheath assembly 1022 can be retracted proximally to expose a portion of or all of a prosthesis in the implant retention area 1016. FIG. 35B illustrates the elongate shaft assembly 1012 with the outer sheath assembly 1022 can be retracted proximally to expose the entire implant retention area 1016. The mid shaft assembly 1020 can then be retracted as shown in FIG. 35C. This can allow any portion of the prosthesis engaged between the inner retention member 1038 and the outer retention member 1040 to be released. In some delivery methods this would be the last step to fully deploying the prosthesis such as replacement heart valve.

Figure 36:
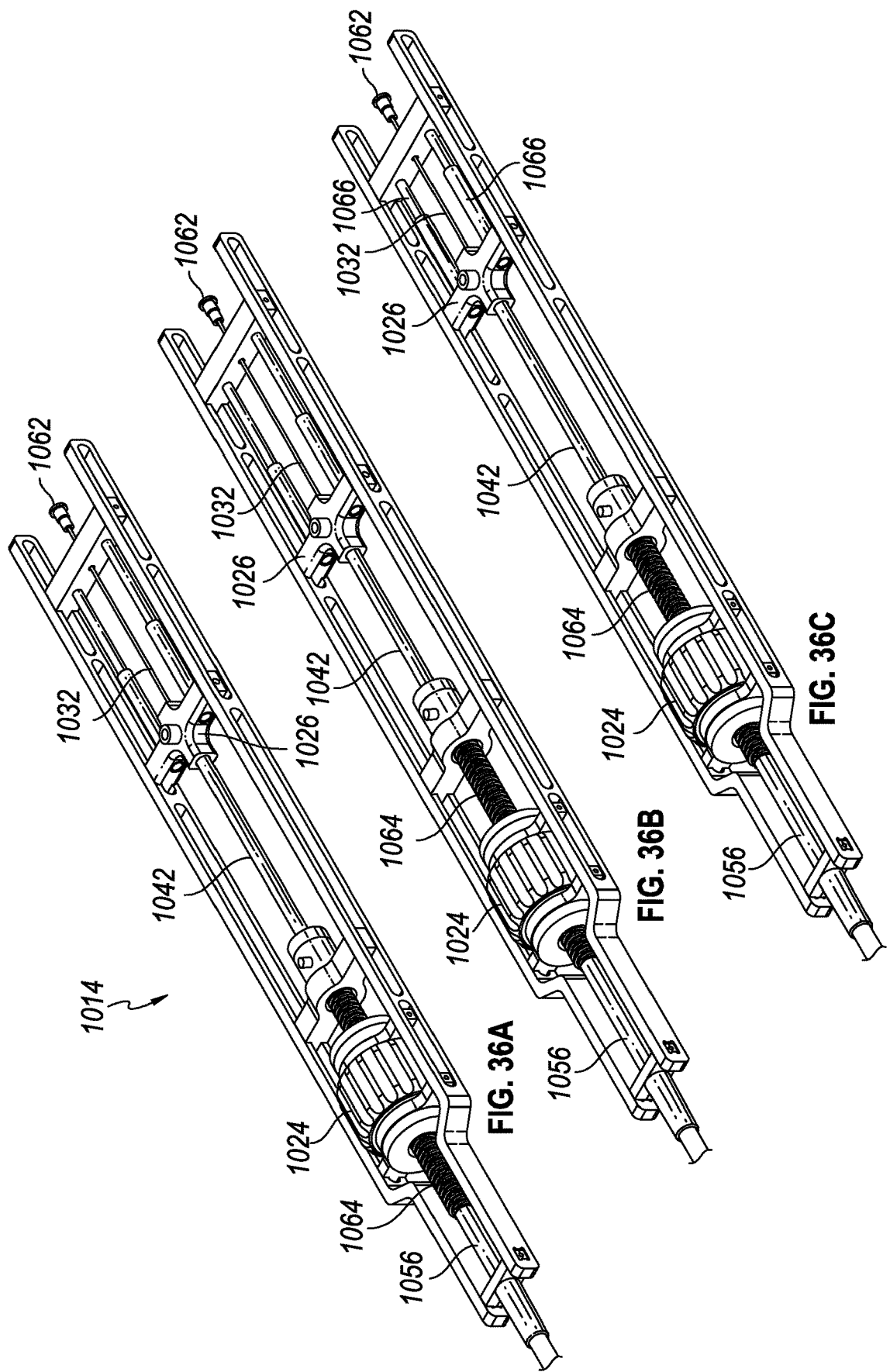
FIGS. 36A-C show a handle of the delivery system of FIG. 31 in a series of positions.

FIGS. 36A-C show the corresponding position of the control mechanisms and components at the handle from the configurations of FIGS. 35A-C. To move the outer sheath assembly 1022 between the advanced position (FIG. 35A) and the retracted position (FIG. 35B), the control mechanism 1024 is actuated. As shown, the control mechanism 1024 is a retraction knob that is rotated. This causes a lead screw 1064 connected to the first segment 1056 of the outer sheath assembly 1022 to move proximally (FIG. 36B). Then, to move the mid shaft assembly 1020, the control mechanism 1026 is pulled backwards (FIG. 36C). Springs 1066 can be used to give feedback to the user and to better control the movement of the mid shaft assembly 1020 to thereby provide a controlled release of the prosthesis. In addition, the springs 1066 can maintain a continuous extension force between the inner assembly 1018 and the mid shaft assembly 1020 to keep the inner retention member 1038 bottomed out inside the outer retention member 1040 so that the distal tip of the delivery device 1010 maintains maximum flexibility and freedom of motion and the prosthesis does not unlock and prematurely deploy.

Aspects of the handle 1014, can be used in conjunction with other delivery devices described herein, such as delivery devices 10, 100, 200, 1100. For example, in some embodiments, the control mechanism 1024 can be used with a lead screw 1064 as shown in FIGS. 36A and 36B connected to an outer elongate hollow member shaft 114, to control movement of the outer elongate hollow member shaft 114 and/or elongate hollow member 116 as shown in FIG. 9. Moreover, springs 1066 as shown in FIG. 36C can be operably coupled to the locking shaft 122 to control movement of the locking shaft 122 and/or lock 129 as shown in FIG. 11. For example, the springs 1066 can be used to bias locking shaft 122 in a retracted position such that actuation of a switch can cause the locking shaft 122 to move towards the retracted position. This can, in some embodiments, facilitate release of the tether, wire or suture 32 from the tether retention assembly 128.

The handle can also include any number of luers that can allow all subassemblies to be perfused with saline. The perfusion of saline can eliminate or reduce air embolism risk due to catheter use and can also provide flushing capability for the delivery procedure.

Figure 37:
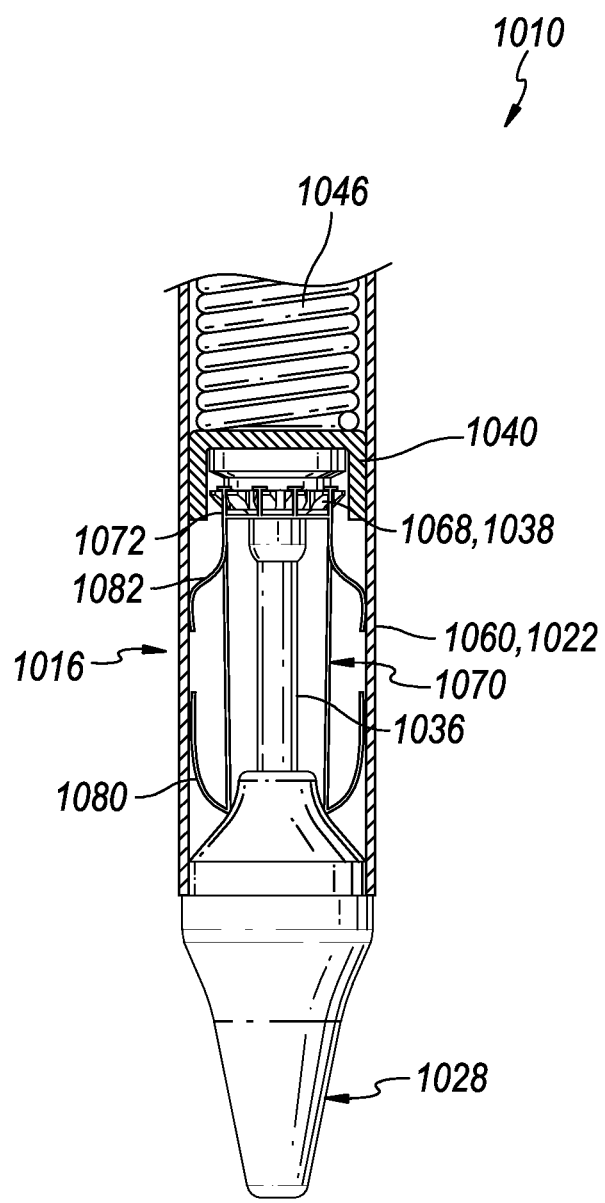
FIG. 37 shows a prosthesis within a delivery system.

Turning now to FIG. 37, an embodiment of a delivery device 1010 is shown with a schematic representation of a prosthesis 1070, such as a replacement heart valve, within the implant retention area 1016. As has been discussed, the outer retention ring 1040 and the outer sheath 1022 can cooperate to hold the replacement heart valve 1070 in a compacted configuration. The inner retention ring 1038 is shown engaging the struts 1072 at the proximal end of the heart valve 1070. For example, teeth 1068 on the inner retention ring 1038 can engage the struts 1072 which may end in tabs on the proximal end of the heart valve 1070. The outer retention ring 1040 can be positioned over the inner retention ring 1038 so that the proximal end of the replacement heart valve 1070 is trapped therebetween, securely attaching it to the delivery device 1010. The prosthesis 1070 can include one or more sets of anchors, such as distal anchors 1080 and proximal anchors 1082. The prosthesis 1070 may be similar to the replacement heart valves disclosed in U.S. Pat. Nos. 8,403,983, 8,414,644 and 8,652,203, and U.S. Patent Publication Nos. 2011/0313515, 2012/0215303, 2014/0277390, 2014/0277422, 2014/0277427, the entirety of these patents and publications are hereby incorporated by reference and made a part of this specification.

The delivery device 1010 may be provided to users with a prosthesis 1070 preinstalled. In other embodiments, the prosthesis 1070 can be loaded onto the delivery device shortly before use, such as by a physician or nurse.

Methods of use of the delivery device in connection with a replacement mitral valve will now be described. In particular, the delivery device 1010 can be used in a method for percutaneous delivery of the replacement mitral valve to treat patients with moderate to severe mitral regurgitation. The below methods are just a few examples of the how the delivery device may be used. It will be understood that the delivery devices described herein can be used as part of other methods as well.

Figure 38:
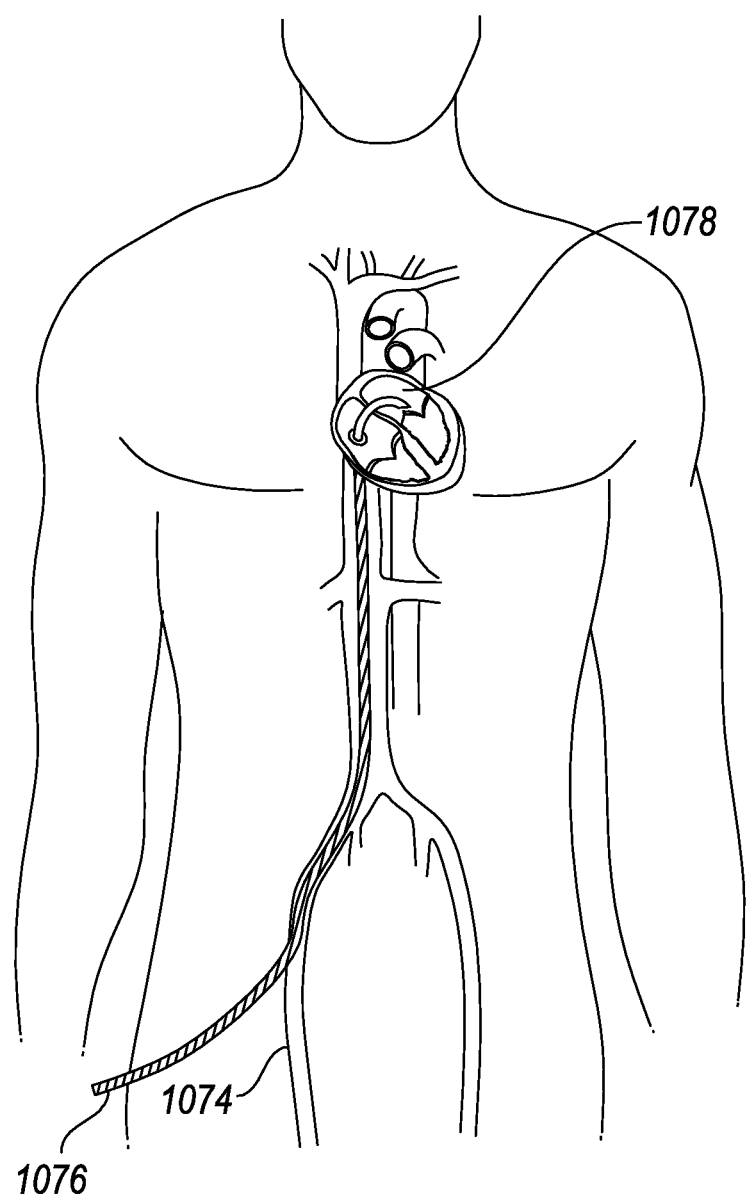
FIG. 38 is a schematic representation showing an access path into the heart.

As shown in FIG. 38, in one embodiment a guidewire 1076 can be placed in the ipsilateral femoral vein 1074 and advanced to the right atrium. A transseptal puncture using known techniques can then be performed to obtain access to the left atrium. The guidewire 1076 can then be advanced in to the left atrium and then to the left ventricle. FIG. 38 shows a guidewire 1076 extending from the ipsilateral femoral vein 1074 to the left atrium 1078. A guidewire snare can be placed in the descending aorta through the ipsilateral femoral artery. The guidewire can be advanced into the ascending aorta and then the snare can be used to snare the guidewire. The guidewire snare can then be withdrawn to externalize the guidewire from the ipsilateral femoral artery. The physician now has access to both ends of the guidewire. It will be understood that one or more introducer sheaths, catheters and/or guidewires may need to be used to get a guidewire externalized at both the ipsilateral femoral vein and the ipsilateral femoral artery. In addition, the initial guidewire discussed above may not be the same as the ultimate externalized guidewire. As will be explained in more detail below, having an externalized guidewire can be useful for positioning the delivery device, especially the distal end of the delivery device, and for helping the delivery device turn some corners. Some embodiments may not use an externalized guidewire. For example, a steerable catheter may be used instead of the externalized guidewire.

With the guidewire in place, the delivery device 1010 can be advanced over the guidewire through the lumen 1030. The delivery device can then be advanced to the right atrium, through the septal puncture and the left atrium and into the left ventricle. A steering snare may be used to help advance and position the delivery device correctly. In addition, tension can be applied to one end of the externalized guidewire to help advance and position the delivery device. These additional helps can be particularly useful to get the delivery device to make the bend from extending up into the right atrium and then extending down into the left ventricle.

The construction and flexibility of the delivery device can allow it to make the relatively sharp turns described above, in particular the turns from entering the right atrium to the septum and then from the septum to the mitral valve. It should be understood that the bending experienced by the delivery device especially between the right atrium and the mitral valve are relatively complex and are generally not in a single plane. This part of the delivery device may experience bending between 110-180 degrees and typically between 130-160 degrees, of course this is dependent on the actual anatomy of the patient.

Though the entire elongate shaft assembly 1012 may be experiencing some bending or flex, typically it is predominately the second segments 1034, 1044, 1058 of the subassemblies (FIG. 32) that will be experiencing most of the bending. This can be both when making the turns as the delivery device is being advanced, and also when the prosthesis is being positioned at the mitral valve. The nose cone 1028 can also be flexible and may be bent during turning and at various other times during the procedure.

The second segments 1034, 1044, 1058 can have a bendable length that is substantially aligned with one another. The second segments 1034, 1044, 1058 may each have a bendable length of at least between about 3.5 to 4 inches (8.9 to 10.2 cm). In some embodiments, the second segment 1058 of the outer sheath can have a bendable length of about 3⅝ inches (9.2 cm), the second segment 1044 of the mid shaft can have a bendable length of about 4¾ inches (12.1 cm), and the second segment of the inner assembly can have a bendable length of about 5.5 to 6 inches (14 to 15.2 cm). In some embodiments, the relative bendable lengths of the second segments can increase going from the outermost subassembly to the innermost subassembly of the elongate shaft assembly 1012.

The delivery device can include a radially-compacted replacement mitral valve 1070 that has been preloaded within the implant retention area 1016. With the distal end of the delivery device 1010 within the left ventricle, the operator can begin to deploy the replacement mitral valve. Using one or more of the delivery device, the guidewire, and a snare, the distal end of the delivery device can be positioned to be substantially perpendicular to the plane of the mitral annulus. It can also be positioned so that the tips of the distal most anchors 1080 on the replacement valve 1070 are midway between a plane formed by the top of the mitral annulus and a plane formed by the tops of the papillaries. The chordae tendineae extend between the native leaflets attached to the mitral annulus and the papillaries.

The user can then begin rotating the retraction knob 1024 to retract the outer sheath assembly 1022 until the distal most anchors 1080 begin to extend out from the outer sheath assembly 1022. Retracting the outer sheath assembly 1022 can allow the valve to self-expand. In some embodiments, the outer sheath assembly 1022 can be at least partially retracted. The distal anchors 1080 can then be positioned between the chordae tendineae. The angle and depth of the distal anchors 1080 then be adjusted to engage one or more leaflet of the mitral valve. Thus, the distal anchors 1080 can be move back towards the annulus and in some embodiments may engage the leaflet and/or the ventricular side of the annulus. At the same time, the proximal end of the replacement heart valve 1070 can remain retained by the delivery device in an at least partially radially compacted state. This can allow the position of the replacement heart valve 1080 to still be readily adjusted.

In some embodiments, the distal anchors 1080 can be positioned first at one side of the left ventricle to engage the chordae tendineae and one valve leaflet before engaging the other side and the other leaflet. As the mitral valve is a bicuspid valve, the delivery device 1010 can be used to attach the distal anchors 1080 first to the posterior leaflet and then to anterior leaflet. This second part can be done after the replacement heart valve 1070 is expanded or further expanded by further retracting the outer sheath assembly 1022.

In some embodiments, the entrance route of the delivery device 1010 into the left atrium 1078 can bias the delivery device 1010 towards one side of the mitral valve. For example, the delivery device 1010 may be biased towards the posterior leaflet of the mitral valve. This can facilitate securing the distal anchors 1080 to the posterior side or the posterior leaflet first, prior to expanding or further expanding the replacement heart valve 1070. The distal anchors 1080 can then be secured to the anterior side of the mitral valve or to the anterior leaflet.

After the distal anchors 1080 are released, the delivery device 1010 and replacement heart valve 1080 can be moved proximally, which in some embodiments, causes the distal anchors to engage the native leaflets and/or native valve annulus. In addition to physically moving the delivery device, this may also be done by pushing the guidewire from the venous side towards the mitral annulus. Once the distal anchors 1080 are properly placed, the delivery device 1010 can then release the proximal anchors 1082 and the proximal end of the replacement heart valve 1070. This can allow further self-expansion of the replacement heart valve 1070 so that the proximal anchors 1082 engage the upstream or atrial side of the native annulus, and the replacement heart valve 1070 is deployed in operational condition. This can be by fully retracting the outer sheath assembly 1022, such as by rotating the control knob 1024, until the replacement valve 1070 has reached its fully expanded state.

Figure 39:
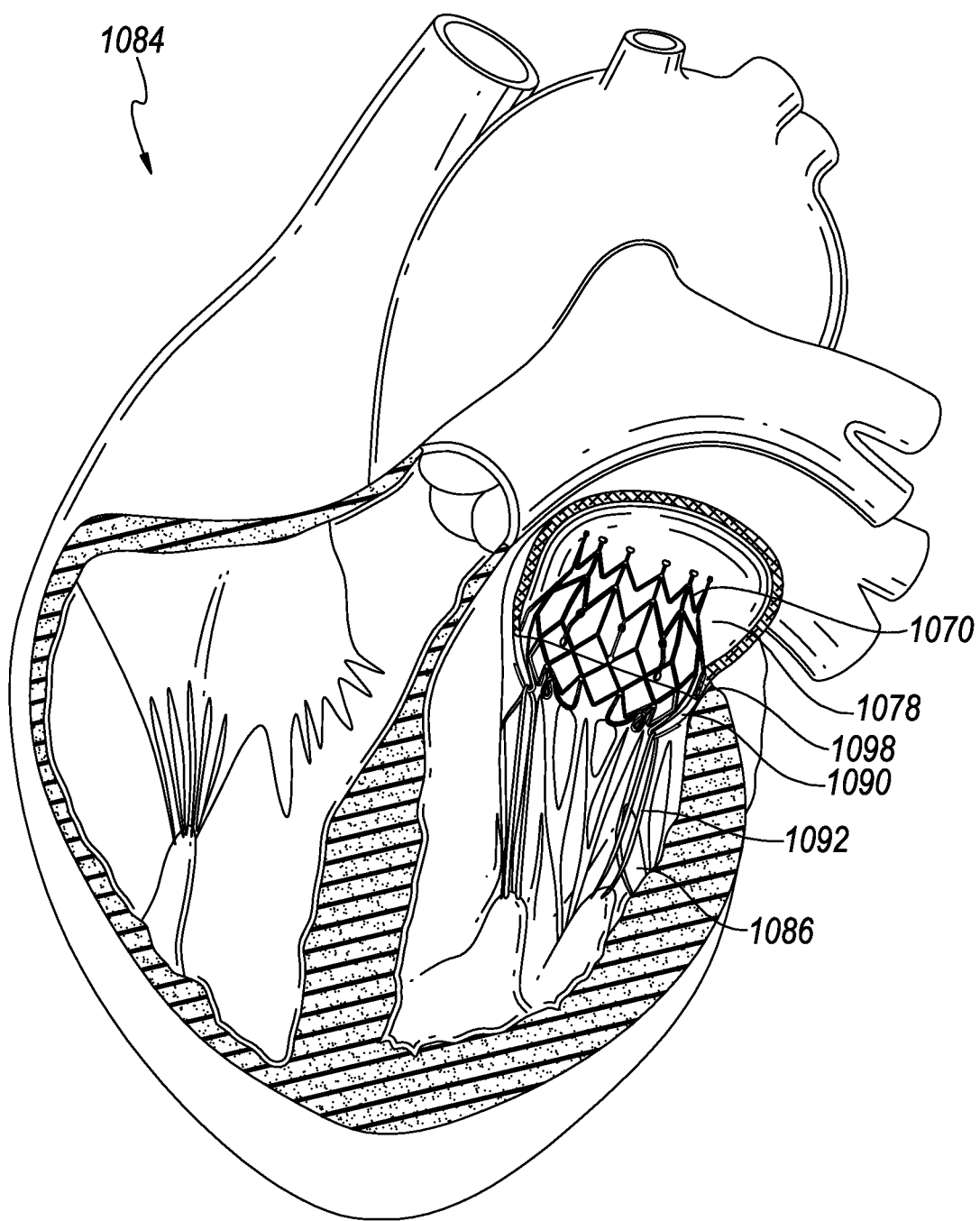
FIG. 39 illustrates a replacement heart valve deployed in the mitral valve between the left atrium and the left ventricle.

The outer retention ring 1040 can then be moved away from the inner retention ring 1038 to release the proximal end of the replacement valve 1070 from the delivery device 1010. This can be done by moving the control mechanism 1026 on the handle 1014 downward which is connected to the outer retention ring 1040. The proximal anchors 1082 can flare radially outward under the self-expansion force of the valve 1070 and engage with the upstream or atrial side of the native mitral valve annulus. Foreshortening of the valve 1070 can cause the distal and proximal anchors to move towards one another to securely grasp the native mitral valve annulus and the leaflets between their opposingly directed anchor tips, and the replacement heart valve 1070 is fully and securely installed as can be seen in FIG. 39. The delivery device 1010 can then be removed from the body.

It will be understood that in some embodiments the replacement heart valve 1070 may not be self expanding, and the partial and full deployment may be accomplished by one or more inflatable balloons or the like. In addition, one of more inflatable balloons may be a part of the delivery device, such as part of the inner assembly 1018 and can positioned at the implant retention area 1016 as part of the third segment 1036.

Looking at FIG. 39, a schematic representation of the replacement heart valve 1070 is depicted installed in a human heart 1084. The heart is shown in cross-section, and represents typical anatomy, including a left atrium 1078 and left ventricle 1086. The left atrium 1078 and left ventricle 1086 communicate with one another through a mitral annulus 1098. Also shown schematically in FIG. 39 is a native anterior mitral leaflet 1090 having chordae tendineae 1092 that connect a downstream end of the anterior mitral leaflet 1090 and to the left ventricle 1086.

As shown, the replacement heart valve 1070 is disposed so that the mitral annulus 1098 is between the distal anchors 1080 and the proximal anchors 1082. All or most of the replacement heart valve 1070 extends into the left atrium 1078. The portion of the replacement heart valve 1070 disposed upstream of the annulus 1098 (toward the left atrium) can be referred to as being positioned supra-annularly. The portion generally within the annulus 1098 is referred to as positioned intra-annularly. The portion downstream of the annulus is referred to as being positioned sub-annularly (toward the left ventricle). In the illustrated embodiment, only a part of the foreshortening portion is positioned intra-annularly or sub-annularly, and the rest of the replacement heart valve 1070 is supra-annular.

Replacement heart valves can be delivered to a patient's heart mitral valve annulus in various ways, such as by open surgery, minimally-invasive surgery, and percutaneous or transcatheter delivery through the patient's vasculature.

Looking now at FIGS. 40A-B, another embodiment of a delivery device 1110 is shown. The delivery device 1110 can function in a similar manner to that described above. The delivery device 1110 can include components which share similar structure to those of other delivery devices described herein, such as delivery devices 10, 100, 200, 1010. For example, such components can include, but are not limited to, elongate shaft assemblies 1012, 1112, handles 1014, 1114, implant retention areas 1016, 1116, inner assemblies 1018, 1118, mid shaft assemblies 1020, 1120, outer sheath assemblies 1022, 1122 control mechanisms 1024, 1026, 1124, 1126, nose cones 28, 118, 1028, 1128, hypo tubes 1032, 1132, segments 1036, 1136, inner retention rings and mechanisms 132, 232, 1038, 1138, outer retention rings 1040, 1140, segments 1042, 1044, 1142, 1144, outer members 1046, 1146, segments 1058, 1060, 1158, 1160 and/or lead screws 1064, 1164.

As shown in the illustrated embodiment, a primary difference between the delivery device 1010 and the delivery device 1110 is the length of the elongate shaft assemblies 1012, 1112. It will be appreciated that a short elongate shaft assembly 1112 can be more easily used in an open heart procedure or other more direct procedures than the percutaneous procedure starting at the leg that has been described above with respect to delivery device 1010. For example, the delivery device 1110 can be used in procedures such as a transapical procedure as described above. At the same time, the delivery device 1110 can still be relatively flexible to allow, for example, advancement through the pulmonary veins or the wall of the left atrium and then bending of the delivery device for proper placement at the mitral valve. The delivery device 1110 can share features with delivery devices described herein, such as delivery devices or systems 10, 100, 200, 1010.

The construction and flexibility of the delivery device can allow it to make the relatively sharp turns described above. It should be understood that the bending experienced by the delivery device may be relatively complex and are generally not in a single plane. This part of the delivery device may experience bending between 65-130 degrees; of course this is dependent at least partially on the actual anatomy of the patient.

Though the entire elongate shaft assembly 1112 may be experiencing some bending or flex, it is predominately the second segments 1134, 1144, 1158 of the subassemblies that will be experiencing most of the bending. This is both when making the turns as the delivery device is being advanced, and also when the prosthesis is being positioned at the mitral valve. The nose cone 1128 can also be flexible and may be bent during turning and at various other times during the procedure. In some embodiments of the delivery device 1110, the second segments can extend from the first segments to the handle. Some subassemblies may or may include the first segments described above with respect to the delivery device 1110. The second segments 1134, 1144, 1158 can have a bendable length that is substantially aligned with one another. The second segments 1134, 1144, 1158 may each have bendable lengths similar to those described above for second segments 1034, 1044, 1058, though they may also be longer or shorter. For example the second segment 1158 of the outer sheath assembly may extend from the first segment 1160 to the screw 1164, while the other second segments 1134, 1144 may be shorter.

It will be understood that the delivery devices, such as delivery devices 10, 100, 200, 1010, 1110 can include many additional features similar to those described in U.S. Pat. Nos. 8,414,644 and 8,652,203, the entirety of each of which are hereby incorporated by reference and made a part of this specification. For example, the nose cone can include a prosthesis retention mechanism such as an inner retention ring that can be used to engage with the prosthesis as may be described in these applications. Struts or other parts of a prosthesis can be engaged with the inner retention ring and the nose cone can cover both the prosthesis and the inner retention ring to secure the prosthesis on the delivery devices 10, 100, 200, 1010, 1110. In addition, the delivery device can be used in delivery methods similar to those described in the above referenced patents and application.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method for controllably delivering a replacement mitral valve with a delivery system, the method comprising:
    delivering a distal end of the delivery system using a transfemoral delivery approach into a left atrium of a heart and toward a native mitral valve, wherein the delivery system comprises an outer sheath assembly, a mid shaft assembly and an inner assembly, wherein the outer sheath assembly and the mid shaft assembly at least partially retain the replacement mitral valve in a radially compacted state over the inner assembly;
    with the distal end of the delivery system within a left ventricle of the heart, proximally retracting the outer sheath assembly relative to the mid shaft assembly to expose distal anchors of the replacement mitral valve and to allow the distal anchors to self-expand into an expanded state, while a proximal end of the replacement mitral valve remains retained in an at least partially radially compacted state by the mid shaft assembly;
    positioning the distal anchors to engage one or more native leaflets of the native mitral valve; and
    proximally retracting the mid shaft assembly relative to the inner assembly to disengage the mid shaft assembly from the proximal end of the replacement mitral valve to allow a proximal anchoring portion of the replacement mitral valve to self-expand into a radially expanded state.

2. The method of claim 1, wherein a distal end of the mid shaft assembly comprises an enlarged outer retention member.

3. The method of claim 1, wherein disengaging the proximal end of the replacement mitral valve comprises releasing a tether coupled to the replacement mitral valve.

4. The method of claim 1, wherein the proximal anchoring portion of the replacement mitral valve extends radially outwardly relative to the proximal end of the replacement mitral valve to facilitate engagement with an annulus of the native mitral valve.

5. The method of claim 1, wherein positioning the distal anchors to engage one or more native leaflets of the native mitral valve comprises positioning one or more of the distal anchors between chordae tendineae and radially outward of the one or more native leaflets of the native mitral valve.

6. A method for delivering a replacement heart valve to replace a native heart valve between an atrium and a ventricle of a heart using a delivery system, the method comprising:
    delivering a distal end of the delivery system using a transfemoral delivery approach into the atrium of the heart and toward the native heart valve between the atrium and the ventricle, wherein the delivery system comprises an outer sheath assembly, a mid shaft assembly and an inner assembly, wherein the outer sheath assembly and the mid shaft assembly at least partially retain the replacement heart valve in a radially compacted state over the inner assembly;
    with the distal end of the delivery system within the ventricle of the heart, proximally retracting the outer sheath assembly to expose distal anchors of the replacement heart valve and to allow the distal anchors to self-expand into an expanded state, while a portion of the replacement heart valve remains retained in an at least partially radially compacted state by the mid shaft assembly;
    positioning the distal anchors to engage one or more native leaflets of the native heart valve; and
    releasing a retained portion of the replacement heart valve from the mid shaft assembly to fully expand the replacement heart valve from the delivery system, wherein the releasing step comprising proximally retracting the mid shaft assembly relative to the inner assembly to disengage the mid shaft assembly from the proximal end of the replacement mitral valve to allow a proximal anchoring portion of the replacement mitral valve to self-expand into a radially expanded state.

7. The method of claim 6, wherein the mid shaft assembly at least partially retains a proximal portion of the replacement heart valve, and wherein releasing the retained portion of the replacement heart valve from the mid shaft assembly comprises releasing the proximal portion of the replacement heart valve.

8. The method of claim 6, wherein the mid shaft assembly comprises a tube.

9. The method of claim 6, wherein positioning the distal anchors to engage one or more native leaflets of the native mitral valve comprises positioning one or more of the distal anchors between chordae tendineae and radially outward of the one or more native leaflets of the native heart valve.

10. The method of claim 6, further comprising moving the delivery system proximally after exposing the distal anchors of the replacement heart valve and allowing the distal anchors to self-expand into an expanded state.

11. The method of claim 6, wherein the replacement heart valve is a replacement mitral valve, and the distal end of the delivery system is delivered into a left atrium of the heart and toward a native mitral valve, with the distal end positioned within the left ventricle.

12. The method of claim 11, wherein positioning the distal anchors to engage one or more native leaflets of the native mitral valve comprises engaging a first distal anchor to one valve leaflet of the native mitral valve before engaging a second distal anchor to the other valve leaflet of the native mitral valve.

13. The method of claim 11, wherein positioning the distal anchors to engage one or more native leaflets of the native mitral valve comprises engaging a first distal anchor to a posterior leaflet of the native mitral valve before engaging a second distal anchor to an anterior leaflet of the native mitral valve.

14. The method of claim 6, wherein the distal anchors are configured to point in a first direction prior to expansion and then rotate to point in a second, longitudinally opposite direction after expansion.

15. The method of claim 6, wherein the delivery system comprises a tether coupled to the replacement heart valve, and further comprising disengaging the tether from the replacement heart valve to fully expand the replacement heart valve from the delivery system.

16. The method of claim 6, wherein the outer sheath assembly comprises a slotted hypotube.

17. The method of claim 6, wherein the delivery system comprises a handle comprising a plurality of actuatable mechanisms configured to control movement of the outer sheath assembly and the mid shaft assembly.

18. The method of claim 17, wherein the plurality of actuatable mechanisms comprises a rotatable knob configured to retract the outer sheath assembly.

19. The method of claim 6, wherein the mid shaft assembly is more flexible at its distal end than at its proximal end.

20. The method of claim 6, wherein the delivery system is steerable.

* * * * *